United States Patent
Xiao et al.

(10) Patent No.: US 12,209,251 B2
(45) Date of Patent: Jan. 28, 2025

(54) MODIFIED ADENO-ASSOCIATED VIRUS 5 CAPSIDS AND USES THEREOF

(71) Applicant: The University of North Carolina at Chapel Hill, Chapel Hill, NC (US)

(72) Inventors: Xiao Xiao, Chapel Hill, NC (US); Randolph Qian, Chapel Hill, NC (US); Juan Li, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 426 days.

(21) Appl. No.: 17/307,117

(22) Filed: May 4, 2021

(65) Prior Publication Data
US 2021/0348197 A1 Nov. 11, 2021

Related U.S. Application Data

(60) Provisional application No. 63/020,139, filed on May 5, 2020.

(51) Int. Cl.
| | |
|---|---|
| C12N 15/86 | (2006.01) |
| A61K 48/00 | (2006.01) |
| C07K 14/005 | (2006.01) |
| C12N 7/00 | (2006.01) |

(52) U.S. Cl.
CPC ............ *C12N 15/86* (2013.01); *C07K 14/005* (2013.01); *C12N 7/00* (2013.01); *A61K 48/00* (2013.01); *C12N 2750/14122* (2013.01); *C12N 2750/14123* (2013.01); *C12N 2750/14143* (2013.01)

(58) Field of Classification Search
CPC combination set(s) only.
See application file for complete search history.

(56) References Cited

U.S. PATENT DOCUMENTS

| | | | |
|---|---|---|---|
| 2016/0289275 A1 * | 10/2016 | Chiorini | A61K 48/0008 |
| 2018/0371024 A1 | 12/2018 | Asokan et al. | |

FOREIGN PATENT DOCUMENTS

| | | | |
|---|---|---|---|
| CN | 105163764 A | 12/2015 | |
| WO | WO-2014144229 A1 * | 9/2014 | ........... A61P 1/16 |
| WO | 2014193716 A2 | 12/2014 | |
| WO | 2016126857 A1 | 8/2016 | |
| WO | 2018064611 A1 | 4/2018 | |
| WO | 2019213668 A1 | 11/2019 | |

OTHER PUBLICATIONS

Govindasamy, Lakshmanan, et al. "Structural insights into adeno-associated virus serotype 5." Journal of virology 87.20: 11187-11199. (Year: 2013).*
Qian, Randolph, et al. "Directed evolution of AAV serotype 5 for increased hepatocyte transduction and retained low humoral seroreactivity." Molecular Therapy—Methods & Clinical Development 20: 122-132. (Year: 2021).*
"International Search Report and Written Opinion corresponding to International Application No. PCT/2021/030547 mailed Aug. 23, 2021".
Chiorini, John A., et al., "Cloning and Characterization of Adeno-Associated Virus Type 5", Journal of Virology 73(2):1309-1319 (Feb. 1999).
Mingozzi, Federico, et al., "Improved Hepatic Gene Transfer by Using an Adeno-Associated Virus Serotype 5 Vector", Journal of Virology 76(20):10497-10502 (Oct. 2002).
Qian, Randolph, et al., "Directed Evolution of AAV Serotype 5 for Increased Hepatocyte Transduction and Retained Low Humoral Seroreactivity", Molecular Therapy: Methods & Clinical Development 20:122-132 (Mar. 2021).
"International Preliminary Report on Patentability corresponding to International Application No. PCT/2021/030547 mailed Nov. 17, 2022".
"Extended European Search Report corresponding to European Application No. 21800414.1 dated May 23, 2024".
Qian, Randolph, "Bioengineering of Adeno-Associated Virus Serotype 5 for Increased Liver Transduction and Retention of Low Humoral Seroreactivity", Phd Dissertation, University of North Carolina at Chapel Hill (Jun. 6, 2020) 170 pages.
Sen, Dwaipayan, et al., "Improved adeno-associated virus (AAV) serotype 1 and 5 vectors for gene therapy", Scientific Reports 3:1832 (May 13, 2013) 6 pages.

* cited by examiner

*Primary Examiner* — Arthur S Leonard
*Assistant Examiner* — Josephine M Gonzales
(74) *Attorney, Agent, or Firm* — Myers Bigel, P.A.

(57) ABSTRACT

The present invention provides mutant adeno-associated virus serotype 5 (AAV5) that exhibit altered capsid properties, e.g., increased infectivity in human liver cells and/or minimal binding to human neutralizing antibodies. The present invention further provides libraries of mutant AAV5 comprising one or more mutations in a capsid gene. The present invention further provides methods of generating the mutant AAV5 and mutant AAV5 libraries, and compositions comprising the mutant AAV5. The present invention further provides recombinant AAV5 (rAAV5) virions that comprise a mutant capsid protein. The present invention further provides nucleic acids comprising nucleotide sequences that encode mutant capsid proteins.

19 Claims, 20 Drawing Sheets

Specification includes a Sequence Listing.

```
AAV5    1  ATGTCTTTTGTTGATCACCCTCCAGATTGGTTGGAAGAAGTTGGTGAAGGTCTTCGCGAG
MV1     1  ATGTCTTTTGTTGATCACCCTCCAGATTGGTTGGAAGAAGTTGGTGAAGGTCTTCGCGAG
MV18    1  ATGTCTTTTGTTGATCACCCTCCAGATTGGTTGGAAGAAGTTGGTGAAGGTCTTCGCGAG
MV20    1  ATGTCTTTTGTTGATCACCCTCCAGATTGGTTGGAAGAAGTTGGTGAAGGTCTTCGCGAG
MV50    1  ATGTCTTTTGTTGATCACCCTCCAGATTGGTTGGAAGAAGTTGGTGAAGGTCTTCGCGAG
MV53    1  ATGTCTTTTGTTGATCACCCTCCAGATTGGTTGGAAGAAGTTGGTGAAGGTCTTCGCGAG

AAV5   61  TTTTTGGGCCTTGAAGCGGGCCCACCGAAACCAAAACCCAATCAGCAGCATCAAGATCAA
MV1    61  TTTTTGGGCCTTGAAGCGGGCCCACCGAAACCAAAACCCAATCAGCAGCATCAAGATCAA
MV18   61  TTTTTGGGCCTTGAAGCGGGCCCACCGAAACCAAAACCCAATCAGCAGCATCAAGATCAA
MV20   61  TTTTTGGGCCTTGAAGCGGGCCCACCGAAACCAAAACCCAATCAGCAGCATCAAGATCAA
MV50   61  TTTTTGGGCCTTGAAGCGGGCCCACCGAAACCAAAACCCAATCAGCAGCATCAAGATCAA
MV53   61  TTTTTGGGCCTTGAAGCGGGCCCACCGAAACCAAAACCCAATCAGCAGCATCAAGATCAA

AAV5  121  GCCCGTGGTCTTGTGCTGCCTGGTTATAACTATCTCGGACCCGGAAACGGTCTCGATCGA
MV1   121  GCCCGTGGTCTTGTGCTGCCTGGTTATAACTATCTCGGACCCGGAAACGGTCTCGATCGA
MV18  121  GCCCGTGGTCTTGTGCTGCCTGGTTATAACTATCTCGGACCCGGAAACGGTCTCGATCGA
MV20  121  GCCCGTGGTCTTGTGCTGCCTGGTTATAACTATCTCGGACCCGGAAACGGTCTCGATCGA
MV50  121  GCCCGTGGTCTTGTGCTGCCTGGTTATAACTATCTCGGACCCGGAAACGGTCTCGATCGA
MV53  121  GCCCGTGGTCTTGTGCTGCCTGGTTATAACTATCTCGGACCCGGAAACGGTCTCGATCGA

AAV5  181  GGAGAGCCTGTCAACAGGGCAGACGAGGTCGCGCGAGAGCACGACATCTCGTACAACGAG
MV1   181  GGAGAGCCTGTCAACAGGGCAGACGAGGTCGCGCGAGAGCACGACATCTCGTACAACGAG
MV18  181  GGAGAGCCTGTCAACAGGGCAGACGAGGTCGCGCGAGAGCACGACATCTCGTACAACGAG
MV20  181  GGAGAGCCTGTCAACAGGGCAGACGAGGTCGCGCGAGAGCACGACATCTCGTACAACGAG
MV50  181  GGAGAGCCTGTCAACAGGGCAGACGAGGTCGCGCGAGAGCACGACATCTCGTACAACGAG
MV53  181  GGAGAGCCTGTCAACAGGGCAGACGAGGTCGCGCGAGAGCACGACATCTCGTACAACGAG

AAV5  241  CAGCTTGAGGCGGGAGACAACCCCTACCTCAAGTACAACCACGCGGACGCCGAGTTTCAG
MV1   241  CAGCTTGAGGCGGGAGACAACCCCTACCTCAAGTACAACCACGCGGACGCCGAGTTTCAG
MV18  241  CAGCTTGAGGCGGGAGACAACCCCTACCTCAAGTACAACCACGCGGACGCCGAGTTTCAG
MV20  241  CAGCTTGAGGCGGGAGACAACCCCTACCTCAAGTACAACCACGCGGACGCCGAGTTTCAG
MV50  241  CAGCTTGAGGCGGGAGACAACCCCTACCTCAAGTACAACCACGCGGACGCCGAGTTTCAG
MV53  241  CAGCTTGAGGCGGGAGACAACCCCTACCTCAAGTACAACCACGCGGACGCCGAGTTTCAG

AAV5  301  GAGAAGCTCGCCGACGACACATCCTTCGGGGGAAACCTCGGAAAGGCAGTCTTTCAGGCC
MV1   301  GAGAAGCTCGCCGACGACACATCCTTCGGGGGAAACCTCGGAAAGGCAGTCTTTCAGGCC
MV18  301  GAGAAGCTCGCCGACGACACATCCTTCGGGGGAAACCTCGGAAAGGCAGTCTTTCAGGCC
MV20  301  GAGAAGCTCGCCGACGACACATCCTTCGGGGGAAACCTCGGAAAGGCAGTCTTTCAGGCC
MV50  301  GAGAAGCTCGCCGACGACACATCCTTCGGGGGAAACCTCGGAAAGGCAGTCTTTCAGGCC
MV53  301  GAGAAGCTCGCCGACGACACATCCTTCGGGGGAAACCTCGGAAAGGCAGTCTTTCAGGCC

AAV5  361  AAGAAAAGGGTTCTCGAACCTTTTGGCCTGGTTGAAGAGGGTGCTAAGACGGCCCCTACC
MV1   361  AAGAAAAGGGTTCTCGAACCTTTTGGCCTGGTTGAAGAGGGTGCTAAGACGGCCCCTACC
MV18  361  AAGAAAAGGGTTCTCGAACCTTTTGGCCTGGTTGAAGAGGGTGCTAAGACGGCCCCTACC
MV20  361  AAGAAAAGGGTTCTCGAACCTTTTGGCCTGGTTGAAGAGGGTGCTAAGACGGCCCCTACC
MV50  361  AAGAAAAGGGTTCTCGAACCTTTTGGCCTGGTTGAAGAGGGTGCTAAGACGGCCCCTACC
MV53  361  AAGAAAAGGGTTCTCGAACCTTTTGGCCTGGTTGAAGAGGGTGCTAAGACGGCCCCTACC
```

*FIG. 4*

```
AAV5  421  GGAAAGCGGATAGACGACCACTTTCCAAAAGAAAGAAGGCTCGGACCGAAGAGGACTCC
MV1   421  GGAAAGCGGATAGACGACCACTTTCCAAAAGAAAGAAGGCTCGGACCGAAGAGGACTCC
MV18  421  GGAAAGCGGATAGACGACCACTTTCCAAAAGAAAGAAGGCTCGGACCGAAGAGGACTCC
MV20  421  GGAAAGCGGATAGACGACCACTTTCCAAAAGAAAGAAGGCTCGGACCGAAGAGGACTCC
MV50  421  GGAAAGCGGATAGACGACCACTTTCCAAAAGAAAGAAGGCTCGGACCGAAGAGGACTCC
MV53  421  GGAAAGCGGATAGACGACCACTTTCCAAAAGAAAGAAGGCTCGGACCGAAGAGGACTCC

AAV5  481  AAGCCTTCCACCTCGTCAGACGCCGAAGCTGGACCCAGCGGATCCCAGCAGCTGCAAATC
MV1   481  AAGCCTTCCACCTCGTCAGACGCCGAAGCTGGACCCAGCGGATCCCAGCAGCTGCAAATC
MV18  481  AAGCCTTCCACCTCGTCAGACGCCGAAGCTGGACCCAGCGGATCCCAGCAGCTGCAAATC
MV20  481  AAGCCTTCCACCTCGTCAGACGCCGAAGCTGGACCCAGCGGATCCCAGCAGCTGCAAATC
MV50  481  AAGCCTTCCACCTCGTCAGACGCCGAAGCTGGACCCAGCGGATCCCAGCAGCTGCAAATC
MV53  481  AAGCCTTCCACCTCGTCAGACGCCGAAGCTGGACCCAGCGGATCCCAGCAGCTGCGAATC

AAV5  541  CCAGCCCAACCAGCCTCAAGTTTGGGAGCTGATACAATGTCTGCGGGAGGTGGCGGCCCA
MV1   541  CCAGCCCAACCAGCCTCAAGTTTGGGAGCTGATACAATGTCTGCGGGAGGTGGCGGCCCA
MV18  541  CCAGCCCAACCAGCCTCAAGTTTGGGAGCTGATACAATGTCTGCGGGAGGTGGCGGCCCA
MV20  541  CCAGCCCAACCAGCCTCAAGTTTGGGAGCTGATACAATGTCTGCGGGAGGTGGCGGCTCA
MV50  541  CCAGCCCAACCAGCCTCAAGTTTGGGAGCTGATACAATGTCTGCGGGAGGTGGCGGCCCA
MV53  541  CCAGCCCAACCAGCCTCAAGTTTGGGAGCTGATACAATGTCTGCGGGAGGTGGCGGCCCA

AAV5  601  TTGGGCGACAATAACCAAGGTGCCGATGGAGTGGGCAATGCCTCGGGAGATTGGCATTGC
MV1   601  TTGGGCGACAATAACCAAGGTGCCGATGGAGTGGGCAATGCCTCGGGAGATTGGCATTGC
MV18  601  TTGGGCGACAATAACCAAGGTGCCGATGGAGTGGGCAATGCCTCGGGAGATTGGCATTGC
MV20  601  TTGGGCGACAATAACCAAGGTGCCGATGGAGTGGGCAATGCCTCGGGAGATTGGCATTGC
MV50  601  TTGGGCGACAATAACCAAGGTGCCGATGGAGTGGGCAATGCCTCGGGAGATTGGCATTGC
MV53  601  TTGGGCGACAATAACCAAGGTGCCGATGGAGTGGGCAATGCCTCGGGAGATTGGCATTGC

AAV5  661  GATTCCACGTGGATGGGGGACAGAGTCGTCACCAAGTCCACCCGAACCTGGGTGCTGCCC
MV1   661  GATTCCACGTGGATGGGGGACAGAGTCGTCACCAAGTCCACCCGAACCTGGGTGCTGCCC
MV18  661  GATTCCACGTGGATGGGGGACAGAGTCGTCACCAAGTCCACCCGAACCTGGGTGCTGCCC
MV20  661  GATTCCACGTGGATGGGGGACAGAGTCGTCACCAAGTCCACCCGAACCTGGGTGCTGCCC
MV50  661  GATTCCACGTGGATGGGGGACAGAGTCGTCACCAAGTCCACCCGAACCTGGGTGCTGCCC
MV53  661  GATTCCACGTGGATGGGGGACAGAGTCGTCACCAAGTCCACCCGAACCTGGGTGCTGCCC

AAV5  721  AGCTACAACAACCACCAGTACCGAGAGATCAAAAGCGGCTCCGTCGACGGAAGCAACGCC
MV1   721  AGCTACAACAACCACCAGTACCGAGAGATCAAAAGCGGCTCCGTCGACAGAAGCAACGCC
MV18  721  AGCTACAACAACCACCAGTACCGAGAGATCAAAAGCGGCTCCGTCGACAGAAGCAACGCC
MV20  721  AGCTACAACAACCACCAGTACCGAGAGATCAAAAGCGGCTCCGTCGACGGAAGCAACGCC
MV50  721  AGCTACAACAACCACCAGTACCGAGAGATCAAAAGCGGCTCCGTCGACAGAAGCAACGCC
MV53  721  AGCTACAACAACCACCAGTACCGAGAGATCAAAAGCGGCTCCGTCGACAGAAGCAACGCC

AAV5  781  AACGCCTACTTTGGATACAGCACCCCTGGGGGTACTTTGACTTTAACCGCTTCCACAGC
MV1   781  AACGCCTACTTTGGATACAGCACCCCTGGGGGTACTTTGACTTTAACCGCTTCCACAGC
MV18  781  AACGCCTACTTTGGATACAGCACCCCTGGGGGTACTTTGACTTTAACCGCTTCCACAGC
MV20  781  AACGCCTACTTTGGATACAGCACCCCTGGGGGTACTTTGACTTTAACCGCTTCCACAGC
MV50  781  AACGCCTACTTTGGATACAGCACCCCTGGGGGTACTTTGACTTTAACCGCTTCCACAGC
MV53  781  AACGCCTACTTTGGATACAGCACCCCTGGGGGTACTTTGACTTTAACCGCTTCCACAGC
```

FIG. 4 (CONT.)

```
AAV5   841 CACTGGAGCCCCCGAGACTGGCAAAGACTCATCAACAACTACTGGGGCTTCAGACCCCGG
MV1    841 CACTGGAGCCCCCGAGACTGGCAAAGACTCATCAACAACTACTGGGGCTTCAGACCCCGG
MV18   841 CACTGGAGCCCCCGAGACTGGCAAAGACTCATCAACAACTACTGGGGCTTCAGACCCCGG
MV20   841 CACTGGAGCCCCCGAGACTGGCAAAGACTCATCAACAACTACTGGGGCTTCAGACCCCGG
MV50   841 CACTGGAGCCCCCGAGACTGGCAAAGACTCATCAACAACTACTGGGGCTTCAGACCCCGG
MV53   841 CACTGGAGCCCCCGAGACTGGCAAAGACTCATCAACAACTACTGGGGCTTCAGACCCCGG

AAV5   901 TCCCTCAGAGTCAAAATCTTCAACATTCAAGTCAAAGAGGTCACGGTGCAGGACTCCACC
MV1    901 TCCCTCAGAGTCAAAATCTTCAACATTCAAGTCAAAGAGGTCACGGTGCAGGACTCCACC
MV18   901 TCCCTCAGAGTCAAAATCTTCAACATTCAAGTCAAAGAGGTCACGGTGCAGGACTCCACC
MV20   901 TCCCTCAGAGTCAAAATCTTCAACATTCAAGTCAAAGAGGTCACGGTGCAGGACTCCACC
MV50   901 TCCCTCAGAGTCAAAATCTTCAACATTCAAGTCAAAGAGGTCACGGTGCAGGACTCCACC
MV53   901 TCCCTCAGAGTCAAAATCTTCAACATTCAAGTCAAAGAGGTCACGGTGCAGGACTCCACC

AAV5   961 ACCACCATCGCCAACAACCTCACCTCCACCGTCCAAGTGTTTACGGACGACGACTACCAG
MV1    961 ACCACCATCGCCAACAACCTCACCTCCACCGTCCAAGTGTTTACGGACGACGACTACCAG
MV18   961 ACCACCATCGCCAACAACCTCACCTCCACCGTCCAAGTGTTTACGGACGACGACTACCAG
MV20   961 ACCACCATCGCCAACAACCTCACCTCCACCGTCCAAGTGTTTACGGACGACGACTACCAG
MV50   961 ACCACCATCGCCAACAACCTCACCTCCACCGTCCAAGTGTTTACGGACGACGACTACCAG
MV53   961 ACCACCATCGCCAACAACCTCACCTCCACCGTCCAAGTGTTTACGGACGACGACTACCAG

AAV5  1021 CTGCCCTACGTCGTCGGCAACGGGACCGAGGGATGCCTGCCGGCCTTCCCTCCGCAGGTC
MV1   1021 CTGCCCTACGTCGTCGGCAACGGGACCGAGGGATGCCTGCCGGCCTTCCCTCCGCAGGTC
MV18  1021 CTGCCCTACGTCGTCGGCAACGGGACCGAGGGATGCCTGCCGGCCTTCCCTCCGCAGGTC
MV20  1021 CTGCCCTACGTCGTCGGCAACGGGACCGAGGGATGCCTGCCGGCCTTCCCTCCGCAGGTC
MV50  1021 CTGCCCTACGTCGTCGGCAACGGGACCGAGGGATGCCTGCCGGCCTTCCCTCCGCAGGTC
MV53  1021 CTGCCCTACGTCGTCGGCAACGGGACCGAGGGATGCCTGCCGGCCTTCCCTCCGCAGGTC

AAV5  1081 TTTACGCTGCCGCAGTACGGTTACGCGACGCTGAACCGCGACAACACAGAAAATCCCACC
MV1   1081 TTTACGCTGCCGCAGTACGGTTACGCGACGCTGAACCGCGACAACACAGAAAATCCCACC
MV18  1081 TTTACGCTGCCGCAGTACGGTTACGCGACGCTGAACCGCGACAACACAGAAAATCCCACC
MV20  1081 TTTACGCTGCCGCAGTACGGTTACGCGACGCTGAACCGCGACAACACAGAAAATCCCACC
MV50  1081 TTTACGCTGCCGCAGTACGGTTACGCGACGCTGAACCGCGACAACACAGAGAATCCCACC
MV53  1081 TTTACGCTGCCGCAGTACGGTTACGCGACGCTGAACCGCGACAACACAGAAAATCCCACC

AAV5  1141 GAGAGGAGCAGCTTCTTCTGCCTAGAGTACTTTCCCAGCAAGATGCTGAGAACGGGCAAC
MV1   1141 GAGAGGAGCAGCTTCTTCTGCCTAGAGTACTTTCCCAGCAAGATGCTGAGAACGGGCAAC
MV18  1141 GAGAGGAGCAGCTTCTTCTGCCTAGAGTACTTTCCCAGCAAGATGCTGAGAACGGGCAAC
MV20  1141 GAGAGGAGCAGCTTCTTCTGCCTAGAGTACTTTCCCAGCAAGATGCTGAGAACGGGCAAC
MV50  1141 GAGAGGAGCAGCTTCTTCTGCCTAGAGTACTTTCCCAGCAAGATGCTGAGAACGGGCAAC
MV53  1141 GAGAGGAGCAGCTTCTTCTGCCTAGAGTACTTTCCCAGCAAGATGCTGAGAACGGGCAAC

AAV5  1201 AACTTTGAGTTTACCTACAACTTTGAGGAGGTGCCCTTCCACTCCAGCTTCGCTCCCAGT
MV1   1201 AACTTTGAGTTTACCTACAACTTTGAGGAGGTGCCCTTCCACTCCAGCCTCGCTCCCAGT
MV18  1201 AACTTTGAGTTTACCTACAACTTTGAGGAGGTGCCCTTCCACTCCAGCTTCGCTCCCAGT
MV20  1201 AACTTTGAGTTTACCTACAACTTTGAGGAGGTGCCCTTCCACTCCAGCTTCGCTCCCAGT
MV50  1201 AACTTTGAGTTTACCTACAACTTTGAGGAGGTGCCCTTCCACTCCAGCTTCGCTCCCAGT
MV53  1201 AACTTTGAGTTTACCTACAACTTTGAGGAGGTGCCCTTCCACTCCAGCTTCGCTCCCAGT
```

FIG. 4 (CONT.)

```
AAV5  1261 CAGAACCTGTTCAAGCTGGCCAACCCGCTGGTGGACCAGTACTTGTACCGCTTCGTGAGC
MV1   1261 CAGAACCTCTTCAAGCTGGCCAACCCGCTGGTGGACCAGTACTTGTACCGCTTCGTGAGC
MV18  1261 CAGAACCTGTTCAAGCTGGCCAACCCGCTGGTGGACCAGTACTTGTACCGCTTCGTGAGC
MV20  1261 CAGAACCTCTTCAAGCTGGCCAACCCGCTGGTGGACCAGTACTTGTACCGCTTCGTGAGC
MV50  1261 CAGAACCTGTTCAAGCTGGCCAACCCGCTGGTGGACCAGTACTTGTACCGCTTCGTGAGC
MV53  1261 CAGAACCTGTTCAAGCTGGCCAACCCGCTGGTGGACCAGTACTTGTACCGCTTCGTGAGC

AAV5  1321 ACAAATAACACTGGCGGAGTCCAGTTCAACAAGAACCTGGCCGGGAGATACGCCAACACC
MV1   1321 ACAAATAACACTGGCGGAGTCCAGTTCAACAAGAACCTGGCCGGGAGATACGCCAACACC
MV18  1321 ACAAATAACACTGGCGGAGTCCAGTTCAACAAGAACCTGGCCGGGAGATACGCCAACACC
MV20  1321 ACAAATAACACTGGCGGAGTCCAGTTCAACAAGAACCTGGCCGGGAGATATGCCAACACC
MV50  1321 ACAAATAACACTGGCGGAGTCCAGTTCAACAAGAACCTGGCCGGGAGATACGCCAACACC
MV53  1321 ACAAATAACACTGGCGGAGTCCAGTTCAACAAGAACCTGGCCGGGAGATACGCCAACACC

AAV5  1381 TACAAAAACTGGTTCCCGGGGCCCATGGGCCGAACCCAGGGCTGGAACCTGGGCTCCGGG
MV1   1381 TACAAAAACTGGTTCCCGGGGCCCATGGGCCGAACCCAGGGCTGGAACCTGGGCTCCGGG
MV18  1381 TACAAAAACTGGTTCCCGGGGCCCATGGGCCGAACCCAGGGCTGGAACCTGGGCTCCGGG
MV20  1381 TACAAAAACTGGTTCCCGGGGCCCATAGGCCGAACCCAGGGCTGGAACCTGGGCTCCGGG
MV50  1381 TACAAAAACTGGTTCCCGGGGCCCATGGGCCGAACCCAGGGCTGGAACCTGGGCTCCGGG
MV53  1381 TACAAAAACTGGTTCCCGGGGCCCATGGGCCGAACCCAGGGCTGGAACCTGGGCTCCGGG

AAV5  1441 GTCAACCGCGCCAGTGTCAGCGCCTTCGCCACGACCAATAGGATGGAGCTCGAGGGCGCG
MV1   1441 GTCAACCGCGCCAGTGTCAGCGCCTTCGCCACGACCAATAGGATGGAGCTCGAGGGCGCG
MV18  1441 GTCAACCGCGCCAGTGTCAGCGCCTTCGCCACGACCAATAGGATGGAGCTCGAGGGCGCG
MV20  1441 GTCAACCGCGCCAGTGTCAGCGCCTTCGCCACGACCAATAGGATGGAGCTCGAGGGCGCG
MV50  1441 GTCAACCGCGCCAGTGTCAGCGCCTTCGCCACGACCAATAGGATGGAGCTCGAGGGCGCG
MV53  1441 GTCAACCGCGCCAGTGTCAGCGCCTTCGCCACGACCAATAGGATGGAGCTCGAGGGCGCG

AAV5  1501 AGTTACCAGGTGCCCCCGCAGCCGAACGGCATGACCAACAACCTCCAGGGCAGCAACACC
MV1   1501 AGTTACCAGGTGCCCCCGCAGCCGAACGGCATGACCAACAACCTCCAGGGCAGCAACACC
MV18  1501 AGTTACCAGGTGCCCCCGCAGCCGAACGGCATGACCAACAACCTCCAGGGCAGCAACACC
MV20  1501 AGTTACCAGGTGCCCCCGCAGCCGAACGGCATGACCAACAACCTCCAGGGCAGCAACACC
MV50  1501 AGTTACCAGGTGCCCCCGCAGCCGAACGGCATGACCAACAACCTCCAGGGCAGCAACACC
MV53  1501 AGTTACCAGGTGCCCCCGCAGCCGAACGGCATGACCAACAACCTCCAGGGCAGCAACACC

AAV5  1561 TATGCCCTGGAGAACACTATGATCTTCAACAGCCAGCCGGCGAACCCGGGCACCACCGCC
MV1   1561 TATGCCCTGGAGAACACTATGATCTTCAACAGCCAGCCGGCGAACCCGGGCACCACCGCC
MV18  1561 TATGCCCTGGAGAACACTATGATCTTCAACAGCCAGCCGGCGAACCCGGGCACCACCGCC
MV20  1561 TATGCCCTGGAGAACACTATGATCTTCAACAGCCAGCCGGCGAACCCGGGCACCACCGCC
MV50  1561 TATGCCCTGGAGAACACTATGATCTTCAACAGCCAGCCGGCGAACCCGGGCACCACCGCC
MV53  1561 TATGCCCTGGAGAACACTATGATCTTCAACAGCCAGCCGGCGAACCCGGGCACCACCGCC

AAV5  1621 ACGTACCTCGAGGGCAACATGCTCATCACCAGCGAGAGCGAGACGCAGCCGGTGAACCGC
MV1   1621 ACGTACCTCGAGGGCAACATGCTCATCACCAGCGAGAGCGAGACGCAGCCGGTGAACCGC
MV18  1621 ACGTACCTCGAGGGCAACATGCTCATCACCAGCGAGAGCGAGACGCAGCCGGTGAACCGC
MV20  1621 ACGTACCTCGAGGGCAACATGCTCATCACCAGCGAGAGCGAGACGCAGCCGGTGAACCGC
MV50  1621 ACGTACCTCGAGGGCAACATGCTCATCACCAGCGAGAGCGAGACGCAGCCGGTGAACCGC
MV53  1621 ACGTACCTCGAGGGCAACATGCTCATCACCAGCGAGAGCGAGACGCAGCCGGTGAACCGC
```

*FIG. 4 (CONT.)*

```
AAV5  1681  GTGGCGTACAACGTCGGCGGGCAGATGGCCACCAACAACCAGAGCTCCACCACTGCCCCC
MV1   1681  GTGGCTTACAACGTCGGCGGGCAGATGGCCACCAACAACCAGAGCTCCACCACTGCCCCC
MV18  1681  GTGGCGTACAACGTCGGCGGGCAGATGGCCACCAACAACCAGAGCTCCACCACTGCCCCC
MV20  1681  GTGGCGTACAACGTCGGCGGGCAGATGGCCACCAACAACCAGAGCTCCACCACTACCCCC
MV50  1681  GTGGCGTACAACGTCGGCGGGCAGATGGCCACCAACAACCAGAGCTCCACCACTGCCCCC
MV53  1681  GTGGCGTACAACGTCGGCGGGCAGATGGCCACCAACAACCAGAGCTCCACCACTGCCCCC

AAV5  1741  GCGACCGGCACGTACAACCTCCAGGAAATCGTGCCCGGCAGCGTGTGGATGGAGAGGGAC
MV1   1741  GCGACCGGCACGTACAACCTCCAGGAAATCGTGCCCGGCAGCGTGTGGATGGAGAGGGAC
MV18  1741  GCGACCGGCACGTACAACCTCCAGGAAATCGTGCCCGGCAGCGTGTGGATGGAGAGGGAC
MV20  1741  GCGACCGGCACGTACAACCTCCAGGAAATCGTGCCCGGCAGCGTGTGGATGGAGAGGGAC
MV50  1741  GCGACCGGCACGTACAACCTCCAGGAAATCGTGCCCGGCAGCGTGTGGATGGAGAGGGAC
MV53  1741  GCGACCGGCACGTACAACCTCCAGGAAATCGTGCCCGGCAGCGTGTGGATGGAGAGGGAC

AAV5  1801  GTGTACCTCCAAGGACCCATCTGGGCCAAGATCCCAGAGACGGGGGCGCACTTTCACCCC
MV1   1801  GTGTACCTCCAAGGACCCATCTGGGCCAAGATCCCAGAGACGGGGGCGCACTTTCACCCC
MV18  1801  GTGTACCTCCAAGGACCCATCTGGGCCAAGATCCCAGAGACGGGGGCGCACTTTCACCCC
MV20  1801  GTGTACCTCCAAGGACCCATCTGGGCCAAGATCCCAGAGACGGGGGCGCACTTTCACCCC
MV50  1801  GTGTACCTCCAAGGACCCATCTGGGCCAAGATCCCAGAGACGGGGGCGCACTTTCACCCC
MV53  1801  GTGTACCTCCAAGGACCCATCTGGGCCAAGATCCCAGAGACGGGGGCGCACTTTCACCCC

AAV5  1861  TCTCCGGCCATGGGCGGATTCGGACTCAAACACCCACCGCCCATGATGCTCATCAAGAAC
MV1   1861  TCTCCGGCCATGGGCGGATTCGGACTCAAACACCCACCGCCCATGATGCTCATCAAGAAC
MV18  1861  TCTCCGGCCATGGGCGGATTCGGACTCAAACACCCACCGCCCATGATGCTCATCAAGAAC
MV20  1861  TCTCCGGCCATGGGCGGATTCGGACTCAAACACCCACCGCCCATGATGCTCATCAAGAAC
MV50  1861  TCTCCGGCCATGGGCGGATTCGGACTCAAACACCCACCGCCCATGATGCTCATCAAGAAC
MV53  1861  TCTCCGGCCATGGGCGGATTCGGACTCAAACACCCACCGCCCATGATGCTCATCAAGAAC

AAV5  1921  ACGCCTGTGCCCGGAAATATCACCAGCTTCTCGGACGTGCCCGTCAGCAGCTTCATCACC
MV1   1921  ACGCCTGTGCCCGGAAATATCACCAGCTTCTCGGACGTGCCCGTCAGCAGCTTCATCACC
MV18  1921  ACGCCTGTGCCCGGAAATATCACCAGCTTCTCGGACGTGCCCGTCAGCAGCTTCATCACC
MV20  1921  ACGCCTGTGCCCGGAAATATCACCAGCTTCTCGGACGTGCCCGTCAGCAGCTTCATCACC
MV50  1921  ACGCCTGTGCCCGGAAATATCACCAGCTTCTCGGACGTGCCCGTCAGCAGCTTCATCACC
MV53  1921  ACGCCTGTGCCCGGAAATATCACCAGCTTCTCGGACGTGCCCGTCAGCAGCTTCATCACC

AAV5  1981  CAGTACAGCACCGGGCAGGTCACCGTGGAGATGGAGTGGGAGCTCAAGAAGGAAAACTCC
MV1   1981  CAGTACAGCACCGGGCAGGTCACCGTGGAGATGGAGTGGGAGCTCAAGAAGGAAAACTCC
MV18  1981  CAGTACAGCACCGGGCAGGTCACCGTGGAGATGGAGTGGGAGCTCAAGAAGGAAAACTCC
MV20  1981  CAGTACAGCACCGGGCAGGTCACTGTGGAGATGGAGTGGGAGCTCAAGAAGGAAAACTCC
MV50  1981  CAGTACAGCACCGGGCAGGTCACCGTGGAGATGGAGTGGGAGCTCAAGAAGGAAAACTCC
MV53  1981  CAGTACAGCACCGGGCAGGTCACCGTGGAGATGGAGTGGGAGCTCAAGAAGGAAAACTCC

AAV5  2041  AAGAGGTGGAACCCAGAGATCCAGTACACAAACAACTACAACGACCCCCAGTTTGTGGAC
MV1   2041  AAGAGGTGGAACCCCGAGATCCAGTACACAAACAACTACAACGACCCCCAGTTTGTGGAC
MV18  2041  AAGAGGTGGAACCCAGAGATCCAGTACACAAACAACTACAACGACCCCCAGTTTGTGGAC
MV20  2041  AAGAGGTGGAACCCAGAGATCCAGTACACAAACAACTACAACGACCCCCAGTTTGTGGAC
MV50  2041  AAGAGGTGGAACCCCGAGATCCAGTACACAAACAACTACAACGACCCCCAGTTTGTGGAC
MV53  2041  AAGAGGTGGAACCCAGAGATCCAGTACACAAACAACTACAACGACCCCCAGTTTGTGGAC
```

*FIG. 4 (CONT.)*

```
AAV5  2101  TTTGCCCCGGACAGCACCGGGGAATACAGAACCACCAGACCTATCGGAACCCGATACCTT
MV1   2101  TTTGCCCCGGACAGCACCGGGGAATACAGAAGCACCAGACCTATCGGAACCCGATACCTT
MV18  2101  TTTGCCCCGGACAGCACCGGGGAATACAGAACCACCAGACCTATCGGAACCCGATACCTT
MV20  2101  TTTGCCCCGGACAGCACCGGGGAATACAGAAGCACCAGACCTATCGGAACCCGATACCTT
MV50  2101  TTTGCCCCGGACGGCACCGGGGAATACAGAAGCACCAGACCTATCGGAACCCGATACCTT
MV53  2101  TTTGCCCCGGACAGCACCGGGGAATACAGAACCACCAGACCTATCGGAACCCGATACCTT

AAV5  2161  ACCCGACCCCTTTAA
MV1   2161  ACCCGACCCCTTTAA
MV18  2161  ACCCGACCCCTTTAA
MV20  2161  ACCCGACCCCTTTAA
MV50  2161  ACCCGACCCCTTTAA
MV53  2161  ACCCGACCCCTTTAA
```

FIG. 4 (CONT.)

```
AAV5    1  MSFVDHPPDWLEEVGEGLREFLGLEAGPPKPKPNQQHQDQARGLVLPGYNYLGPGNGLDR
MV1     1  MSFVDHPPDWLEEVGEGLREFLGLEAGPPKPKPNQQHQDQARGLVLPGYNYLGPGNGLDR
MV18    1  MSFVDHPPDWLEEVGEGLREFLGLEAGPPKPKPNQQHQDQARGLVLPGYNYLGPGNGLDR
MV20    1  MSFVDHPPDWLEEVGEGLREFLGLEAGPPKPKPNQQHQDQARGLVLPGYNYLGPGNGLDR
MV50    1  MSFVDHPPDWLEEVGEGLREFLGLEAGPPKPKPNQQHQDQARGLVLPGYNYLGPGNGLDR
MV53    1  MSFVDHPPDWLEEVGEGLREFLGLEAGPPKPKPNQQHQDQARGLVLPGYNYLGPGNGLDR

AAV5   61  GEPVNRADEVAREHDISYNEQLEAGDNPYLKYNHADAEFQEKLADDTSFGGNLGKAVFQA
MV1    61  GEPVNRADEVAREHDISYNEQLEAGDNPYLKYNHADAEFQEKLADDTSFGGNLGKAVFQA
MV18   61  GEPVNRADEVAREHDISYNEQLEAGDNPYLKYNHADAEFQEKLADDTSFGGNLGKAVFQA
MV20   61  GEPVNRADEVAREHDISYNEQLEAGDNPYLKYNHADAEFQEKLADDTSFGGNLGKAVFQA
MV50   61  GEPVNRADEVAREHDISYNEQLEAGDNPYLKYNHADAEFQEKLADDTSFGGNLGKAVFQA
MV53   61  GEPVNRADEVAREHDISYNEQLEAGDNPYLKYNHADAEFQEKLADDTSFGGNLGKAVFQA

AAV5  121  KKRVLEPFGLVEEGAKTAPTGKRIDDHFPKRKKARTEEDSKPSTSSDAEAGPSGSQQLQT
MV1   121  KKRVLEPFGLVEEGAKTAPTGKRIDDHFPKRKKARTEEDSKPSTSSDAEAGPSGSQQLQT
MV18  121  KKRVLEPFGLVEEGAKTAPTGKRIDDHFPKRKKARTEEDSKPSTSSDAEAGPSGSQQLQT
MV20  121  KKRVLEPFGLVEEGAKTAPTGKRIDDHFPKRKKARTEEDSKPSTSSDAEAGPSGSQQLQT
MV50  121  KKRVLEPFGLVEEGAKTAPTGKRIDDHFPKRKKARTEEDSKPSTSSDAEAGPSGSQQLQT
MV53  121  KKRVLEPFGLVEEGAKTAPTGKRIDDHFPKRKKARTEEDSKPSTSSDAEAGPSGSQQLRT

AAV5  181  PAQPASSLGADTMSAGGGGPLGDNNQGADGVGNASGDWHCDSTWMGDRVVTKSTRTWVLP
MV1   181  PAQPASSLGADTMSAGGGGPLGDNNQGADGVGNASGDWHCDSTWMGDRVVTKSTRTWVLP
MV18  181  PAQPASSLGADTMSAGGGGPLGDNNQGADGVGNASGDWHCDSTWMGDRVVTKSTRTWVLP
MV20  181  PAQPASSLGADTMSAGGGGSLGDNNQGADGVGNASGDWHCDSTWMGDRVVTKSTRTWVLP
MV50  181  PAQPASSLGADTMSAGGGGPLGDNNQGADGVGNASGDWHCDSTWMGDRVVTKSTRTWVLP
MV53  181  PAQPASSLGADTMSAGGGGPLGDNNQGADGVGNASGDWHCDSTWMGDRVVTKSTRTWVLP

AAV5  241  SYNNHQYREIKSGSVDGSNANAYFGYSTPWGYFDFNRFHSHWSPRDWQRLINNYWGFRPR
MV1   241  SYNNHQYREIKSGSVDRSNANAYFGYSTPWGYFDFNRFHSHWSPRDWQRLINNYWGFRPR
MV18  241  SYNNHQYREIKSGSVDRSNANAYFGYSTPWGYFDFNRFHSHWSPRDWQRLINNYWGFRPR
MV20  241  SYNNHQYREIKSGSVDGSNANAYFGYSTPWGYFDFNRFHSHWSPRDWQRLINNYWGFRPR
MV50  241  SYNNHQYREIKSGSVDRSNANAYFGYSTPWGYFDFNRFHSHWSPRDWQRLINNYWGFRPR
MV53  241  SYNNHQYREIKSGSVDRSNANAYFGYSTPWGYFDFNRFHSHWSPRDWQRLINNYWGFRPR

AAV5  301  SLRVKIFNIQVKEVTVQDSTTTIANNLTSTVQVFTDDDYQLPYVVGNGTEGCLPAFPPQV
MV1   301  SLRVKIFNIQVKEVTVQDSTTTIANNLTSTVQVFTDDDYQLPYVVGNGTEGCLPAFPPQV
MV18  301  SLRVKIFNIQVKEVTVQDSTTTIANNLTSTVQVFTDDDYQLPYVVGNGTEGCLPAFPPQV
MV20  301  SLRVKIFNIQVKEVTVQDSTTTIANNLTSTVQVFTDDDYQLPYVVGNGTEGCLPAFPPQV
MV50  301  SLRVKIFNIQVKEVTVQDSTTTIANNLTSTVQVFTDDDYQLPYVVGNGTEGCLPAFPPQV
MV53  301  SLRVKIFNIQVKEVTVQDSTTTIANNLTSTVQVFTDDDYQLPYVVGNGTEGCLPAFPPQV

AAV5  361  FTLPQYGYATLNRDNTENPTERSSFFCLEYFPSKMLRTGNNFEFTYNFEEVPFHSSFAPS
MV1   361  FTLPQYGYATLNRDNTENPTERSSFFCLEYFPSKMLRTGNNFEFTYNFEEVPFHSSLAPS
MV18  361  FTLPQYGYATLNRDNTENPTERSSFFCLEYFPSKMLRTGNNFEFTYNFEEVPFHSSFAPS
MV20  361  FTLPQYGYATLNRDNTENPTERSSFFCLEYFPSKMLRTGNNFEFTYNFEEVPFHSSFAPS
MV50  361  FTLPQYGYATLNRDNTENPTERSSFFCLEYFPSKMLRTGNNFEFTYNFEEVPFHSSFAPS
MV53  361  FTLPQYGYATLNRDNTENPTERSSFFCLEYFPSKMLRTGNNFEFTYNFEEVPFHSSFAPS
```

FIG. 5

```
AAV5  421  QNLFKLANPLVDQYLYRFVSTNNTGGVQFNKNLAGRYANTYKNWFPGPMGRTQGWNLGSG
MV1   421  QNLFKLANPLVDQYLYRFVSTNNTGGVQFNKNLAGRYANTYKNWFPGPMGRTQGWNLGSG
MV18  421  QNLFKLANPLVDQYLYRFVSTNNTGGVQFNKNLAGRYANTYKNWFPGPMGRTQGWNLGSG
MV20  421  QNLFKLANPLVDQYLYRFVSTNNTGGVQFNKNLAGRYANTYKNWFPGPIGRTQGWNLGSG
MV50  421  QNLFKLANPLVDQYLYRFVSTNNTGGVQFNKNLAGRYANTYKNWFPGPMGRTQGWNLGSG
MV53  421  QNLFKLANPLVDQYLYRFVSTNNTGGVQFNKNLAGRYANTYKNWFPGPMGRTQGWNLGSG

AAV5  481  VNRASVSAFATTNRMELEGASYQVPPQPNGMTNNLQGSNTYALENTMIFNSQPANPGTTA
MV1   481  VNRASVSAFATTNRMELEGASYQVPPQPNGMTNNLQGSNTYALENTMIFNSQPANPGTTA
MV18  481  VNRASVSAFATTNRMELEGASYQVPPQPNGMTNNLQGSNTYALENTMIFNSQPANPGTTA
MV20  481  VNRASVSAFATTNRMELEGASYQVPPQPNGMTNNLQGSNTYALENTMIFNSQPANPGTTA
MV50  481  VNRASVSAFATTNRMELEGASYQVPPQPNGMTNNLQGSNTYALENTMIFNSQPANPGTTA
MV53  481  VNRASVSAFATTNRMELEGASYQVPPQPNGMTNNLQGSNTYALENTMIFNSQPANPGTTA

AAV5  541  TYLEGNMLITSESETQPVNRVAYNVGGQMATNNQSSTTAPATGTYNLQEIVPGSVWMERD
MV1   541  TYLEGNMLITSESETQPVNRVAYNVGGQMATNNQSSTTAPATGTYNLQEIVPGSVWMERD
MV18  541  TYLEGNMLITSESETQPVNRVAYNVGGQMATNNQSSTTAPATGTYNLQEIVPGSVWMERD
MV20  541  TYLEGNMLITSESETQPVNRVAYNVGGQMATNNQSSTTTPATGTYNLQEIVPGSVWMERD
MV50  541  TYLEGNMLITSESETQPVNRVAYNVGGQMATNNQSSTTAPATGTYNLQEIVPGSVWMERD
MV53  541  TYLEGNMLITSESETQPVNRVAYNVGGQMATNNQSSTTAPATGTYNLQEIVPGSVWMERD

AAV5  601  VYLQGPIWAKIPETGAHFHPSPAMGGFGLKHPPPMMLIKNTPVPGNITSFSDVPVSSFIT
MV1   601  VYLQGPIWAKIPETGAHFHPSPAMGGFGLKHPPPMMLIKNTPVPGNITSFSDVPVSSFIT
MV18  601  VYLQGPIWAKIPETGAHFHPSPAMGGFGLKHPPPMMLIKNTPVPGNITSFSDVPVSSFIT
MV20  601  VYLQGPIWAKIPETGAHFHPSPAMGGFGLKHPPPMMLIKNTPVPGNITSFSDVPVSSFIT
MV50  601  VYLQGPIWAKIPETGAHFHPSPAMGGFGLKHPPPMMLIKNTPVPGNITSFSDVPVSSFIT
MV53  601  VYLQGPIWAKIPETGAHFHPSPAMGGFGLKHPPPMMLIKNTPVPGNITSFSDVPVSSFIT

AAV5  661  QYSTGQVTVEMEWELKKENSKRWNPEIQYTNNYNDPQFVDFAPDSTGEYRTTRPIGTRYL
MV1   661  QYSTGQVTVEMEWELKKENSKRWNPEIQYTNNYNDPQFVDFAPDSTGEYRTTRPIGTRYL
MV18  661  QYSTGQVTVEMEWELKKENSKRWNPEIQYTNNYNDPQFVDFAPDSTGEYRTTRPIGTRYL
MV20  661  QYSTGQVTVEMEWELKKENSKRWNPEIQYTNNYNDPQFVDFAPDSTGEYRTTRPIGTRYL
MV50  661  QYSTGQVTVEMEWELKKENSKRWNPEIQYTNNYNDPQFVDFAPDGTGEYRTTRPIGTRYL
MV53  661  QYSTGQVTVEMEWELKKENSKRWNPEIQYTNNYNDPQFVDFAPDSTGEYRTTRPIGTRYL

AAV5  721  TRPL
MV1   721  TRPL
MV18  721  TRPL
MV20  721  TRPL
MV50  721  TRPL
MV53  721  TRPL
```

*FIG. 5 (CONT.)*

MODIFIED ADENO-ASSOCIATED VIRUS 5 CAPSIDS AND USES THEREOF

STATEMENT OF PRIORITY

This application claims the benefit, under 35 U.S.C. § 119(e), of U.S. Provisional Application No. 63/020,139, filed on May 5, 2020, the entire contents of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-881_ST25.txt, 56,036 bytes in size, generated on Apr. 26, 2021 and filed via EFS-Web, is provided in lieu of a paper copy. This Sequence Listing is hereby incorporated herein by reference into the specification for its disclosures.

FIELD OF THE INVENTION

The present invention is in the field of recombinant adeno-associated virus vectors.

BACKGROUND OF THE INVENTION

Adeno-associated virus (AAV) is a 4.7 kb, single stranded DNA virus whose genome is comprised of two open reading frames, rep and cap, which are flanked by inverted terminal repeats (ITR). The rep gene encodes four rep proteins which are essential for replication and packaging of the viral DNA, and the cap gene encodes three capsid proteins, VP1, VP2, and VP3, that interact to form the capsid at a ratio of 1:1:10. Many serotypes of AAV have been discovered thus far, all with varying tropisms to cells and organs in the human body.

AAV-based gene therapy has progressed substantially over the past few decades resulting in many landmark clinical trials and marked success in treating a variety of genetic diseases. The results of the numerous clinical trials have shown that AAV-based therapy is safe and efficacious. Additionally, AAV based gene therapy is capable of efficient gene delivery and long-lasting gene expression in many organs and tissues in the human body. In particular, AAV-based gene therapy has been shown to be very promising for treatment of liver genetic diseases such as hemophilia due to the ability of multiple AAV serotypes to efficiently infect the liver and provide stable expression of the desired transgene.

Despite the success of AAV-based gene therapy, a variety of problems remain unsolved that prevent the gene therapy platform from achieving its full potential. One problem in particular is the significant prevalence of pre-existing neutralizing antibodies (Nabs) against recombinant AAV (rAAV) capsids in the general human population. An extremely large portion of the human population has been previously exposed to various AAV serotypes and developed neutralizing antibodies that bind to rAAV present in the bloodstream (Boutin et al, Human Gene Therapy 2010). Virus bound by these antibodies are typically neutralized and unable to deliver their therapeutic genes to their target cells. The prevalence of neutralizing factors depends primarily on which serotype of AAV is utilized and its general infectivity; AAV capsids that are more infectious typically have higher prevalence. Most AAV serotypes and variants that are currently used for clinical trials have medium to high prevalence of neutralizing factors in the human population and thus a strict screening process must be employed to filter out patients that do not have pre-existing antibodies against the capsid being utilized. As such, a significant fraction of patients who may require AAV-based therapies cannot receive a potentially lifesaving treatment due to the presence of nAbs. Thus, there is a need for an rAAV vector that can efficiently infect liver cells and have minimal binding to pre-existing neutralizing antibodies to expand the patient population that can receive AAV-based therapies for liver diseases.

The present invention overcomes the mentioned shortcomings of current AAV vectors by providing mutant AAV5 capsids that have increased infectivity of human liver cells while retaining the advantageous low seroreactivity that wild type (wt) AAV5 provides.

SUMMARY OF THE INVENTION

The present invention is based, in part, on the development of modified AAV5 capsid proteins that exhibit increased binding to and/or internalization into human hepatocytes. Equally important, the modified capsid proteins display a level of seroreactivity that is about the same or less than that of wild-type AAV5 capsid protein. The modified capsid proteins can be used advantageously for delivery and expression of proteins or functional nucleic acids in the liver of subjects.

Thus, one aspect of the invention relates to a modified AAV5 capsid protein comprising a G257R mutation relative to wild-type AAV5 capsid protein (SEQ ID NO:12). The capsid protein may further comprise a mutation selected from Q179R, F417L, S705G, or any combination thereof.

Another aspect of the invention relates to a modified AAV5 capsid protein comprising the mutations P200S, M469I, and A579T relative to wild-type AAV5 capsid protein (SEQ ID NO:12).

A further aspect of the invention relates to a nucleic acid encoding the modified AAV5 capsid protein of the invention and a vector, cell, or virus particle comprising the nucleic acid.

Another aspect of the invention relates to an AAV particle comprising an AAV vector genome; and the modified AAV5 capsid protein of the invention, wherein the AAV capsid encapsidates the AAV vector genome.

A further aspect of the invention relates to a method of producing a recombinant AAV particle comprising an AAV capsid, the method comprising providing a cell in vitro with a nucleic acid according to the invention, an AAV rep coding sequence, an AAV vector genome comprising a heterologous nucleic acid, and helper functions for generating a productive AAV infection; and allowing assembly of the recombinant AAV particle comprising the AAV capsid and encapsidating the AAV vector genome.

An additional aspect of the invention relates to a pharmaceutical formulation comprising the modified AAV5 capsid protein, nucleic acid, virus particle, or AAV particle of the invention in a pharmaceutically acceptable carrier.

Another aspect of the invention relates to a method of delivering a nucleic acid of interest to a hepatocyte, the method comprising contacting the cell with the AAV particle of the invention.

A further aspect of the invention relates to a method of delivering a nucleic acid of interest to a hepatocyte in a mammalian subject, the method comprising administering an effective amount of the AAV particle or pharmaceutical formulation of the invention to a mammalian subject.

Another aspect of the invention relates to a method of treating a disorder in a mammalian subject in need thereof, wherein the disorder is treatable by expressing a product in the liver of the subject, the method comprising administering a therapeutically effective amount of the AAV particle or pharmaceutical formulation of the invention to a mammalian subject.

These and other aspects of the invention are set forth in more detail in the description of the invention below.

BRIEF DESCRIPTION OF THE DRAWINGS

FIG. 4 depicts an alignment of VP1-encoding nucleotide sequences of wild-type AAV5 and the AAV5 mutants with the most significant increases in human liver cell transduction (SEQ ID NOS:11, 1, 3, 5, 7, 9). Black highlights with white font indicate changes in the nucleotide sequence compared to wild type AAV5 and the other mutant sequences.

FIG. 5 depicts an alignment of VP1 encoding amino acid sequences of wild type AAV5 and the AAV5 mutants with the most significant increase in human liver cell transduction (SEQ ID NOS:12, 2, 4, 6, 8, 10). Black highlights with white font indicate changes in the amino acid sequence compared to wild type AAV5 and other mutant sequences.

FIG. 7A depicts overall values for the quantification of GFP expression in Huh7 cells while FIG. 7B shows the fold increase in GFP expression of the AAV5 mutants versus wild type AAV5.

FIG. 9A depicts overall values for the quantification of GFP expression in HepG2 cells while FIG. 9B shows the fold increase in GFP expression of the AAV5 mutants versus wild type AAV5.

DETAILED DESCRIPTION OF THE INVENTION

Figure 1:
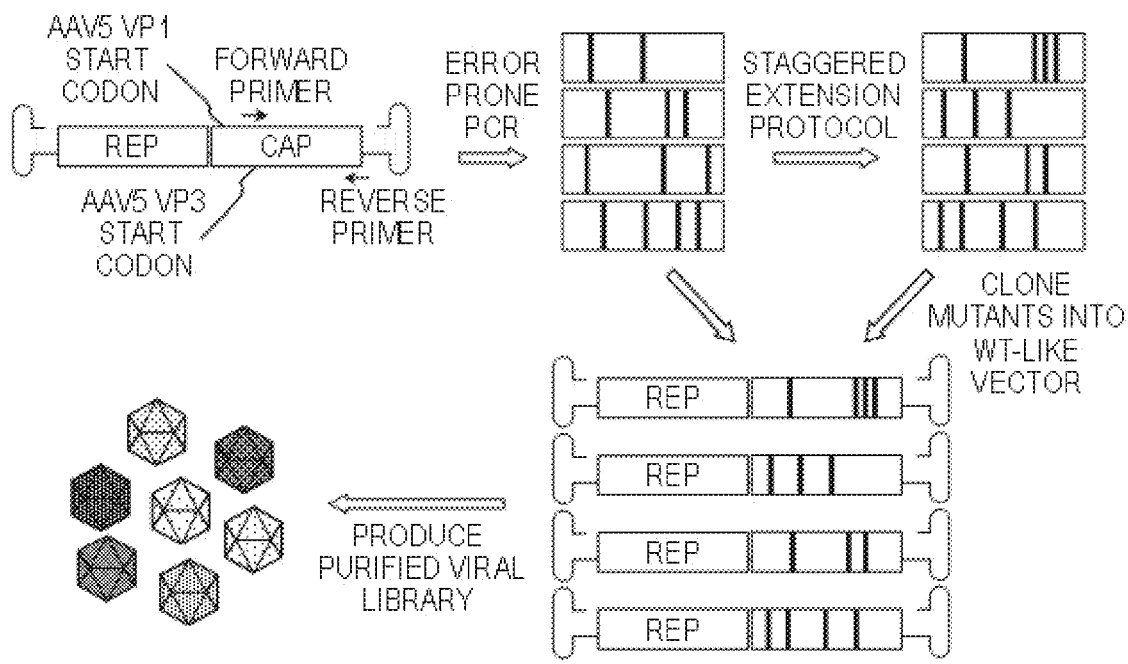
FIG. 1 depicts use of error prone PCR and staggered extension protocol to randomly mutate AAV5 and generate an AAV5 mutant library.

The present invention is based, in part, on the development of synthetic AAV capsid sequences that are capable of transducing hepatocytes in vivo and in vitro. The synthetic capsids can be used to create AAV vectors for use in research or therapeutic applications where liver-specific gene transfer is desired without extensive vector biodistribution to other organs.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 4th Ed. (Cold Spring Harbor, NY, 2013); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consisting essentially of" as used herein in connection with a nucleic acid, protein or capsid structure means that the nucleic acid, protein or capsid structure does not contain any element other than the recited element(s) that significantly alters (e.g., more than about 1%, 5% or 10%) the function of interest of the nucleic acid, protein or capsid structure, e.g., tropism profile of the protein or capsid or a protein or capsid encoded by the nucleic acid.

The designation of all amino acid positions in the AAV capsid subunits in the description of the invention and the appended claims is with respect to VP1 capsid subunit numbering.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) *J. Virol.* 78:6381-6388 and Table 1), which are also encompassed by the term "AAV."

The genomic sequences of various AAV and autonomous parvoviruses, as well as the sequences of the ITRs, Rep proteins, and capsid subunits are known in the art. Such sequences may be found in the literature or in public databases such as the GenBank® database. See, e.g., GenBank® Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivistava et al., (1983) *J. Virol.* 45:555; Chiorini et al., (1998) *J. Virol.* 71:6823; Chiorini et al., (1999) *J. Virol.* 73:1309; Bantel-Schaal et al., (1999) *J. Virol.* 73:939; Xiao et al., (1999) *J. Virol.* 73:3994; Muramatsu et al., (1996) *Virology* 221:208; Shade et al., (1986) *J. Virol.* 58:921; Gao et al., (2002) *Proc. Nat. Acad. Sci. USA* 99:11854; international patent publications WO 00/28061, WO 99/61601, WO 98/11244; U.S. Pat. No. 6,156,303; the disclosures of which are incorporated herein in their entirety. See also Table 1. An early description of the AAV1, AAV2 and AAV3 terminal repeat sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

A "chimeric" AAV nucleic acid capsid coding sequence or AAV capsid protein is one that combines portions of two or more capsid sequences. A "chimeric" AAV virion or particle comprises a chimeric AAV capsid protein.

from the viral genome may be from a stably integrated provirus and/or from a non-integrated episome, as well as any other form which the virus nucleic acid may take within the cell.

TABLE 1

AAV Genomes

| AAV Serotypes/ Isolates | GenBank Accession Number | AAV Serotypes/ Isolates | GenBank Accession Number | AAV Serotypes/ Isolates | GenBank Accession Number |
| --- | --- | --- | --- | --- | --- |
| Clonal Isolates | | Hu S17 | AY695376 | Cy3 | AY243019 |
| Avian AAV ATCC VR-865 | AY186198, AY629583, NC_004828 | Hu T88 | AY695375 | Cy5 | AY243017 |
| | | Hu T71 | AY695374 | Rh13 | AY243013 |
| | | Hu T70 | AY695373 | Clade E | |
| Avian AAV strain DA-1 | NC_006263, AY629583 | Hu T40 | AY695372 | Rh38 | AY530558 |
| | | Hu T32 | AY695371 | Hu66 | AY530626 |
| Bovine AAV | NC_005889, AY388617 | Hu T17 | AY695370 | Hu42 | AY530605 |
| | | Hu LG15 | AY695377 | Hu67 | AY530627 |
| AAV4 | NC_001829 | Clade C | | Hu40 | AY530603 |
| AAV5 | AY18065, AF085716 | AAV3 | NC_001729 | Hu41 | AY530604 |
| | | AAV3B | NC_001863 | Hu37 | AY530600 |
| Rh34 | AY243001 | Hu9 | AY530629 | Rh40 | AY530559 |
| Rh33 | AY243002 | Hu10 | AY530576 | Rh2 | AY243007 |
| Rh32 | AY243003 | Hu11 | AY530577 | Bb1 | AY243023 |
| AAV10 | AY631965 | Hu53 | AY530615 | Bb2 | AY243022 |
| AAV11 | AY631966 | Hu55 | AY530617 | Rh10 | AY243015 |
| AAV12 | DQ813647 | Hu54 | AY530616 | Hu17 | AY530582 |
| AAV13 | EU285562 | Hu7 | AY530628 | Hu6 | AY530621 |
| Clade A | | Hu18 | AY530583 | Rh25 | AY530557 |
| AAV1 | NC_002077, AF063497 | Hu15 | AY530580 | Pi2 | AY530554 |
| | | Hu16 | AY530581 | Pi1 | AY530553 |
| AAV6 | NC_001862 | Hu25 | AY530591 | Pi3 | AY530555 |
| Hu.48 | AY530611 | Hu60 | AY530622 | Rh57 | AY530569 |
| Hu 43 | AY530606 | Ch5 | AY243021 | Rh50 | AY530563 |
| Hu 44 | AY530607 | Hu3 | AY530595 | Rh49 | AY530562 |
| Hu 46 | AY530609 | Hu1 | AY530575 | Hu39 | AY530601 |
| Clade B | | Hu4 | AY530602 | Rh58 | AY530570 |
| Hu19 | AY530584 | Hu2 | AY530585 | Rh61 | AY530572 |
| Hu20 | AY530586 | Hu61 | AY530623 | Rh52 | AY530565 |
| Hu23 | AY530589 | Clade D | | Rh53 | AY530566 |
| Hu22 | AY530588 | Rh62 | AY530573 | Rh51 | AY530564 |
| Hu24 | AY530590 | Rh48 | AY530561 | Rh64 | AY530574 |
| Hu21 | AY530587 | Rh54 | AY530567 | Rh43 | AY530560 |
| Hu27 | AY530592 | Rh55 | AY530568 | AAV8 | AF513852 |
| Hu28 | AY530593 | Cy2 | AY243020 | Rh8 | AY242997 |
| Hu29 | AY530594 | AAV7 | AF513851 | Rh1 | AY530556 |
| Hu63 | AY530624 | Rh35 | AY243000 | Clade F | |
| Hu64 | AY530625 | Rh37 | AY242998 | AAV9 (Hu14) | AY530579 |
| Hu13 | AY530578 | Rh36 | AY242999 | Hu31 | AY530596 |
| Hu56 | AY530618 | Cy6 | AY243016 | Hu32 | AY530597 |
| Hu57 | AY530619 | Cy4 | AY243018 | | |
| Hu49 | AY530612 | | | | |
| Hu58 | AY530620 | | | | |
| Hu34 | AY530598 | | | | |
| Hu35 | AY530599 | | | | |
| AAV2 | NC_001401 | | | | |
| Hu45 | AY530608 | | | | |
| Hu47 | AY530610 | | | | |
| Hu51 | AY530613 | | | | |
| Hu52 | AY530614 | | | | |
| Hu T41 | AY695378 | | | | |

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression The term "tropism profile" refers to the pattern of transduction of one or more target cells, tissues and/or organs. Representative examples of synthetic AAV capsids have a tropism profile characterized by efficient transduction of cells of the liver with only low transduction of other organs.

The term "specific for hepatocytes" as used herein refers to a viral vector that, when administered in vivo, preferentially transduces hepatocytes with minimal transduction of cells outside the liver. In some embodiments, at least about 80% of the transduced cells are hepatocytes, e.g., at least about 85%, 90%, 95%, 96%, 97%, 98%, 99% or more hepatocytes.

The term "disorder is treatable by expressing a product in the liver" as used herein refers to a disease, disorder, or injury in which expression of a product (e.g., a protein or polynucleotide) in the liver provides an effective treatment or prevention of the disorder.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) tissues outside the liver, e.g., muscle, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., hepatocytes).

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder.

As used herein, the term "prevent," "prevents," or "prevention" (and grammatical equivalents thereof) refers to a delay in the onset of a disease or disorder or the lessening of symptoms upon onset of the disease or disorder. The terms are not meant to imply complete abolition of disease and encompasses any type of prophylactic treatment that reduces the incidence of the condition or delays the onset and/or progression of the condition.

An "effective" or "therapeutically effective" amount as used herein is an amount that is sufficient to provide some improvement or benefit to the subject. Alternatively stated, an "effective" or "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "heterologous nucleotide sequence" or "heterologous nucleic acid" is a sequence that is not naturally occurring in the virus. Generally, the heterologous nucleic acid or nucleotide sequence comprises an open reading frame that encodes a polypeptide and/or a nontranslated RNA.

A "therapeutic polypeptide" can be a polypeptide that can alleviate or reduce symptoms that result from an absence or defect in a protein in a cell or subject. In addition, a "therapeutic polypeptide" can be a polypeptide that otherwise confers a benefit to a subject, e.g., anti-cancer effects or improvement in transplant survivability.

As used herein, the term "vector," "virus vector," "delivery vector" (and similar terms) generally refers to a virus particle that functions as a nucleic acid delivery vehicle, and which comprises the viral nucleic acid (i.e., the vector genome) packaged within the virion. Virus vectors according to the present invention comprise a synthetic AAV capsid according to the invention and can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) Curr. Topics Microbiol. Immunol. 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

The AAV capsid structure is described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

Modified AAV5 Capsid Proteins

The inventors have identified modified AAV5 capsid proteins capable of providing enhanced transduction of human and other mammalian hepatocytes in vivo and in vitro with similar or lower seroreactivity than wild-type AAV5 capsid protein. Thus, one aspect of the invention relates to modified AAV5 capsid protein comprising a G257R mutation relative to wild-type AAV5 capsid protein having the amino acid sequence of SEQ ID NO:12. The G257R modified AAV5 capsid has the amino acid sequence of SEQ ID NO:4.

In some embodiments, the modified AAV5 capsid protein further comprises a mutation selected from Q179R, F417L, S705G, or any combination thereof. In one embodiment, the modified AAV5 capsid protein comprises the mutations G257R and Q179R (SEQ ID NO:10). In one embodiment, the modified AAV5 capsid protein comprises the mutations G257R and F417L (SEQ ID NO:2). In one embodiment, the modified AAV5 capsid protein comprises the mutations G257R and S705G (SEQ ID NO:8).

Another aspect of the invention relates to a modified AAV5 capsid protein comprising the mutations P200S, M469I, and A579T relative to wild-type AAV5 capsid protein having the amino acid sequence of SEQ ID NO:12. This modified AAV5 capsid has the amino acid sequence of SEQ ID NO:6.

In some embodiments, the modified AAV5 capsid protein comprises, consists essentially of, or consists of an amino acid sequence at least 90% identical to the amino acid sequence of any one of SEQ ID NOS:2, 4, 6, 8, or 10, e.g., at least 91%, 92%, 93%, 94%, 95%, 96%, 97%, 98%, 99%, 99.5% identical. In some embodiments, the modified AAV5 capsid protein comprises, consists essentially of, or consists of the amino acid sequence of any one of SEQ ID NOS:2, 4, 6, 8, or 10.

In some embodiments, the modified AAV5 capsid protein comprises, consists essentially of, or consists of an amino acid sequence as shown in any one of SEQ ID NOS: 2, 4, 6, 8, or 10, wherein 1, 2 or fewer, 3 or fewer, 4 or fewer, 5 or fewer, 6 or fewer, 7 or fewer, 8 or fewer, 9 or fewer, 10 or fewer, 12 or fewer, 15 or fewer, 20 or fewer, 25 or fewer, 30 or fewer, 40 or fewer, or 50 or fewer of the amino acids is substituted by another amino acid (naturally occurring, modified and/or synthetic), optionally a conservative amino acid substitution, and/or 1, 2 or fewer, 3 or fewer, 4 or fewer, 5 or fewer, 6 or fewer, 7 or fewer, 8 or fewer, 9 or fewer, 10 or fewer, 12 or fewer, 15 or fewer, 20 or fewer, 25 or fewer, 30 or fewer, 40 or fewer, or 50 or fewer of the amino acids is deleted and/or there are insertions (including N-terminal and C-terminal extensions) of 1, 2 or fewer, 3 or fewer, 4 or fewer, 5 or fewer, 6 or fewer, 7 or fewer, 8 or fewer, 9 or fewer, 10 or fewer, 12 or fewer, 15 or fewer, 20 or fewer, 25 or fewer, 30 or fewer, 40 or fewer, or 50 or fewer amino acids or any combination of substitutions, deletions and/or insertions, wherein the substitutions, deletions and/or insertions do not unduly impair the structure and/or function of a virion (e.g., an AAV virion) comprising the variant capsid protein or capsid. For example, in representative embodiments of the invention, an AAV virion comprising the modified AAV5 capsid protein substantially retains at least one property of a synthetic virion comprising a modified AAV5 capsid protein as shown in SEQ ID NOS:2, 4, 6, 8, or 10. For example, the virion comprising the modified AAV5 capsid protein can substantially retain the liver tropism profile of a virion comprising the modified AAV5 AAV capsid protein as shown in SEQ ID NOS: 2, 4, 6, 8, or 10. Methods of evaluating biological properties such as virus transduction are well-known in the art (see, e.g., the Examples).

The designation of all amino acid positions in the description of the invention and the appended claims is with respect to VP1 numbering. Those skilled in the art will understand that the AAV capsid generally contains the smaller VP2 and VP3 capsid proteins as well. Due to the overlap of the coding sequences for the AAV capsid proteins, the nucleic acid coding sequences and amino acid sequences of the VP2 and VP3 capsid proteins will be apparent from the VP1 sequences shown in the disclosed sequences. In certain embodiments, isolated VP2 and VP3 capsid proteins comprising the sequences of the invention and isolated nucleic acids encoding the VP2 or VP3 proteins, or both, are contemplated. Also contemplated are chimeric capsid proteins comprising the VP2 or VP3 sequences of the invention.

Conservative amino acid substitutions are known in the art. In particular embodiments, a conservative amino acid substitution includes substitutions within one or more of the following groups: glycine, alanine; valine, isoleucine, leucine; aspartic acid, glutamic acid; asparagine, glutamine; serine, threonine; lysine, arginine; and/or phenylalanine, tyrosine.

It will be apparent to those skilled in the art that the amino acid sequences of the modified AAV5 AAV capsid protein of SEQ ID NOS: 2, 4, 6, 8, or 10 can further be modified to incorporate other modifications as known in the art to impart desired properties. As nonlimiting possibilities, the capsid protein can be modified to incorporate targeting sequences (e.g., RGD) or sequences that facilitate purification and/or detection. For example, the capsid protein can be fused to all or a portion of glutathione-S-transferase, maltose-binding protein, a heparin/heparan sulfate binding domain, poly-His, a ligand, and/or a reporter protein (e.g., Green Fluorescent Protein, β-glucuronidase, β-galactosidase, luciferase, etc.), an immunoglobulin Fc fragment, a single-chain antibody, hemagglutinin, c-myc, FLAG epitope, and the like to form a fusion protein. Methods of inserting targeting peptides into the AAV capsid are known in the art (see, e.g., international patent publication WO 00/28004; Nicklin et al., (2001) *Mol. Ther.* 474-181; White et al., (2004) *Circulation* 109:513-319; Muller et al., (2003) *Nature Biotech.* 21:1040-1046.

The viruses of the invention can further comprise a duplexed viral genome as described in international patent publication WO 01/92551 and U.S. Pat. No. 7,465,583.

The invention also provides AAV capsids comprising the modified AAV5 capsid proteins of the invention and virus particles (i.e., virions) comprising the same, wherein the virus particle packages (i.e., encapsidates) a vector genome, optionally an AAV vector genome. In particular embodiments, the invention provides an AAV particle comprising an AAV capsid comprising an AAV capsid protein of the invention, wherein the AAV capsid packages an AAV vector genome. The invention also provides an AAV particle comprising an AAV capsid or AAV capsid protein encoded by the synthetic nucleic acid capsid coding sequences of the invention.

In particular embodiments, the virion is a recombinant vector comprising a heterologous nucleic acid of interest, e.g., for delivery to a cell. Thus, the present invention is useful for the delivery of nucleic acids to cells in vitro, ex vivo, and in vivo. In representative embodiments, the recombinant vector of the invention can be advantageously employed to deliver or transfer nucleic acids to animal (e.g., mammalian) cells.

Any heterologous nucleotide sequence(s) may be delivered by a virus vector of the present invention. Nucleic acids of interest include nucleic acids encoding polypeptides, optionally therapeutic (e.g., for medical or veterinary uses) and/or immunogenic (e.g., for vaccines) polypeptides.

Therapeutic polypeptides include, but are not limited to, cystic fibrosis transmembrane regulator protein (CFTR), dystrophin (including the protein product of dystrophin mini-genes or micro-genes, see, e.g., Vincent et al., (1993) *Nature Genetics* 5:130; U.S. Patent Publication No. 2003017131; Wang et al., (2000) *Proc. Natl. Acad. Sci. USA* 97:13714-9 [mini-dystrophin]; Harper et al., (2002) *Nature Med.* 8:253-61 [micro-dystrophin]); mini-agrin, a laminin-α2, a sarcoglycan (α, β, γ or δ), Fukutin-related protein, myostatin pro-peptide, follistatin, dominant negative myostatin, an angiogenic factor (e.g., VEGF, angiopoietin-1 or 2), an anti-apoptotic factor (e.g., heme-oxygenase-1, TGF-β, inhibitors of pro-apoptotic signals such as caspases, proteases, kinases, death receptors [e.g., CD-095], modulators of cytochrome C release, inhibitors of mitochondrial pore opening and swelling); activin type II soluble receptor, anti-inflammatory polypeptides such as the Ikappa B dominant mutant, sarcospan, utrophin, mini-utrophin, antibodies or antibody fragments against myostatin or myostatin pro-peptide, cell cycle modulators, Rho kinase modulators such as Cethrin, which is a modified bacterial C3 exoenzyme [available from BioAxone Therapeutics, Inc., Saint-Lauren, Quebec, Canada], BCL-xL, BCL2, XIAP, FLICEc-s, dominant-negative caspase-8, dominant negative caspase-9, SPI-6 (see, e.g., U.S. Patent Application No. 20070026076), transcriptional factor PGC-α1, Pinch gene, ILK gene and thymosin β4 gene), clotting factors (e.g., Factor VIII, Factor IX, Factor X, etc.), erythropoietin, angiostatin, endostatin, catalase, tyrosine hydroxylase, an intracellular and/or extracellular superoxide dismutase, leptin, the LDL receptor, neprilysin, lipoprotein lipase, ornithine transcarbamylase, β-globin, α-globin, spectrin, $\alpha_1$-antitrypsin, methyl cytosine binding protein 2, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, a cytokine (e.g., α-interferon, β-interferon, interferon-γ, interleukins-1 through -14, granulocyte-macrophage colony stimulating factor, lymphotoxin, and the like), peptide growth factors, neurotrophic factors and hormones (e.g., somatotropin, insulin, insulin-like growth factors including IGF-1 and IGF-2, GLP-1, platelet derived growth factor, epidermal growth factor, fibroblast growth factor, nerve growth factor, neurotrophic factor-3 and -4, brain-derived neurotrophic factor, glial derived growth factor, transforming growth factor-α and -β, and the like), bone morphogenic proteins (including RANKL and VEGF), a lysosomal protein, a glutamate receptor, a lymphokine, soluble CD4, an Fc receptor, a T cell receptor, ApoE, ApoC, inhibitor 1 of protein phosphatase inhibitor 1 (I-1), phospholamban, serca2a, lysosomal acid α-glucosidase, α-galactosidase A, Barkct, β2-adrenergic receptor, β2-adrenergic receptor kinase (BARK), phosphoinositide-3 kinase (PI3 kinase), calsarcin, a receptor (e.g., the tumor necrosis growth factor-α soluble receptor), an anti-inflammatory factor such as IRAP, Pim-1, PGC-1α, SOD-1, SOD-2, ECF-SOD, kallikrein, thymosin-β4, hypoxia-inducible transcription factor [HIF], an angiogenic factor, S100A1, parvalbumin, adenylyl cyclase type 6, a molecule that effects G-protein coupled receptor kinase type 2 knockdown such as a truncated constitutively active bARKct; phospholamban inhibitory or dominant-negative molecules such as phospholamban S16E, a monoclonal antibody (including single chain monoclonal antibodies) or a suicide gene product (e.g., thymidine kinase, cytosine deaminase, diphtheria toxin, and tumor necrosis factors such as TNF-α), and any other polypeptide that has a therapeutic effect in a subject in need thereof.

Heterologous nucleotide sequences encoding polypeptides include those encoding reporter polypeptides (e.g., an enzyme). Reporter polypeptides are known in the art and include, but are not limited to, a fluorescent protein (e.g., EGFP, GFP, RFP, BFP, YFP, or dsRED2), an enzyme that produces a detectable product, such as luciferase (e.g., from *Gaussia, Renilla*, or *Photinus*), β-galactosidase, β-glucuronidase, alkaline phosphatase, and chloramphenicol acetyltransferase gene, or proteins that can be directly detected. Virtually any protein can be directly detected by using, for example, specific antibodies to the protein. Additional markers (and associated antibiotics) that are suitable for either positive or negative selection of eukaryotic cells are disclosed in Sambrook and Russell (2001), *Molecular Cloning*, 3rd Ed., Cold Spring Harbor Laboratory Press, Cold Spring Harbor, N.Y., and Ausubel et al. (1992), *Current Protocols in Molecular Biology*, John Wiley & Sons, including periodic updates.

Alternatively, the heterologous nucleic acid may encode a functional RNA, e.g., an antisense oligonucleotide, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including small interfering RNAs (siRNA) that mediate gene silencing (see, Sharp et al., (2000) *Science* 287:2431), microRNA, or other non-translated "functional" RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi or antisense RNA against the multiple drug resistance (MDR) gene product (e.g., to treat tumors and/or for administration to the heart to prevent damage by chemotherapy), RNAi or antisense RNA against myostatin (Duchenne or Becker muscular dystrophy), RNAi or antisense RNA against VEGF or a tumor immunogen including but not limited to those tumor immunogens specifically described herein (to treat tumors), RNAi or antisense oligonucleotides targeting mutated dystrophins (Duchenne or Becker muscular dystrophy), RNAi or antisense RNA against the hepatitis B surface antigen gene (to prevent and/or treat hepatitis B infection), RNAi or antisense RNA against the HIV tat and/or rev genes (to prevent and/or treat HIV) and/or RNAi or antisense RNA against any other immunogen from a pathogen (to protect a subject from the pathogen) or a defective gene product (to prevent or treat disease). RNAi or antisense RNA against the targets described above or any other target can also be employed as a research reagent.

As is known in the art, anti-sense nucleic acids (e.g., DNA or RNA) and inhibitory RNA (e.g., microRNA and RNAi such as siRNA or shRNA) sequences can be used to induce "exon skipping" in patients with muscular dystrophy arising from defects in the dystrophin gene. Thus, the heterologous nucleic acid can encode an antisense nucleic acid or inhibitory RNA that induces appropriate exon skipping. Those skilled in the art will appreciate that the particular approach to exon skipping depends upon the nature of the underlying defect in the dystrophin gene, and numerous such strategies are known in the art. Exemplary antisense nucleic acids and inhibitory RNA sequences target the upstream branch point and/or downstream donor splice site and/or internal splicing enhancer sequence of one or more of the dystrophin exons (e.g., exons 19 or 23). For example, in particular embodiments, the heterologous nucleic acid encodes an antisense nucleic acid or inhibitory RNA directed against the upstream branch point and downstream splice donor site of exon 19 or 23 of the dystrophin gene. Such sequences can be incorporated into an AAV vector delivering a modified U7 snRNA and the antisense nucleic acid or inhibitory RNA (see, e.g., Goyenvalle et al., (2004) Science 306:1796-1799). As another strategy, a modified U1 snRNA can be incorporated into an AAV vector along with siRNA, microRNA or antisense RNA complementary to the upstream and downstream splice sites of a dystrophin exon (e.g., exon 19 or 23) (see, e.g., Denti et al., (2006) Proc. Nat. Acad. Sci. USA 103: 3758-3763). Further, antisense nucleic acids and inhibitory RNA can target the splicing enhancer sequences within exons 19, 43, 45 or 53 (see, e.g., U.S. Pat. Nos. 6,653,467; 6,727,355; and 6,653,466).

The recombinant virus vector may also comprise a heterologous nucleotide sequence that shares homology with and recombines with a locus on the host chromosome. This approach may be utilized to correct a genetic defect in the host cell.

The present invention also provides recombinant virus vectors that express an immunogenic polypeptide, e.g., for vaccination. The heterologous nucleic acid may encode any immunogen of interest known in the art including, but are not limited to, immunogens from human immunodeficiency virus, influenza virus, gag proteins, tumor antigens, cancer antigens, bacterial antigens, viral antigens, and the like. Alternatively, the immunogen can be presented in the virus capsid (e.g., incorporated therein) or tethered to the virus capsid (e.g., by covalent modification).

The use of parvoviruses as vaccines is known in the art (see, e.g., Miyamura et al., (1994) Proc. Nat. Acad. Sci. USA 91:8507; U.S. Pat. No. 5,916,563 to Young et al., U.S. Pat. No. 5,905,040 to Mazzara et al., U.S. Pat. Nos. 5,882,652, 5,863,541 to Samulski et al.; the disclosures of which are incorporated herein in their entireties by reference). The antigen may be presented in the virus capsid. Alternatively, the antigen may be expressed from a heterologous nucleic acid introduced into a recombinant vector genome.

An immunogenic polypeptide, or immunogen, may be any polypeptide suitable for protecting the subject against a disease, including but not limited to microbial, bacterial, protozoal, parasitic, fungal and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen, or a severe acute respiratory syndrome (SARS) immunogen such as a S [S1 or S2], M, E, or N protein or an immunogenic fragment thereof). The immunogen may further be a polio immunogen, herpes immunogen (e.g., CMV, EBV, HSV immunogens) mumps immunogen, measles immunogen, rubella immunogen, diphtheria toxin or other diphtheria immunogen, pertussis antigen, hepatitis (e.g., hepatitis A, hepatitis B or hepatitis C) immunogen, or any other vaccine immunogen known in the art.

Alternatively, the immunogen may be any tumor or cancer cell antigen. Optionally, the tumor or cancer antigen is expressed on the surface of the cancer cell. Exemplary cancer and tumor cell antigens are described in S. A. Rosenberg, (1999) Immunity 10:281). Illustrative cancer and tumor antigens include, but are not limited to: BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) Proc. Natl. Acad. Sci. USA 91:3515; Kawakami et al., (1994) J. Exp. Med., 180:347; Kawakami et al., (1994) Cancer Res. 54:3124) including MART-1 (Coulie et al., (1991) J. Exp. Med. 180:35), gp100 (Wick et al., (1988) J. Cutan. Pathol. 4:201) and MAGE antigen (MAGE-1, MAGE-2 and MAGE-3) (Van der Bruggen et al., (1991) Science, 254: 1643), CEA, TRP-1; TRP-2; P-15 and tyrosinase (Brichard et al., (1993) J. Exp. Med. 178:489); HER-2/neu gene product (U.S. Pat. No. 4,968,603); CA 125; HE4; LK26; FB5 (endosialin); TAG 72; AFP; CA19-9; NSE; DU-PAN-2; CA50; Span-1; CA72-4; HCG; STN (sialyl Tn antigen); c-erbB-2 proteins; PSA; L-CanAg; estrogen receptor; milk fat globulin; p53 tumor suppressor protein (Levine, (1993) Ann. Rev. Biochem. 62:623); mucin antigens (international patent publication WO 90/05142); telomerases; nuclear matrix proteins; prostatic acid phosphatase; papilloma virus antigens; and antigens associated with the following cancers: melanomas, adenocarcinoma, thymoma, sarcoma, lung cancer, liver cancer, colorectal cancer, non-Hodgkin's lymphoma, Hodgkin's lymphoma, leukemias, uterine cancer, breast cancer, prostate cancer, ovarian cancer, cervical cancer, bladder cancer, kidney cancer, pancreatic cancer, brain cancer, kidney cancer, stomach cancer, esophageal cancer, head and neck cancer and others (see, e.g., Rosenberg, (1996) Annu. Rev. Med. 47:481-91).

Alternatively, the heterologous nucleotide sequence may encode any polypeptide that is desirably produced in a cell in vitro, ex vivo, or in vivo. For example, the virus vectors may be introduced into cultured cells and the expressed protein product isolated therefrom.

It will be understood by those skilled in the art that the heterologous nucleic acid(s) of interest may be operably associated with appropriate control sequences. For example, the heterologous nucleic acid may be operably associated with expression control elements, such as transcription/translation control signals, origins of replication, polyadenylation signals, internal ribosome entry sites (IRES), promoters, enhancers, and the like.

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be an RNA polymerase II-based promoter or an RNA polymerase III-based promoter. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. In one embodiment, a hepatocyte-specific or hepatocyte-preferred promoter is used. Examples of hepatocyte-specific or preferred promoters include, without limitation, apolipoprotein AII, albumin, alpha 1-antitrypsin, thyroxine-binding globulin, cytochrome P450 CYP3A4, or microRNA122 or a synthetic liver-specific regulatory sequence. Use of a hepatocyte-specific or preferred promoter can increase the specificity achieved by the synthetic AAV vector by further limiting expression of the heterologous nucleic acid to the liver. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

The invention also provides synthetic AAV particles comprising an AAV capsid and an AAV genome, wherein the AAV genome "corresponds to" (i.e., encodes) the AAV capsid. Also provided are collections or libraries of such chimeric AAV particles, wherein the collection or library comprises 2 or more, 10 or more, 50 or more, 100 or more, 1000 or more, $10^4$ or more, $10^5$ or more, or $10^6$ or more distinct sequences.

The present invention further encompasses "empty" capsid particles (i.e., in the absence of a vector genome) comprising, consisting of, or consisting essentially of the modified AAV5 capsid proteins of the invention. The synthetic AAV capsids of the invention can be used as "capsid vehicles," as has been described in U.S. Pat. No. 5,863,541. Molecules that can be covalently linked, bound to or packaged by the virus capsids and transferred into a cell include DNA, RNA, a lipid, a carbohydrate, a polypeptide, a small organic molecule, or combinations of the same. Further, molecules can be associated with (e.g., "tethered to") the outside of the virus capsid for transfer of the molecules into host target cells. In one embodiment of the invention the molecule is covalently linked (i.e., conjugated or chemically coupled) to the capsid proteins. Methods of covalently linking molecules are known by those skilled in the art.

The virus capsids of the invention also find use in raising antibodies against the novel capsid structures. As a further alternative, an exogenous amino acid sequence may be inserted into the virus capsid for antigen presentation to a cell, e.g., for administration to a subject to produce an immune response to the exogenous amino acid sequence.

The invention also provides nucleic acids (e.g., isolated nucleic acids) encoding the modified AAV5 capsid proteins of the invention. Further provided are vectors comprising the nucleic acids, and cells (in vivo or in culture) comprising the nucleic acids and/or vectors of the invention. Such nucleic acids, vectors and cells can be used, for example, as reagents (e.g., helper constructs or packaging cells) for the production of virus vectors as described herein.

In exemplary embodiments, the invention provides nucleic acid sequences encoding the modified AAV5 capsid of SEQ ID NOS:2, 4, 6, 8, or 10 or an amino acid sequence at least 90% identical thereto. In some embodiments, the nucleic acid comprises, consists essentially of, or consists of a nucleotide sequence at least 90% identical to the nucleotide sequence of any one of SEQ ID NOS:1, 3, 5, 7, or 9, e.g., at least 91%, 92%, 93%, 94%, 95%, 96%, 97%, 98%, 99%, 99.5% identical. In some embodiments, the nucleic acid comprises, consists essentially of, or consists of the nucleotide sequence of any one of SEQ ID NOS:1, 3, 5, 7, or 9. The invention also provides nucleic acids encoding the capsid protein variants and fusion proteins as described above. In particular embodiments, the nucleic acid hybridizes to the complement of the nucleic acid sequences specifically disclosed herein under standard conditions as known by those skilled in the art and encodes a variant capsid and/or capsid protein. Optionally, the variant capsid or capsid protein substantially retains at least one property of the capsid and/or capsid or capsid protein encoded by the nucleic acid sequence of SEQ ID NOS:1, 3, 5, 7, or 9. For example, a virus particle comprising the variant capsid or variant capsid protein can substantially retain the liver tropism profile of a virus particle comprising a capsid or capsid protein encoded by a nucleic acid coding sequence of SEQ ID NO:1, 3, 5, 7, or 9.

For example, hybridization of such sequences may be carried out under conditions of reduced stringency, medium stringency or even stringent conditions. Exemplary conditions for reduced, medium and stringent hybridization are as follows: (e.g., conditions represented by a wash stringency of 35-40% Formamide with 5×Denhardt's solution, 0.5%

SDS and 1×SSPE at 37° C.; conditions represented by a wash stringency of 40-45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively). See, e.g., Sambrook et al., *Molecular Cloning, A Laboratory Manual* (4th Ed. 2013) (Cold Spring Harbor Laboratory).

In other embodiments, nucleic acid sequences encoding a variant capsid or capsid protein of the invention have at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, or higher sequence identity with the nucleic acid sequence of SEQ ID NO:1, 3, 5, 7, or 9 and optionally encode a variant capsid or capsid protein that substantially retains at least one property of the capsid or capsid protein encoded by a nucleic acid of SEQ ID NO:1, 3, 5, 7, or 9.

As is known in the art, a number of different programs can be used to identify whether a nucleic acid or polypeptide has sequence identity to a known sequence. Percent identity as used herein means that a nucleic acid or fragment thereof shares a specified percent identity to another nucleic acid, when optimally aligned (with appropriate nucleotide insertions or deletions) with the other nucleic acid (or its complementary strand), using BLASTN. To determine percent identity between two different nucleic acids, the percent identity is to be determined using the BLASTN program "BLAST 2 sequences". This program is available for public use from the National Center for Biotechnology Information (NCBI) over the Internet (Altschul et al., (1997) *Nucleic Acids Res.* 25(17):3389-3402). The parameters to be used are whatever combination of the following yields the highest calculated percent identity (as calculated below) with the default parameters shown in parentheses: Program—blastn Matrix—0 BLOSUM62 Reward for a match—0 or 1 (1) Penalty for a mismatch—0, −1, −2 or −3 (−2) Open gap penalty—0, 1, 2, 3, 4 or 5 (5) Extension gap penalty—0 or 1 (1) Gap x_dropoff—0 or 50 (50) Expect—10.

Percent identity or similarity when referring to polypeptides, indicates that the polypeptide in question exhibits a specified percent identity or similarity when compared with another protein or a portion thereof over the common lengths as determined using BLASTP. This program is also available for public use from the National Center for Biotechnology Information (NCBI) over the Internet (Altschul et al., (1997) *Nucleic Acids Res.* 25(17):3389-3402). Percent identity or similarity for polypeptides is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

In particular embodiments, the nucleic acid can comprise, consist essentially of, or consist of a vector including but not limited to a plasmid, phage, viral vector (e.g., AAV vector, an adenovirus vector, a herpesvirus vector, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat).

In some embodiments, the nucleic acid encoding the synthetic AAV capsid protein further comprises an AAV rep coding sequence. For example, the nucleic acid can be a helper construct for producing viral stocks.

The invention also provides packaging cells stably comprising a nucleic acid of the invention. For example, the nucleic acid can be stably incorporated into the genome of the cell or can be stably maintained in an episomal form (e.g., an "EBV based nuclear episome").

The nucleic acid can be incorporated into a delivery vector, such as a viral delivery vector. To illustrate, the nucleic acid of the invention can be packaged in an AAV particle, an adenovirus particle, a herpesvirus particle, a baculovirus particle, or any other suitable virus particle.

Moreover, the nucleic acid can be operably associated with a promoter element. Promoter elements are described in more detail herein.

The present invention further provides methods of producing the virus vectors of the invention. In a representative embodiment, the present invention provides a method of producing a recombinant virus vector, the method comprising providing to a cell in vitro, (a) a template comprising (i) a heterologous nucleic acid, and (ii) packaging signal sequences sufficient for the encapsidation of the AAV template into virus particles (e.g., one or more (e.g., two) terminal repeats, such as AAV terminal repeats), and (b) AAV sequences sufficient for replication and encapsidation of the template into viral particles (e.g., the AAV rep and AAV cap sequences encoding an AAV capsid of the invention). The template and AAV replication and capsid sequences are provided under conditions such that recombinant virus particles comprising the template packaged within the capsid are produced in the cell. The method can further comprise the step of collecting the virus particles from the cell. Virus particles may be collected from the medium and/or by lysing the cells.

In one illustrative embodiment, the invention provides a method of producing a rAAV particle comprising an AAV capsid, the method comprising: providing a cell in vitro with a nucleic acid encoding a modified AAV5 capsid of the invention, an AAV rep coding sequence, an AAV vector genome comprising a heterologous nucleic acid, and helper functions for generating a productive AAV infection; and allowing assembly of the AAV particles comprising the AAV capsid and encapsidating the AAV vector genome.

The cell is typically a cell that is permissive for AAV viral replication. Any suitable cell known in the art may be employed, such as mammalian cells. Also suitable are trans-complementing packaging cell lines that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an EBV based nuclear episome.

As a further alternative, the rep/cap sequences may be stably carried (episomal or integrated) within a cell.

Typically, the AAV rep/cap sequences will not be flanked by the AAV packaging sequences (e.g., AAV ITRs), to prevent rescue and/or packaging of these sequences.

[The template (e.g., an rAAV vector genome) can be provided to the cell using any method known in the art. For example, the template may be supplied by a non-viral (e.g., plasmid) or viral vector. In particular embodiments, the template is supplied by a herpesvirus or adenovirus vector (e.g., inserted into the E1a or E3 regions of a deleted adenovirus). As another illustration, Palombo et al., (1998) *J. Virol.* 72:5025, describe a baculovirus vector carrying a reporter gene flanked by the AAV ITRs. EBV vectors may also be employed to deliver the template, as described above with respect to the replcap genes.

In another representative embodiment, the template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection are generally provided to the cell. Helper virus sequences necessary for AAV replication are known in the art. Typically, these sequences are provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes integrated in the chromosome or maintained as a stable extrachromosomal element. In representative embodiments, the helper virus sequences cannot be packaged into AAV virions, e.g., are not flanked by AAV ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is optionally a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further contains the rAAV template. The AAV rep/cap sequences and/or the rAAV template may be inserted into a deleted region (e.g., the E1a or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as a "EBV based nuclear episome," see Margolski, (1992) *Curr. Top. Microbiol. Immun.* 158:67).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, in representative embodiments, the adenovirus helper sequences and the AAV rep/cap sequences are not flanked by the AAV packaging sequences (e.g., the AAV ITRs), so that these sequences are not packaged into the AAV virions.

Herpesvirus may also be used as a helper virus in AAV packaging methods. Hybrid herpesviruses encoding the AAV rep protein(s) may advantageously facilitate for more scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described by Urabe et al., (2002) *Human Gene Therapy* 13:1935-43.

Other methods of producing AAV use stably transformed packaging cells (see, e.g., U.S. Pat. No. 5,658,785).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al., (1999) *Gene Therapy* 6:973). In representative embodiments, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of virus particles. In particular embodiments, the virus stock has a titer of at least about $10^5$ transducing units (tu)/ml, at least about $10^6$ tu/ml, at least about $10^7$ tu/ml, at least about $10^8$ tu/ml, at least about $10^9$ tu/ml, or at least about $10^{10}$ tu/ml.

The novel capsid protein and capsid structures find use in raising antibodies, for example, for diagnostic or therapeutic uses or as a research reagent. Thus, the invention also provides antibodies against the novel capsid proteins and capsids of the invention.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep or human, or can be a chimeric antibody. See, e.g., Walker et al., *Mol. Immunol.* 26, 403-11 (1989). The antibodies can be recombinant monoclonal antibodies, for example, produced according to the methods disclosed in U.S. Pat. No. 4,474,893 or 4,816, 567. The antibodies can also be chemically constructed, for example, according to the method disclosed in U.S. Pat. No. 4,676,980.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254, 1275-1281).

Polyclonal antibodies can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies can be produced in a hybridoma cell line according to the technique of Kohler and Milstein, (1975) *Nature* 265, 495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., W. Huse, (1989) *Science* 246, 1275-81.

Antibodies specific to a target polypeptide can also be obtained by phage display techniques known in the art.

Various immunoassays can be used for screening to identify antibodies having the desired specificity. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes can be used as well as a competitive binding assay.

Antibodies can be conjugated to a solid support (e.g., beads, plates, slides or wells formed from materials such as latex or polystyrene) in accordance with known techniques. Antibodies can likewise be directly or indirectly conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

Methods of Using Modified AAV5 Capsids

The present invention also relates to methods for delivering heterologous nucleotide sequences into the liver with enhanced efficiency and low seroreactivity while minimizing delivery to other organs. The virus vectors of the invention may be employed to deliver a nucleotide sequence of interest to a hepatocyte or other cell in vitro, e.g., to produce a polypeptide or nucleic acid in vitro or for ex vivo gene therapy. The vectors are additionally useful in a method of delivering a nucleotide sequence to a subject in need thereof, e.g., to express a therapeutic or immunogenic polypeptide or nucleic acid. In this manner, the polypeptide or nucleic acid may thus be produced in vivo in the subject. The subject may be in need of the polypeptide or nucleic acid because the subject has a deficiency of the polypeptide, or because the production of the polypeptide or nucleic acid in the subject may impart some therapeutic effect, as a method of treatment or otherwise, and as explained further below.

In particular embodiments, the vectors are useful to express a polypeptide or nucleic acid that provides a beneficial effect to the subject in general. In other embodiments, the vectors are useful to express a polypeptide or nucleic acid that provides a beneficial effect to cells in the liver (e.g., hepatocytes).

Thus, one aspect of the invention relates to a method of delivering a nucleic acid of interest to a hepatocyte, the method comprising contacting the hepatocyte with the AAV particle of the invention.

In another aspect, the invention relates to a method of delivering a nucleic acid of interest to a hepatocyte in a mammalian subject, the method comprising administering an effective amount of the AAV particle or pharmaceutical formulation of the invention to a mammalian subject, thereby delivering the nucleic acid of interest to a hepatocyte in the mammalian subject.

A further aspect of the invention relates to a method of treating a disorder in a mammalian subject in need thereof, wherein the disorder is treatable by expressing a product in the liver of the subject, the method comprising administering a therapeutically effective amount of the AAV particle of the invention to the subject, wherein the product is expressed, thereby treating the disorder.

In general, the virus vectors of the invention may be employed to deliver any foreign nucleic acid with a biological effect to treat or ameliorate the symptoms associated with any disorder related to gene expression. Further, the invention can be used to treat any disease state for which it is beneficial to deliver a therapeutic polypeptide. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (inhibitory RNA including without limitation RNAi such as siRNA or shRNA, antisense RNA or microRNA to remove repeats), amyotrophic lateral sclerosis, epilepsy (galanin, neurotrophic factors), and other neurological disorders, cancer (endostatin, angiostatin, TRAIL, FAS-ligand, cytokines including interferons; inhibitory RNA including without limitation RNAi (such as siRNA or shRNA), antisense RNA and microRNA including inhibitory RNA against VEGF, the multiple drug resistance gene product or a cancer immunogen), diabetes mellitus (insulin, PGC-α1, GLP-1, myostatin pro-peptide, glucose transporter 4), muscular dystrophies including Duchenne and Becker (e.g., dystrophin, mini-dystrophin, micro-dystrophin, insulin-like growth factor I, a sarcoglycan [e.g., α, β, γ], Inhibitory RNA [e.g., RNAi, antisense RNA or microRNA] against myostatin or myostatin propeptide, laminin-alpha2, Fukutin-related protein, dominant negative myostatin, follistatin, activin type II soluble receptor, anti-inflammatory polypeptides such as the Ikappa B dominant mutant, sarcospan, utrophin, mini-utrophin, inhibitory RNA [e.g., RNAi, antisense RNA or microRNA] against splice junctions in the dystrophin gene to induce exon skipping [see, e.g., WO/2003/095647], inhibitory RNA (e.g., RNAi, antisense RNA or micro RNA] against U7 snRNAs to induce exon skipping [see, e.g., WO/2006/021724], and antibodies or antibody fragments against myostatin or myostatin propeptide), Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects including other lysosomal storage disorders and glycogen storage disorders, congenital emphysema (α1-antitrypsin), Lesch-Nyhan Syndrome (hypoxanthine guanine phosphoribosyl transferase), Niemann-Pick disease (sphingomyelinase), Maple Syrup Urine Disease (branched-chain keto acid dehydrogenase), retinal degenerative diseases (and other diseases of the eye and retina; e.g., PDGF, endostatin and/or angiostatin for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver (RNAi such as siRNA or shRNA, microRNA or antisense RNA for hepatitis B and/or hepatitis C genes), kidney, heart including congestive heart failure or peripheral artery disease (PAD) (e.g., by delivering protein phosphatase inhibitor I [I-1], phospholamban, sarcoplasmic endoreticulum $Ca^{2+}$-ATPase [serca2a], zinc finger proteins that regulate the phospholamban gene, Pim-1, PGC-1α, SOD-1, SOD-2, ECF-SOD, kallikrein, thymosin-β4, hypoxia-inducible transcription factor [HIF], βarkct, β2-adrenergic receptor, β2-adrenergic receptor kinase [βARK], phosphoinositide-3 kinase [PI3 kinase], calsarcin, an angiogenic factor, S100A1, parvalbumin, adenylyl cyclase type 6, a molecule that effects G-protein coupled receptor kinase type 2 knockdown such as a truncated constitutively active bARKct, an inhibitory RNA [e.g., RNAi, antisense RNA or microRNA] against phospholamban; phospholamban inhibitory or dominant-negative molecules such as phospholamban S16E, etc.), arthritis (insulin-like growth factors), joint disorders (insulin-like growth factors), intimal hyperplasia (e.g., by delivering enos, inos), improve survival of heart transplants (superoxide dismutase), AIDS (soluble CD4), muscle wasting (insulin-like growth factor I, myostatin pro-peptide, an anti-apoptotic factor, follistatin), limb ischemia (VEGF, FGF, PGC-1α, EC-SOD, HIF), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including RANKL and/or VEGF) can be administered with a bone allograft, for example, following a break or surgical removal in a cancer patient.

Exemplary lysosomal storage diseases that can be treated according to the present invention include without limitation: Hurler's Syndrome (MPS IH), Scheie's Syndrome (MPS IS), and Hurler-Scheie Syndrome (MPS IH/S) (α-L-iduronidase); Hunter's Syndrome (MPS II) (iduronate sulfate sulfatase); Sanfilippo A Syndrome (MPS IIIA) (Heparan-S-sulfate sulfaminidase), Sanfilippo B Syndrome (MPS IIIB) (N-acetyl-D-glucosaminidase), Sanfilippo C Syndrome (MPS IIIC) (Acetyl-CoA-glucosaminide N-acetyl-transferase), Sanfilippo D Syndrome (MPS IIID) (N-acetyl-glucosaminine-6-sulfate sulfatase); Morquio A disease (MPS IVA) (Galactosamine-6-sulfate sulfatase), Morquio B disease (MPS IV B) (β-Galactosidase); Maroteaux-lmay disease (MPS VI) (arylsulfatase B); Sly Syndrome (MPS VII) (β-glucuronidase); hyaluronidase deficiency (MPS IX) (hyaluronidase); sialidosis (mucolipidosis I), mucolipidosis II (I-Cell disease) (N-actylglucos-aminyl-1-phosphotransferase catalytic subunit), mucolipidosis III (pseudo-Hurler polydystrophy) (N-acetylglucos-aminyl-1-phosphotransferase; type IIIA [catalytic subunit] and type IIIC [substrate recognition subunit]); GM1 gangliosidosis (ganglioside β-galactosidase), GM2 gangliosidosis Type I (Tay-Sachs disease) (β-hexaminidase A), GM2 gangliosidosis type II (Sandhoff's disease) (β-hexosaminidase B); Niemann-Pick disease (Types A and B) (sphingomyelinase); Gaucher's disease (glucocerebrosidase); Farber's disease (ceraminidase); Fabry's disease (α-galactosidase A); Krabbe's disease (galactosylceramide β-galactosidase); metachromatic leukodystrophy (arylsulfatase A); lysosomal acid lipase deficiency including Wolman's disease (lysosomal acid lipase); Batten disease (juvenile neuronal ceroid lipofuscinosis) (lysosomal transmembrane CLN3 protein) sialidosis (neuraminidase 1); galactosialidosis (Goldberg's syndrome) (protective protein/cathepsin A); α-mannosidosis (α-D-mannosidase); β-mannosidosis (β-D-mannosidosis); fucosidosis (α-D-fucosidase); aspartylglucosaminuria (N-Aspartylglucosaminidase); and sialuria (Na phosphate cotransporter).

Exemplary glycogen storage diseases that can be treated according to the present invention include, but are not limited to, Type Ia GSD (von Gierke disease) (glucose-6-phosphatase), Type Ib GSD (glucose-6-phosphate translocase), Type Ic GSD (microsomal phosphate or pyrophosphate transporter), Type Id GSD (microsomal glucose transporter), Type II GSD including Pompe disease or infantile Type IIa GSD (lysosomal acid α-glucosidase) and Type IIb (Danon) (lysosomal membrane protein-2), Type IIIa and IIIb GSD (Debrancher enzyme; amyloglucosidase and oligoglucanotransferase), Type IV GSD (Andersen's disease) (branching enzyme), Type V GSD (McArdle disease) (muscle phosphorylase), Type VI GSD (Hers' disease) (liver phosphorylase), Type VII GSD (Tarui's disease) (phosphofructokinase), GSD Type VIII/IXa (X-linked phosphorylase kinase), GSD Type IXb (Liver and muscle phosphorylase kinase), GSD Type IXc (liver phosphorylase kinase), GSD Type IXd (muscle phosphorylase kinase), GSD O (glycogen synthase), Fanconi-Bickel syndrome (glucose transporter-2), phosphoglucoisomerase deficiency, muscle phosphoglycerate kinase deficiency, phosphoglycerate mutase deficiency, fructose 1,6-diphosphatase deficiency, phosphoenolpyruvate carboxykinase deficiency, and lactate dehydrogenase deficiency.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using inhibitory RNA such as RNAi (e.g., siRNA or shRNA), microRNA or antisense RNA. For unbalanced disease states, gene transfer can be used to create a disease state in a model system, which can then be used in efforts to counteract the disease state. Thus, the virus vectors according to the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The virus vectors according to the present invention may also be employed to provide an antisense nucleic acid or inhibitory RNA (e.g., microRNA or RNAi such as a siRNA or shRNA) to a cell in vitro or in vivo. Expression of the inhibitory RNA in the target cell diminishes expression of a particular protein(s) by the cell. Accordingly, inhibitory RNA may be administered to decrease expression of a particular protein in a subject in need thereof. Inhibitory RNA may also be administered to cells in vitro to regulate cell physiology, e.g., to optimize cell or tissue culture systems.

As a further aspect, the virus vectors of the present invention may be used to produce an immune response in a subject. According to this embodiment, a virus vector comprising a nucleic acid encoding an immunogen may be administered to a subject, and an active immune response (optionally, a protective immune response) is mounted by the subject against the immunogen. Immunogens are as described hereinabove.

Alternatively, the virus vector may be administered to a cell ex vivo and the altered cell is administered to the subject. The heterologous nucleic acid is introduced into the cell, and the cell is administered to the subject, where the heterologous nucleic acid encoding the immunogen is optionally expressed and induces an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

The virus vectors of the present invention may also be administered for cancer immunotherapy by administration of a viral vector expressing a cancer cell antigen (or an immunologically similar molecule) or any other immunogen that produces an immune response against a cancer cell. To illustrate, an immune response may be produced against a cancer cell antigen in a subject by administering a viral vector comprising a heterologous nucleotide sequence encoding the cancer cell antigen, for example to treat a patient with cancer. The virus vector may be administered to a subject in vivo or by using ex vivo methods, as described herein.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to, leukemia, lymphoma (e.g., Hodgkin and non-Hodgkin lymphomas), colorectal cancer, renal cancer, liver cancer, breast cancer, lung cancer, prostate cancer, testicular cancer, ovarian cancer, uterine cancer, cervical cancer, brain cancer (e.g., gliomas and glioblastoma), bone cancer, sarcoma, melanoma, head and neck cancer, esophageal cancer, thyroid cancer, and the like. In embodiments of the invention, the invention is practiced to treat and/or prevent tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

Cancer cell antigens have been described hereinabove. By the terms "treating cancer" or "treatment of cancer," it is intended that the severity of the cancer is reduced or the cancer is prevented or at least partially eliminated. For example, in particular contexts, these terms indicate that metastasis of the cancer is prevented or reduced or at least partially eliminated. In further representative embodiments these terms indicate that growth of metastatic nodules (e.g., after surgical removal of a primary tumor) is prevented or reduced or at least partially eliminated. By the terms "prevention of cancer" or "preventing cancer" it is intended that the methods at least partially eliminate or reduce the incidence or onset of cancer. Alternatively stated, the onset or progression of cancer in the subject may be slowed, controlled, decreased in likelihood or probability, or delayed.

In particular embodiments, cells may be removed from a subject with cancer and contacted with a virus vector according to the present invention. The modified cell is then administered to the subject, whereby an immune response against the cancer cell antigen is elicited. This method is particularly advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (e.g., CTL inductive cytokines) may be administered to a subject in conjunction with the virus vectors.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

The viral vectors are further useful for targeting liver cells for research purposes, e.g., for study of liver function in vitro or in animals or for use in creating and/or studying animal models of disease. For example, the vectors can be used to deliver heterologous nucleic acids to hepatocytes in animal models of liver injury, e.g., fibrosis or cirrhosis or animal models of liver diseases such as viral infections (e.g., hepatitis viruses).

Further, the virus vectors according to the present invention find further use in diagnostic and screening methods, whereby a gene of interest is transiently or stably expressed in a cell culture system, or alternatively, a transgenic animal model. The invention can also be practiced to deliver a nucleic acid for the purposes of protein production, e.g., for laboratory, industrial or commercial purposes.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a nucleic acid including those described herein. As a further option, the subject can be a laboratory animal and/or an animal model of disease.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the virus vector can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell (cancers and tumors are described above). Moreover, the cells can be from any species of origin, as indicated above.

The virus vectors may be introduced to cells in vitro for the purpose of administering the modified cell to a subject. In particular embodiments, the cells have been removed from a subject, the virus vector is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the recombinant virus vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

In some embodiments, cells that have been transduced with the virus vector may be administered to elicit an immunogenic response against the delivered polypeptide (e.g., expressed as a transgene or in the capsid). Typically, a quantity of cells expressing an effective amount of the polypeptide in combination with a pharmaceutically acceptable carrier is administered. Optionally, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vectors or capsids of the invention to subjects. In particular embodiments, the method comprises a method of delivering a nucleic acid of interest to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

The virus vectors of the invention can further be administered to a subject to elicit an immunogenic response (e.g., as a vaccine). Typically, vaccines of the present invention comprise an effective amount of virus in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units or more, preferably about $10^7$ or $10^8$, $10^9$, $10^{10}$, $10^{11}$, $10^{12}$, $10^{13}$, $10^{14}$ or $10^{15}$ transducing units, yet more preferably about $10^{12}$ to $10^{14}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and on the nature of the particular vector that is being used.

In some embodiments, the viral vector is administered directly to the liver. Direct administration can result in high specificity of transduction of hepatocytes, e.g., wherein at least 80%, 85%, 90%, 95% or more of the transduced cells are hepatocytes. Any method known in the art to administer vectors directly to the liver can be used. The vector may be introduced by direct injection into the liver or injection into an artery or vein feeding the liver, e.g., intraportal delivery.

Typically, the viral vector will be administered in a liquid formulation by systemic delivery or direct injection to the desired region or compartment in the liver. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. Controlled release of parvovirus and AAV vectors is described by international patent publication WO 01/91803.

Delivery to any of these tissues can also be achieved by delivering a depot comprising the virus vector, which can be implanted into the tissue or the tissue can be contacted with a film or other matrix comprising the virus vector. Examples of such implantable matrices or substrates are described in U.S. Pat. No. 7,201,898).

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 μg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

Example 1

Generation of AAV5 Capsid Mutant Library

A diverse viral library consisting of mutant AAV5 capsids with point mutations distributed throughout the VP3 region was generated (FIG. 1) via random mutagenesis and the staggered extension process(stEP) as described by Zhao et al. (Nat. Biotechnology 1998). In detail, the WT-AAV5 capsid gene (from the XR5 packaging plasmid) was randomly mutated using error prone PCR and a corresponding set of primers that encompassed the VP3 gene. The forward primer (SEQ ID NO:13) overlapped the RSRII restriction enzyme cutsite upstream of the VP3 gene while the reverse primer (SEQ ID NO:14) overlapped the NotI cutsite downstream of the VP3 gene to facilitate cloning of the PCR product into an "infectious", or wildtype AAV5 plasmid. Around 10 ng of template DNA was amplified over thirty cycles using an error prone DNA polymerase to achieve a range of 2-17 mutations in the VP3 gene per each PCR fragment. To further diversify the mutant AAV5 library, the point mutations generated by error prone PCR were shuffled using stEP in which roughly 100 ng of mutated AAV5 VP3 DNA was subjected to 100 extremely short cycles of denaturing (~20 s), annealing (~5 s), and elongation (~10 s) using the same primers as described before.

The mutant VP3 stEP PCR product was then purified and digested to completion using RSRII/NotI restriction enzymes. Digested DNA was isolated using agarose gel purification and cloned into a backbone containing an AAV2 REP gene and a partial AAV5 Capsid gene flanked by AAV2 ITR sequences to create an "infectious" plasmid, or a replication competent AAV plasmid. The resulting mixture was electroporated into DH10B electrocompetent bacteria and spread across two 10-cm LB agar plates containing ampicillin. A viral plasmid library of $5 \times 10^5$ independent clones was generated as determined by quantification of the number of colonies following bacteria transformation. To confirm the diversity of the library, 20 colonies were picked from the plates for miniprep and sequencing. Sequencing results revealed that the AAV5 VP3 mutants had diverse amounts and types of point mutations, ranging from 4 to 22 mutations per VP3 region. Individual bacteria colonies were pooled together by washing the LB-agar plates with terrific broth medium and then cultured in four liters of TB medium. The propagated bacteria were then used for large-scale purification of the plasmid DNA library by ultracentrifugation with CsCl-ethidium bromide gradients.

Using the plasmid library, an AAV5 viral mutant library was produced and then purified by CsCl centrifugation. In detail, the plasmid library and a helper plasmid were transfected into human embryonic kidney (HEK293) cells at a 1:1 ratio via the calcium phosphate transfection method. After 60-72 hours post transfection, the transfected cells and media were collected. The viral particles were released via the freeze thaw method and purified using CsCl density centrifugation. For all purified AAV experiments, the AAV titer was determined by the dotblot method.

Example 2

Selection of AAV5 Library Using Huh7 Cells

Figure 2:
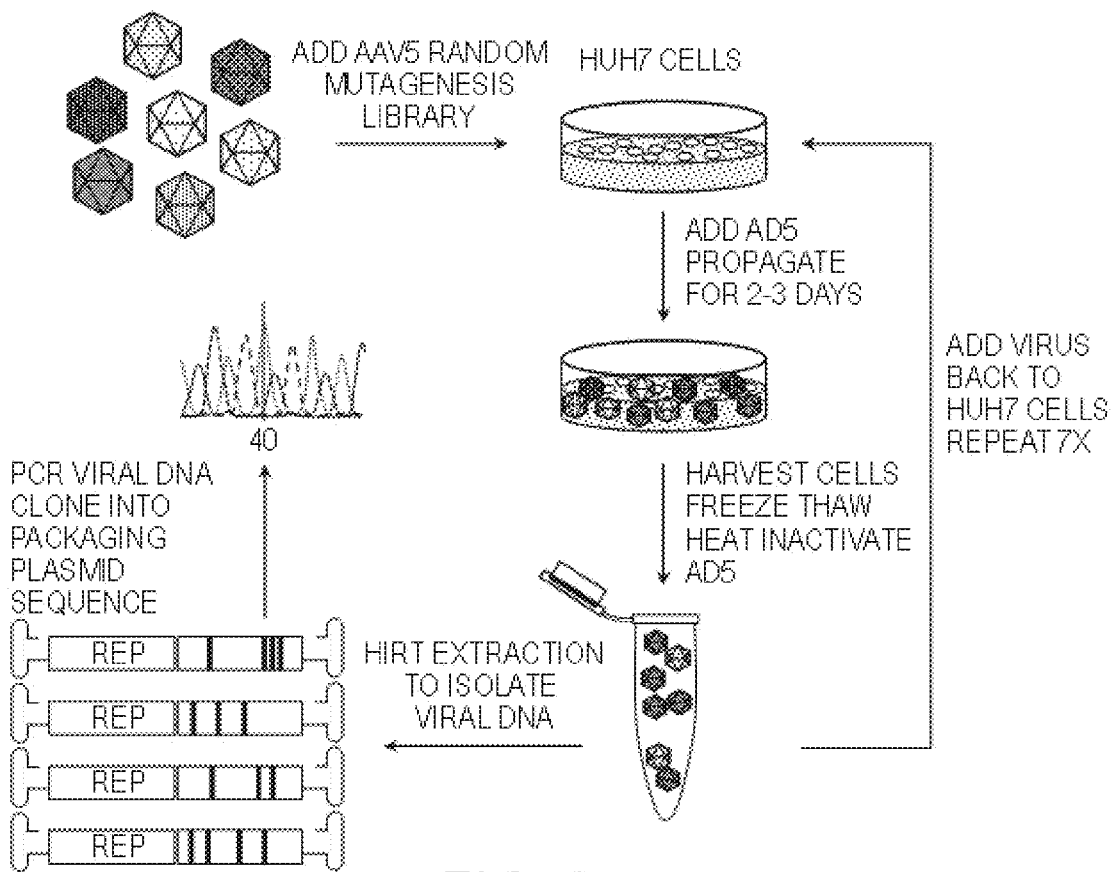
FIG. 2 depicts the screening of the AAV5 mutant library on Huh7 cells to obtain variants with increased liver tropism.

The AAV5 mutant viral library was then selected against the hepatocyte derived cellular carcinoma cell line Huh7 through a process that is summarized in FIG. 2. Huh7 cells were used as the selection model for screening variants with increased infectivity in human liver cells as the cell line was previously described to be a robust predictor for infectivity in human hepatocytes (Li et al, Molecular Therapy, 2015). The AAV5 viral library was added to Huh7 cells at a MOI of 5000 vector genomes per cell and coinfected with wild-type-adenovirus type-5(wt-ad) at a MOI of 100 vg per cell. Addition of wt-ad allows replication of variants that successfully infected the Huh7 cells and provides additional selective pressure to thoroughly enrich the variant population that infects huh7 cells more efficiently. After 72 hours of infection, the cells were collected and lysed via three freeze thaw cycles with a dry ice and ethanol mixture. The cell lysate was then incubated at 56° C. for 1 hour to inactivate the wt-ad present in lysate. The cell lysate was then centrifuged at 15000 rpm for 5 min and the supernatant containing the mutant viral particles was collected. The virus in the supernatant was titered by real-time PCR with SYBR-Green dye. Huh7 cells were again infected with virus from the previous round of selection at a MOI of 5000 vg/cell.

In total, 7 rounds of selection on Huh7 cells were performed. For the last round of selection, the infected cells were washed with PBS twice to remove any virus that did not manage to infect the cells. The viral DNA was then extracted from the cells via a modified Hirt Extraction as described by Arad et al. (Biotechniques 1998). In short, cells were suspended in 250 μl of a Tris-HCl/EDTA solution containing 100 μg/ml RNase A. Cells were lysed with the addition of a 1.2% sodium dodecyl sulfate solution and incubated for 5 min at room temperature. Chromosomal DNA and cellular debris were precipitated with the addition of a cesium chloride, potassium acetate, and acetic acid solution and incubated on ice for 15 min. The mixture was then centrifuged at 4° C. for 15 min, and the supernatant was loaded onto a Qiagen Qiaprep Spin column. The bound DNA was then washed, eluted and amplified via PCR using the same primers used for the error prone PCR. The resulting PCR amplicons were purified and subsequently digested with RSRII and NotI and ligated into a packaging plasmid containing AAV2 Rep and a partial AAV5 Cap gene. The ligation mixture was transformed into bacteria and spread onto agar plates containing ampicillin. After overnight incubation, individual colonies were picked for plasmid amplification via miniprep. Amplified plasmid DNA was incubated with RNASE A and sequenced.

Figure 3:
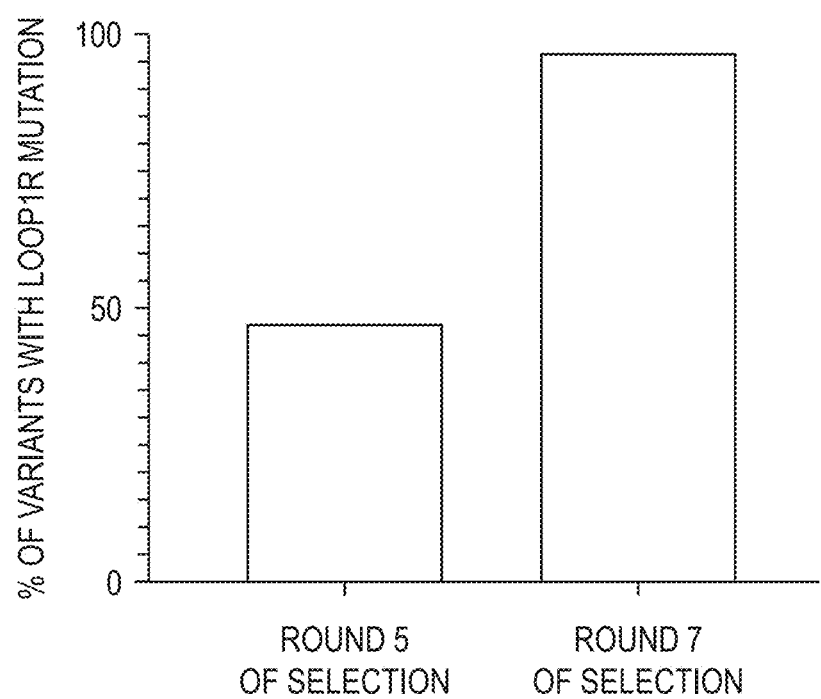
FIG. 3 depicts the percentage of sequenced variants that carried the Loop1R mutation from the fifth and seventh rounds of selection on Huh7 cells.

Roughly 60-70 plasmids were sequenced from the $5^{th}$ and $7^{th}$ rounds of selection for a total of 145 colonies. Four primers spanning the AAV5 cap gene were used to accurately sequence the entirety of the cap gene for each miniprepped plasmid. Sequencing results revealed approximately half (31 out of 65) of the sequenced mutants from the fifth round of selection contained a common mutation in the Loop1 region of the AAV5 VP3 protein. Further enrichment of the mutants carrying the Loop1 mutation was observed after the $7^{th}$ round of selection. In the mutants sequenced for the seventh round, 73 out of 75 variants carried the Loop1 mutation (FIG. 3). A large portion of the variants only carried the single mutation in the Loop1 region with no other mutations while the remaining portion contained one or two additional mutations throughout the entire VP3 region. The remaining two mutants contained mutations not found in the Loop1 mutants which included areas such as the VP2/VP3 Junction and the Loop 8 region. Many of the mutations found were in regions that are thought to be on the surface of the AAV5 capsid, which is not surprising considering changes in receptor engagement and binding are most likely to contribute to changes in infectivity. Of note, wild type AAV5 capsid sequences were not detected during any rounds of sequencing. From these sequencing results, we concluded that the 7 rounds of selection had specifically enriched the Loop1 mutation variants, likely due to a substantial increase in infectivity compared to all the other mutations in the library. Of the two hundred mutants sequenced, approximately 25 were unique and were used to package and produce double stranded GFP vector to assess yield and infectivity. Crude lysates containing the mutant GFP vectors were titered via RT-PCR and only mutants that could produce acceptable titers were selected for quick screens using a GFP reporter gene in Huh7 cells using unpurified virus in crude lysate. Five mutants, MV1, MV18, MV20, MV50, and MV53 showed the best yield and transduction capabilities and were chosen for larger scale production and purification for further characterization. Alignment of VP1 encoding nucleotide sequences of the various mutants and wt-AAV5 are provided in FIG. 4. Alignment of VP1 amino acid sequences of the various mutants and wt-AAV5 are provided in FIG. 5.

Example 3

Characterization of AAV5 Mutants using In Vitro Assays and Protein Modeling

AAV5 mutants were taken for further characterization using in vitro infectivity assays and protein modeling. First, purified virus was produced via the triple transfection and cesium chloride density ultracentrifugation methods. Briefly, HEK293 cells were transfected with a helper plasmid, a self-complementary GFP (sc-GFP) vector plasmid, and a packaging plasmid containing the mutant AAV5 capsid gene and an AAV2 rep gene. Cells were harvested 72 hours post transfection and isolated by centrifugation. The media was collected and stored while the cell pellet was resuspended and subjected to three freeze thaw cycles. The resulting cell lysate was incubated with Dnase 1 and Rnase A at 37° C. and centrifuged and the supernatant was collected. The virus from the supernatant and the media were then concentrated by PEG precipitation followed by two rounds of cesium chloride (CsCl) density ultracentrifugation. CsCl fractions containing virus were determined by DNA dotblot and combined and dialyzed using 5% sorbitol in PBS. Dialyzed virus preparations were again titered using DNA dot blot. All viruses that were tested were titered in the same dotblot to allow consistent measurement of viral titers. Dotblot of viral preparations showed that the AAV5 mutants had similar yields of virus compared to AAV5, indicating that the mutations selected for in the screening process had no significant impact on production and thus were viable for use in a clinical setting in terms of yield.

Figure 6:
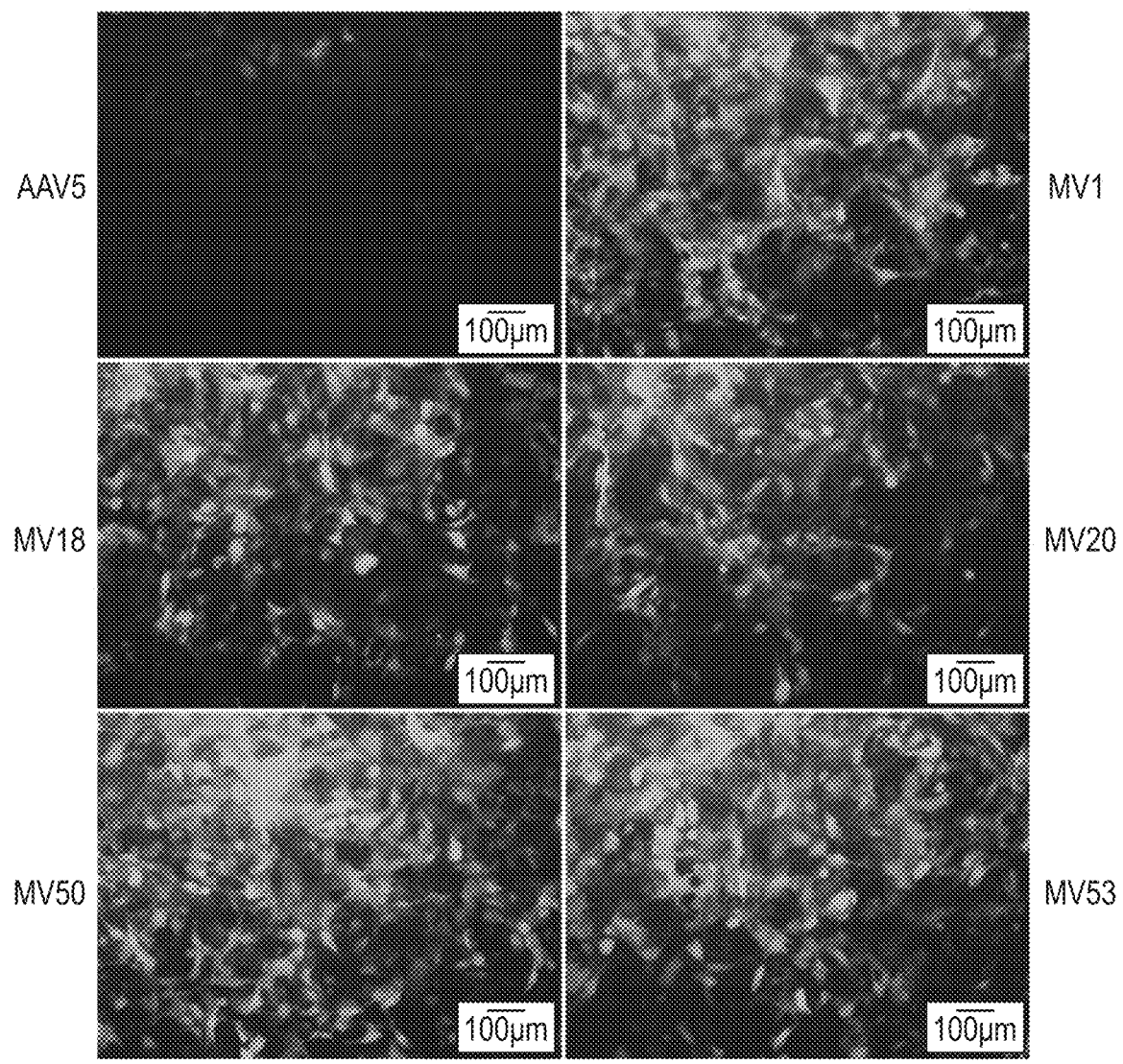
FIG. 6 depicts a comparison of green fluorescent protein (GFP) expression in Huh7 cells after infection by wild type AAV5 or AAV5 mutants packaged with GFP reporter gene. Huh7 cells were infected with a MOI of $1 \times 10^5$ vector genomes per cell. Images were taken 72 hours post infection with a fluorescent microscope.
Figure 7A:
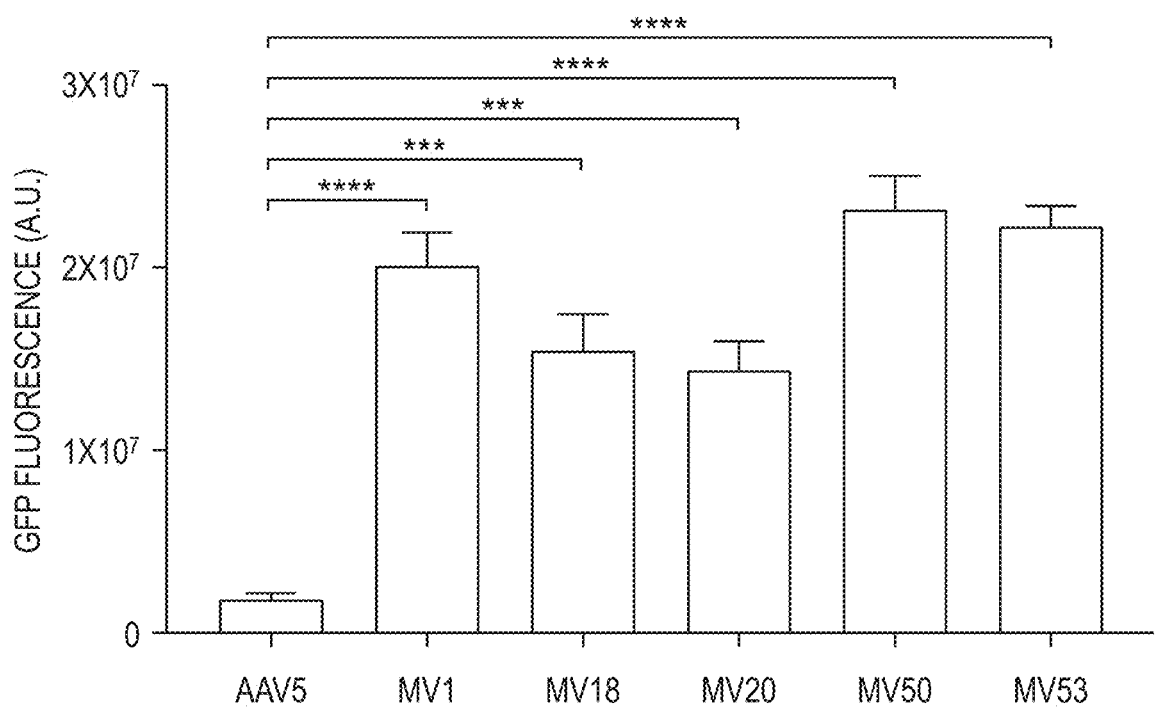
FIGS. 7A-B depict quantitative comparisons of GFP expression in Huh7 cells after infection by wild type AAV5 or AAV5 mutants packaged with GFP reporter gene. Huh7 cells were infected with a MOI of $1 \times 10^5$ vector genomes per cell. Cells were lysed 72 hours post infection and quantified with a fluorometric GFP quantification kit from Cell Bio Labs.
Figure 7B:
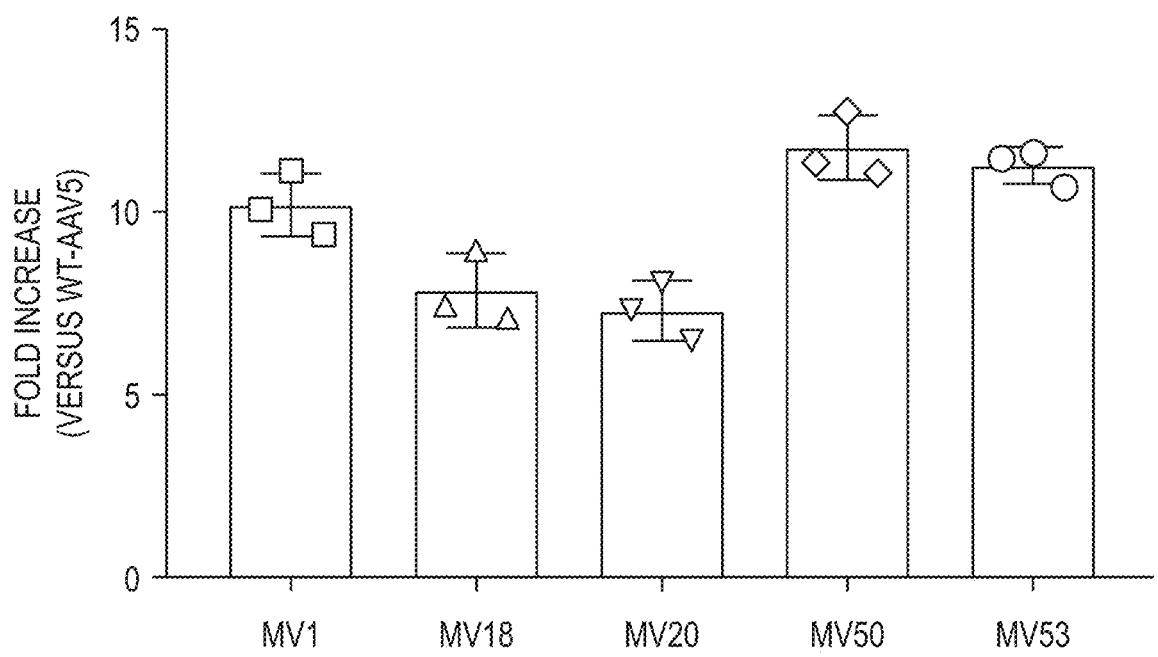

Purified viral preparations for the selected five mutants were tested for transduction in Huh7 cells. Huh7 cells were infected with AAV5 and mutant self-complementary(sc)-GFP encoding viruses at a MOI of 100,000 viral genomes (vg) per cell and co-infected with 5000 vg/cell of wt-ad to speed up the process of AAV genome expression. Forty-eight hours after infection, cells were taken for imaging and quantification of GFP expression. Imaging of GFP expression revealed that all five mutants had significantly increased GFP expression compared to AAV5 (FIGS. 6, 7A). Variant MV50 was the best performing variant that was 12× better than AAV5 in transduction of Huh7 cells (FIG. 7B). The second and third best variants were MV53 and MV1, which were 11× and 10× better than AAV5, respectively (FIG. 7B). All three of the best performing variants shared a glycine to arginine mutation in the Loop1 region, which was named 'Loop1R'. MV1, MV50, and MV53 also carried an extra mutation along with Loop1R that was different for each variant. The fourth best performing mutant was MV18, which was roughly around 7× better than AAV5, and only contained the Loop1R mutation. These results confirmed previously noted sequencing data that suggested the Loop1R mutation was specifically enriched during screening in Huh7 cells. As such, the Loop1R mutation is contributing the most to increasing infectivity in Huh7 cells while additional mutations are complimentary to the Loop1R mutation and add small increases in transduction. The final mutant, MV20, does not carry the Loop1R mutation, but still shows a 6× increase in infectivity compared to AAV5. This suggests that the mechanism in which MV20 is increasing infectivity may be different compared to the other mutants.

Figure 8:
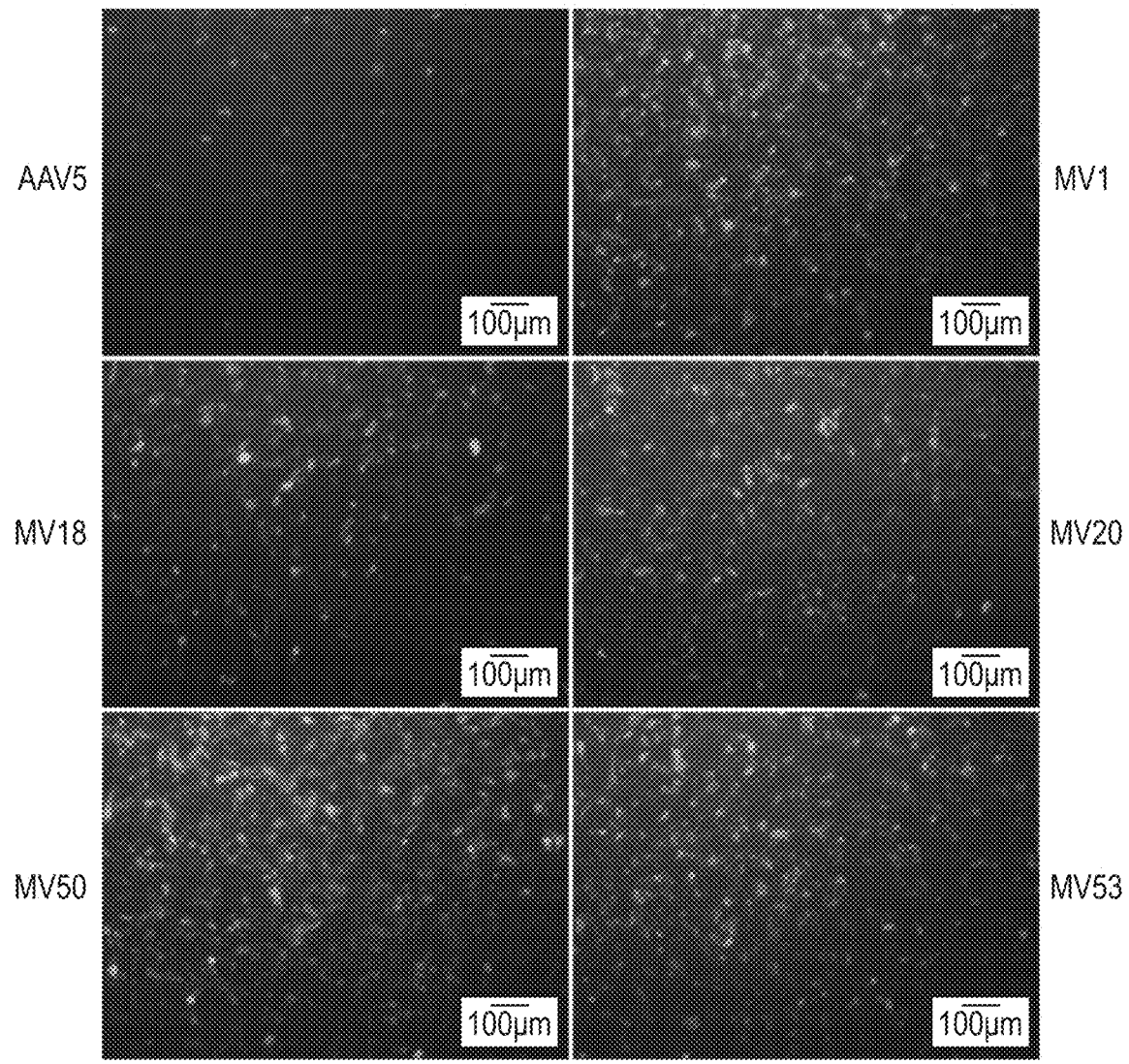
FIG. 8 depicts a comparison of green fluorescent protein (GFP) expression in HepG2 cells after infection by wild type AAV5 or AAV5 mutants packaged with GFP reporter gene. HepG2 cells were infected with a MOI of $1 \times 10^5$ vector genomes per cell. Images were taken 72 hours post infection with a fluorescent microscope.
Figure 9A:
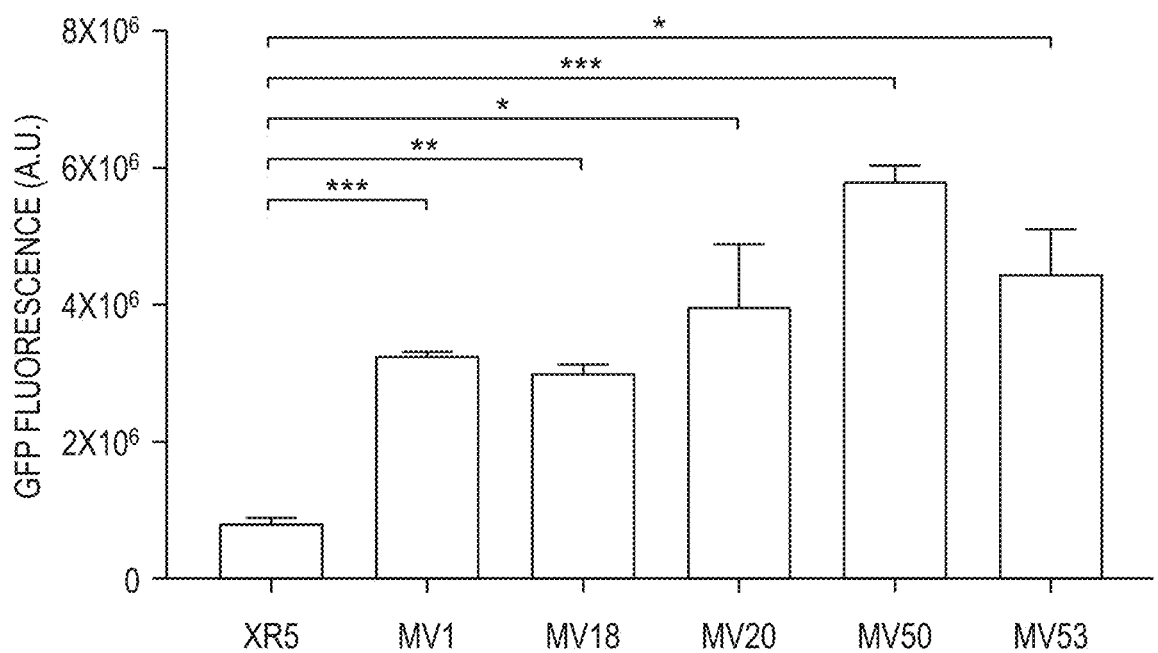
FIGS. 9A-B depict quantitative comparisons of GFP expression in HepG2 cells after infection by wild type AAV5 or AAV5 mutants packaged with GFP reporter gene. HepG2 cells were infected with a MOI of $1 \times 10^5$ vector genomes per cell. Cells were lysed 72 hours post infection and quantified with a fluorometric GFP quantification kit from Cell Bio Labs.
Figure 9B:
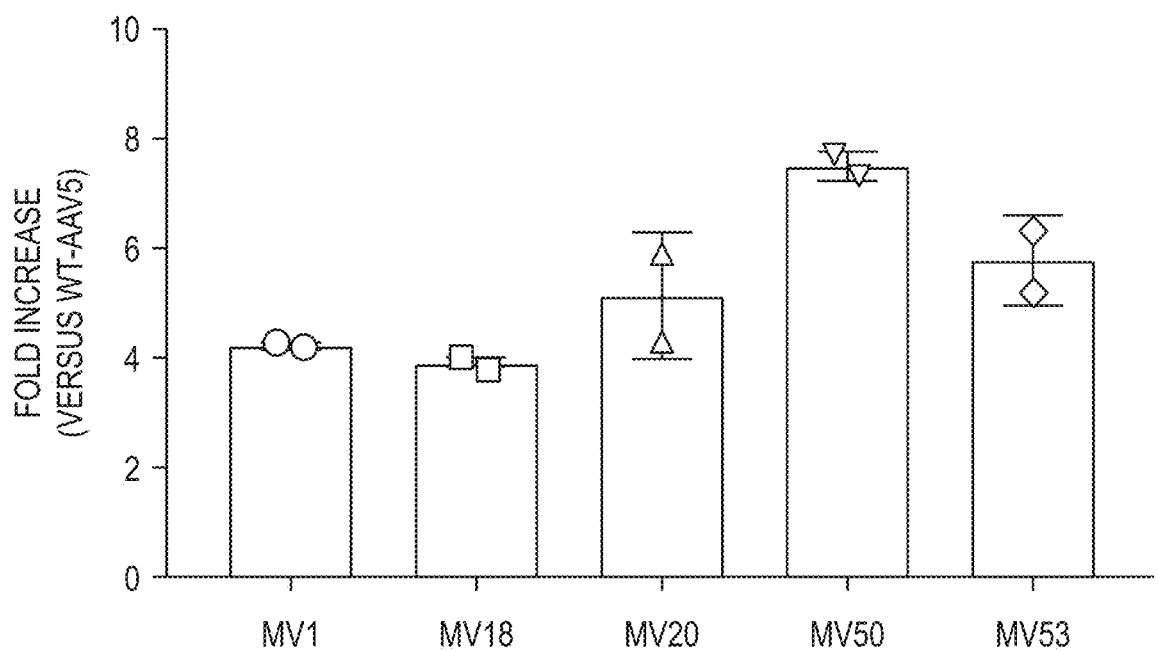

Next, the five variants were tested against AAV5 in HepG2 cells, a human liver cancer cell line, to evaluate if the increases in transduction seen in Huh7 cells were cell-line specific. Similar to the results from before, the variants exhibited significant increases in transduction compared to AAV5 in HepG2 cells, albeit at a lower magnitude when compared to the increases in Huh7 cells (FIGS. 8, 9A). MV50 once again was the best performing variant with a 7× increase in GFP expression when compared to AAV5 while other variants exhibited slightly lower increases in transduction that ranged from around 4×-6× depending on the variant (FIG. 9B). One potential reason for the slightly lower magnitude of increase in HepG2 versus Huh7 cells could be due to the tendency of HepG2 cells to grow in clusters, thus making it harder for AAV to bind to the surface of the cells and facilitate entry. Additionally, due to the nature of cancer cell lines, it is also a possibility that the expression levels of various entry receptors on the cell surface varies between Huh7 and HepG2, thus leading to different levels of transduction depending on the receptors that are utilized by AAV5 and the variants. Regardless, increased transduction in both liver cancer cell lines indicated that these mutant AAV5 were not Huh7-specific and have a higher likelihood of translating to human hepatocytes.

Analysis and mapping of mutations in the five selected variants onto x-ray crystallography derived protein structures of the AAV5 VP3 protein gave additional insights into the roles the mutations were playing in increasing liver transduction. Table 2 summarizes the location of the amino acid differences between the various mutants and wt-AAV5 and their most probable mechanism of increasing infectivity in liver cells.

TABLE 2

Mutations of AAV5 Variants with Increased Liver Tropism

| Variant | Mutation | Region/Probable Function |
|---|---|---|
| MV1 | G257R | Surface Exposed in VR-I/Loop1 Region, Increases Binding and Internalization |
| | F417L | Buried in Interior of Capsid, Affects Stability of Capsid and Perhaps Uncoating |
| MV18 | G257R | Surface Region in VR-I/Loop1, Increases Binding and Internalization |
| MV20 | P200S | |
| | M469I | |
| | A579T | Surface Exposed in VR-VIII/Loop 8 Region, Near Sialic Acid Binding Pocket and Increases Binding |
| MV50 | G257R | Surface Region in VR-I/Loop1, Increases Binding and Internalization |
| | S705G | Surface Mutation Near Known Antigenic Site |

TABLE 2-continued

Mutations of AAV5 Variants with Increased Liver Tropism

| Variant | Mutation | Region/Probable Function |
|---|---|---|
| MV53 | Q179R | Near VP2/VP3 Junction, Increases Binding, No Effect on Internalization |
| | G257R | Surface Region in VR-I/Loop1, Increases Binding and Internalization |

As mentioned before, four of the mutants, MV1, MV18, MV50, and MV53, contained a glycine to arginine mutation at amino acid 257 of the VP1 protein. This particular mutation is located in the variable region I (VRI), or otherwise known as Loop1, which is partially exposed on the surface of the intact 60mer AAV capsid. From the crystal structure of AAV5, amino acid 257 is purported to be a surface exposed amino acid within the VRI region. Binding assays performed by incubating virus with cells at 4° C. and quantitating bound vector genomes via RT-PCR revealed that the Loop1 mutation increased binding to the cell surface by a factor of 2.2 when compared to WT-AAV5 (FIG. 10). Subsequent internalization assays using the same procedure as the binding assay with an additional step of incubation at 37° C. for an hour showed that the percentage of bound virions that were internalized was increased by 3.1-fold for the Loop1 mutation versus WT-AAV5 (FIG. 11). The internalization assay additionally indicated an overall 7 times difference in total virus internalized between AAV5 and the Loop1 Mutant (FIG. 12), which was consistent with the difference in GFP expression reported previously. These results demonstrated that the Loop1 mutation increased receptor binding and internalization, but could not concretely establish which aspect of internalization was affected as the internalization assay only measured virus that entered the cell and did not account for location within the cell. The location of the Loop1 mutation in the VRI region suggests that it should not have any purpose in endosomal escape as the VP1u region of the VP1 protein is responsible for escaping the endosome. Additionally, because the fold change in overall amount of virus internalized and the fold change in GFP expression are consistent, we believe it suggests that that change in GFP expression is primarily due to an increase in overall amount of virus entering the cell, and less likely due increases in endosomal escape or cellular trafficking. If the primary increase in infectivity was due to an increase in endosomal escape or cellular trafficking, there would likely be a significantly smaller fold increase in overall virus internalized compared to the fold increase of GFP expression. For these reasons, we believe that the Loop1 mutation is primarily responsible for increasing binding to a receptor that internalizes more quickly compared to other receptors used by AAV5, thereby increasing the overall amount and rate of virus internalized. It is not clear whether the Loop1 mutation is increasing binding to an existing receptor or allowing binding of a different receptor that AAV5 previously did not target.

Mapping of the secondary mutations (non-Loop1R mutations) and comparison of binding and internalization against MV18 for MV1, MV20, MV50, and MV53 provided more insight into their possible functions. The secondary mutation for MV1 is located at amino acid 417 (F to L), which is not present on the surface of AAV5; instead it resides in the interior of the capsid. Thus, this mutation is unlikely to be affecting receptor binding, endosomal escape, or cellular trafficking, but rather a process further down such as uncoating of the viral capsid. Uncoating of the viral capsid has been reported by Thomas et al. (Journal of Virology 2004) to be a limiting step of gene expression in hepatocytes, and thus a potential increase in uncoating efficiency could lead to higher gene expression. Interestingly, the yield of variants containing the F to L mutation have noticeably lower yields compared to the rest of the variants, indicating a possible decrease in the stability of the capsid which could facilitate uncoating in the nucleus of the cells. Binding and internalization assays comparing MV18 and MV1 corroborate the previous theory as there are no significant differences in binding or internalization of the virus when the F417L mutation is added together with the Loop1 mutation (FIGS. 13, 14, 15), confirming that F417L does not affect binding or amount of virus that is internalized when compared to MV18. Because the F417L mutation does not affect binding or internalization, but still increases overall infectivity of the virus, the mutation most likely is affecting a process further downstream, and due to its location in the interior of the capsid, most likely influences uncoating of the capsid. Together, these data suggest that the likely mechanism for the F417L mutation is enhancing the uncoating of the viral capsid which then increases the total amount of vector genome in the nucleus then be transcribed into RNA.

Figure 10:
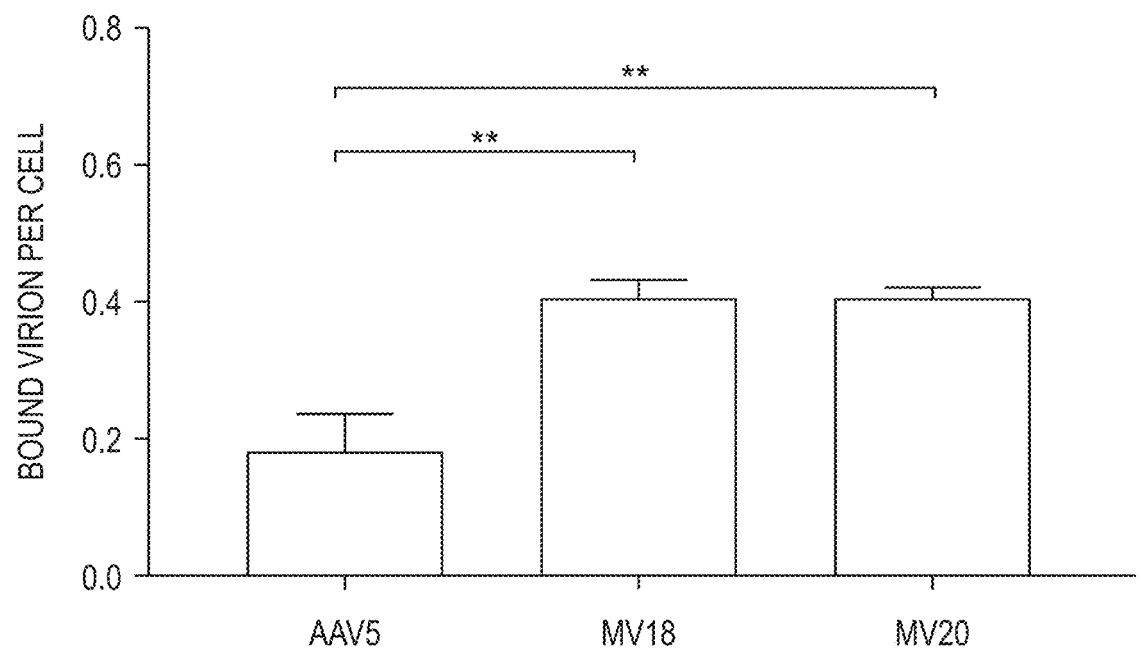
FIG. 10 depicts a quantitative comparison of binding to the cell surface between wild type AAV5, MV18, and MV20. Binding was determined by quantifying the vector genomes within the viral capsids that were bound to the surface of the cell via RT-PCR.
Figure 11:
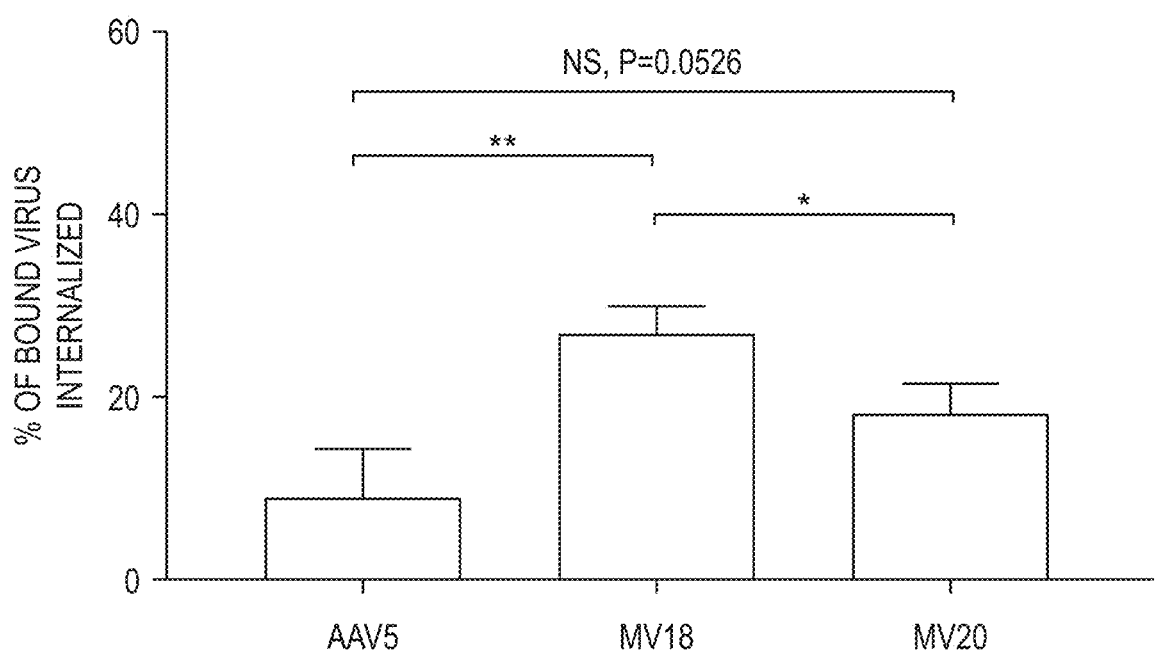
FIG. 11 depicts a quantitative comparison of the percentage of bound AAV particles that are internalized between AAV5, MV18, and MV20. The percentage of bound virions that are internalized was determined by dividing the overall amount of vector genomes within the cell by the overall number of bound virions on the cell surface. RT-PCR was used to quantify the vector genomes within the cell.
Figure 12:
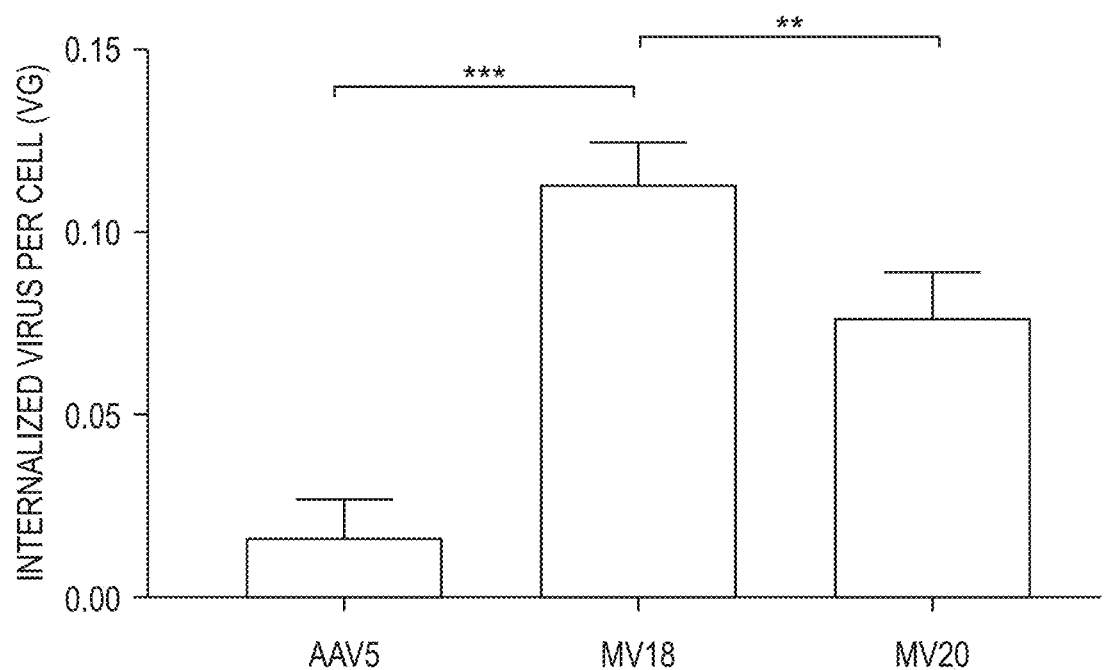
FIG. 12 depicts a quantitative comparison of the overall amount of AAV particles internalized by a cell between AAV5, MV18, and MV20. Internalization is measured by quantifying the vector genomes within the viral capsids that are within the cell via RT-PCR.

MV20 is the sole isolated variant that does not contain the Loop1R mutation; instead, there is a three amino acid difference compared to WT-AAV5. Of note, MV20 contains a mutation of alanine to threonine at position 579, which is located in Variable Region VIII (VR-VIII) that contains amino acids critical for binding of sialic acid. Interestingly, MV20 exhibits binding comparable to MV18, roughly a 2.2-fold increase when compared to AAV5 (FIG. 10). However, the A579T mutation only increases the percentage of bound virions that are internalized by roughly 2-fold compared to AAV5 (FIG. 11). As such, the A579T mutation seems to be increasing binding, but is not as effective at increasing internalization when compared to the Loop1 mutation. This indicates that the receptors that are engaged by MV18 and MV20 are different, and perhaps for MV20 the increase in binding is against an attachment factor such as sialic acid, but still relies on a different receptor for internalization and as such results in lower internalization when compared to the Loop1 mutation. A similar mutation was discovered through direction evolution by Excoffon et al. (PNAS, 2009) that was located at amino acid 581 and similarly was an alanine to threonine mutation that was reported to play a role in sialic acid recognition and binding. As such, it is plausible that the alanine to threonine mutation at amino acid 579 is performing a similar function to increase sialic acid binding as the same mutation at amino acid 581 that Excoffon et al. discovered.

Figure 13:
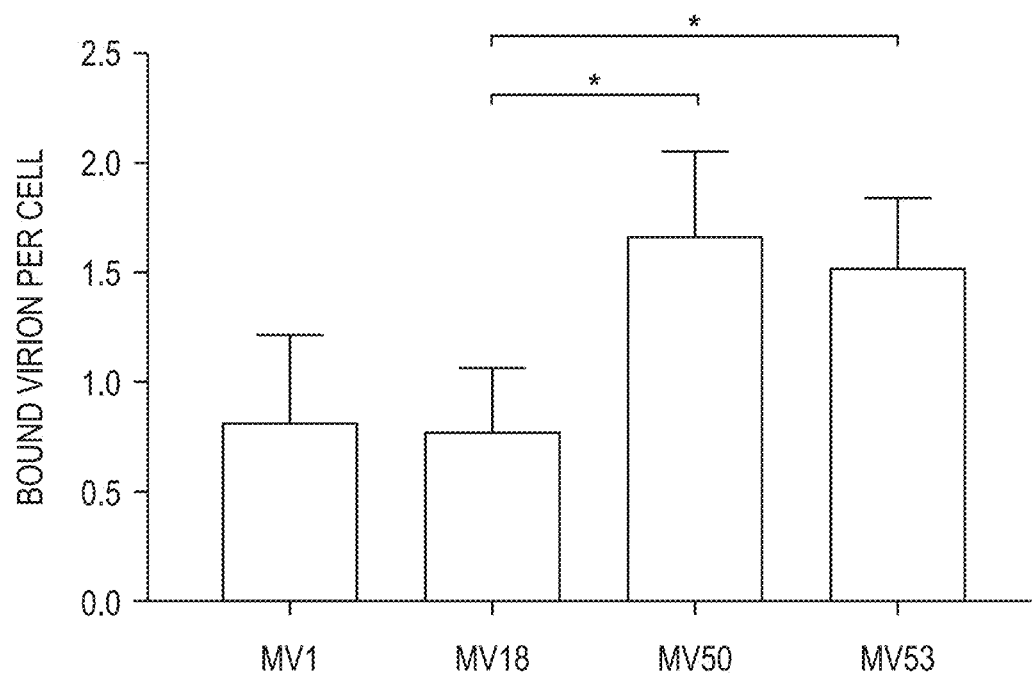
FIG. 13 depict a quantitative comparison of binding to the cell surface between wild type MV18, MV1, MV50, and MV53. Binding was determined by quantifying the vector genomes within the viral capsids that were bound to the surface of the cell via RT-PCR.
Figure 14:
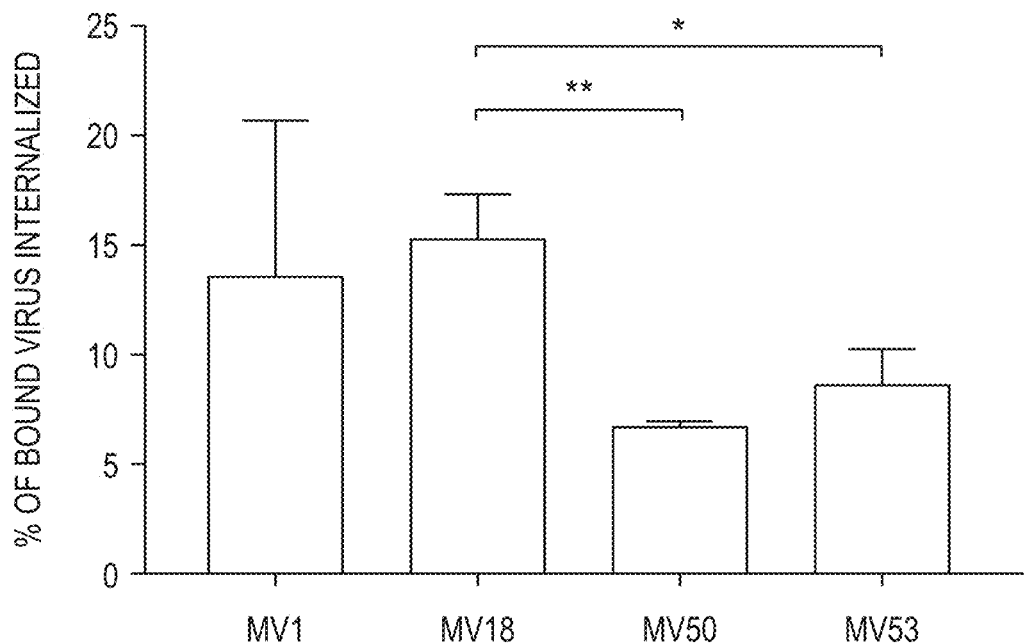
FIG. 14 depicts a quantitative comparison of the percentage of bound AAV particles that are internalized between MV18, MV1, MV50, and MV53. The percentage of bound virions that are internalized was determined by dividing the overall amount of vector genomes within the cell by the overall number of bound virions on the cell surface. RT-PCR was used to quantify the vector genomes within the cell.
Figure 15:
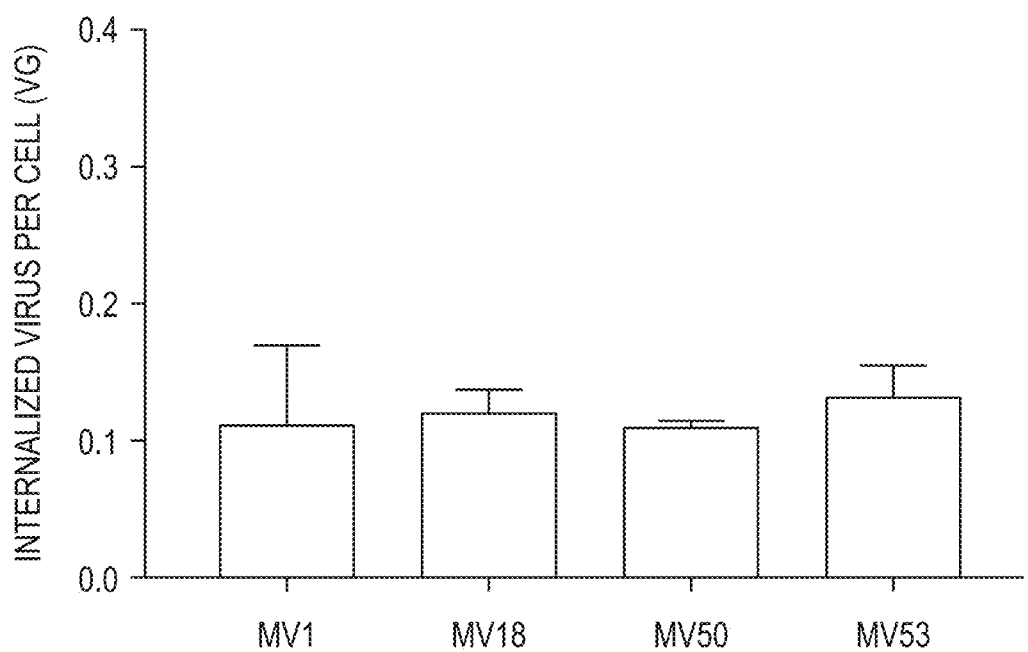
FIG. 15 depicts a quantitative comparison of the overall amount of AAV particles internalized by a cell between MV18, MV1, MV50, and MV53. Internalization is measured by quantifying the vector genomes within the viral capsids that are within the cell via RT-PCR.

In addition to the Loop1R mutation, MV50 contains a serine to glycine mutation at position 705. The exact function of the region surrounding amino acid 705 is not clearly understood, but a group has reported nearby amino acid 711 to be involved in sialic acid binding (Afione et al., Journal of Virology, 2014). Additionally, the region has also been shown to be an antigenic site for antibody recognition. Using protein crystal structure of the AAV5 capsid, we found that amino acid 705 is exposed on the surface of the capsid, and thus perhaps is involved with binding of the virus to the cell. A binding assay comparing MV18 and MV50 confirmed that the S705G mutation further increased binding to the cell surface around 2-fold over the Loop1 mutation alone (FIG. 13). Interestingly, the percentage of bound virions that were internalized decreased significantly when comparing MV50 and MV18, indicating that the increased binding did not correlate to increased percentage of internalized virus (FIG. 14). Additionally, no difference between overall amount of virus internalized was observed between MV50 and MV18, signaling that the Loop1 mutation and its receptor are likely the main driver for the increase in the bound virus being internalized and increases in binding through the S705G mutation does not affect the internalization rate (FIG. 15). As such, we can conclude that S705G likely increases infectivity by only increasing binding to an attachment factor that allows for more virus to associate with the surface of the cell and subsequently be internalized through the Loop1 mutation pathway. This would also explain why the percentage of bound virus internalized decreased as the Loop1 mutation is mainly responsible for internalization. There is likely no difference in the overall amount of internalized virus due to the static environment of the binding and internalization assays where receptor turnover and subsequent binding of new virions is not considered.

Lastly, the secondary mutation of MV53 is a glutamine to arginine mutation at amino acid 179 (Q179R) which is located near the junction of the VP2 and VP3. This region has not been well described in literature due to the difficulty in resolving the crystal structure of this region. The exact function of this region has not been determined, although there have been nuclear localization signals located elsewhere in the VP2 protein. However, we believe the junction of VP2/VP3 region is present on the surface of the AAV capsid and does indeed play a role in AAV transduction. To add support for this theory, we performed a binding and internalization assay comparing MV18 and MV53 and found that the Q179R mutation increased the number of virions bound to the cell surface when compared to MV18 (FIG. 13). However, similar to MV50, the percentage of bound virions decreased significantly, and overall amount of internalized virus remained consistent with MV18 (FIGS. 14, 15), suggesting that MV53 is similar to MV50 in that the Q179R mutation likely only influences binding to an attachment factor on the cell surface and does not influence internalization. Additionally, these data also show that although the VP2/VP3 is not resolvable by x-ray crystallography, its structure is likely on or near the surface of the capsid and plays a role in binding to the cell membrane.

Figure 16:
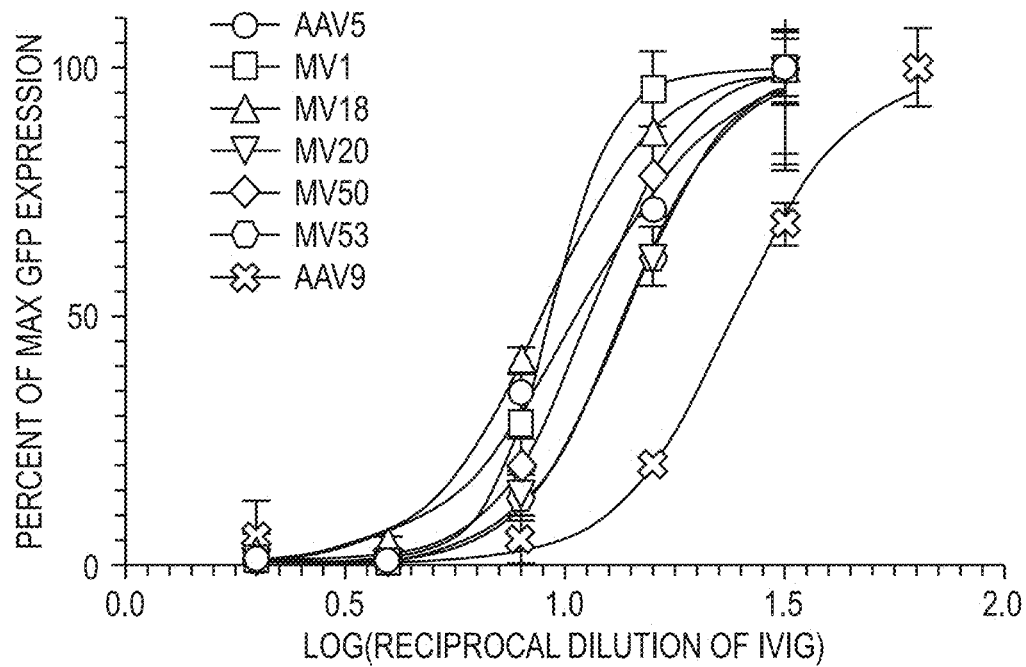
FIG. 16 depicts a comparison of the seroreactivity of wt-AAV5 and AAV5 mutants against intravenous immunoglobulin (IVIG). The seroreactivity curves are generated by plotting the percent of max GFP expression for each virus (as compared to virus incubated with PBS instead of IVIG) against the log reciprocal dilution used. Nonlinear curve fitting of the plotted points generated exponential curves that could be used to compare seroreactivity of each virus against IVIG.
Figure 17:
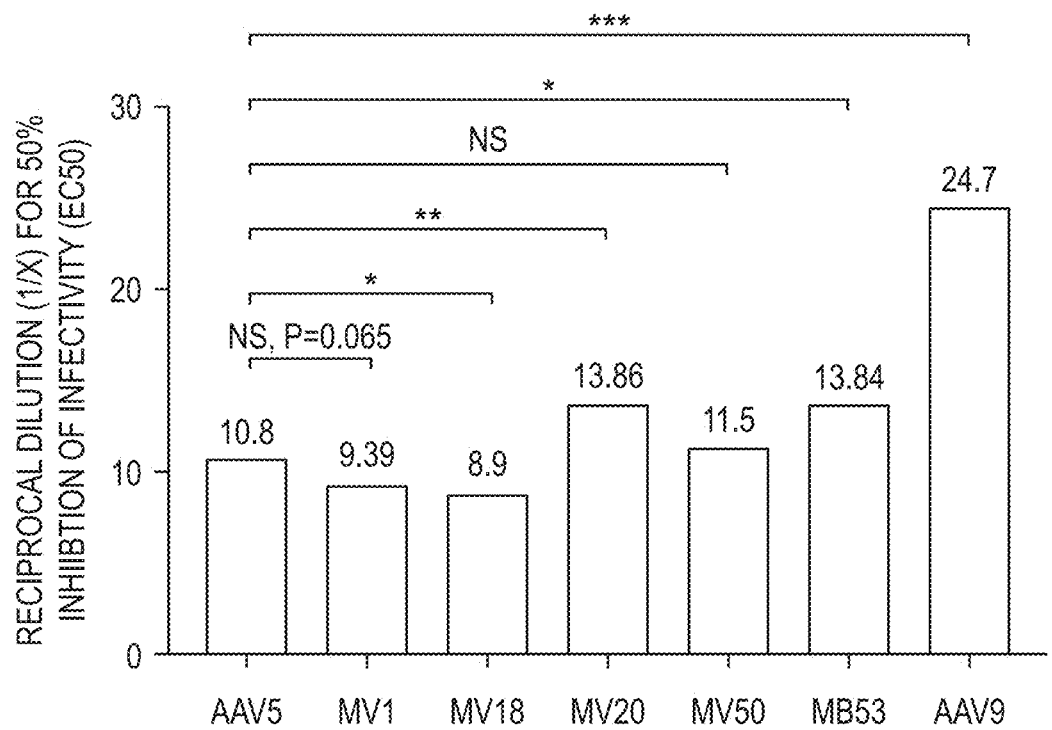
FIG. 17 depicts a comparison of the calculated EC50 from the curves in FIG. 16. The EC50 for each virus was determined as the reciprocal dilution of IVIG that would inhibit 50% of viral transduction.

Next, we determined the reactivity of the mutant capsids to human neutralizing factors via a seroreactivity assay that utilizes intravenous immunoglobulin (IVIG), or pooled immunoglobulin G from thousands of donors, to represent the overall prevalence of neutralizing antibodies against specific antigens in the overall human population. We compared our mutant viruses to two control serotypes, AAV5 and AAV9; one with very low prevalence of neutralizing antibodies (5%), and one with a medium (30%-40%) prevalence (Boutin et al., Human Gene Therapy 2010). AAV capsids that have higher prevalence of neutralizing antibodies in the human population will be neutralized at higher reciprocal dilutions, or with lower amounts of IVIG, and vice versa for AAV capsids with lower prevalence of neutralizing antibodies. Mutant viruses containing GFP reporter transgenes were incubated with increasing reciprocal dilutions, or two-fold dilutions, of IVIG for 1 hour and then added to individual wells of Huh7 cells in a 96 well plate. Virus concentration was kept the same for each reciprocal dilution of IVIG. Wild-type adenovirus was also added to each well at a MOI of 50 to facilitate AAV transgene expression. After 72 hours, the cells in each well were lysed and the crude lysate was assayed for GFP activity. The GFP activity was measured against a control well infected with only virus and no IVIG to obtain the percent of max GFP expression at each reciprocal dilution for each virus. Plotting the percent max of GFP against the log reciprocal dilution and curve fitting using nonlinear regression allowed for the comparison of seroreactivity between different viruses. From these curves, we determined that the seroreactivity of AAV5 and the MV mutants are fairly consistent with each other, and all of which are significantly shifted to the left of AAV9, indicating that AAV5 and the mutants require more IVIG to neutralize their infectivity when compared to AAV9 (FIG. 16). This signifies that the IVIG contains a higher titer of anti-AAV9 neutralizing antibodies, and thereby indicating that the donor population has a higher prevalence of anti-AAV9 antibodies compared to anti-AAV5 antibodies. The seroreactivity curve for MV18, or the mutant with only the Loop1 mutation, is shifted to the left of AAV5, signifying that MV18 is slightly less seroreactive than AAV5 and requires slightly more IVIG to achieve 50% inhibition of infectivity (FIGS. 16, 17). MV1 is very similar to MV18 in terms of seroreactivity towards IVIG, whereas MV20 and MV53 are slightly more seroreactive when compared to AAV5 (FIG. 17). MV50 is the closest variant to AAV5 that does not differ in seroreactivity in comparison to AAV5. Although the seroreactivity of the mutants towards IVIG seems to slightly vary in comparison to AAV5, the prevalence of antibodies against the mutants in the human population is unlikely to be any different when compared to AAV5. This is largely because all the mutations found from the selection process are all de novo mutations and do not exist in any other serotype. Coupled with the fact that the AAV5 is the most genetically divergent AAV serotype, it is extremely unlikely for any human to have been infected previously by these mutants and thus have developed neutralizing antibodies specifically targeting these de novo mutations. It is far more likely that the existing antibodies that already target AAV5 are interfering with the mutations ability to carry out their functions perhaps through steric hindrance of the region the mutation resides in. As such, we have concluded that the mutant AAV5 viruses are fairly consistent in terms of seroreactivity towards IVIG compared to AAV5, particularly compared to other serotypes such as AAV9, and additionally the overall prevalence of neutralizing factors in the human population against the mutants is likely to be very similar to AAV5.

Example 4

Characterization of AAV5 Mutants in Primary Human Liver Cells

Figure 18:
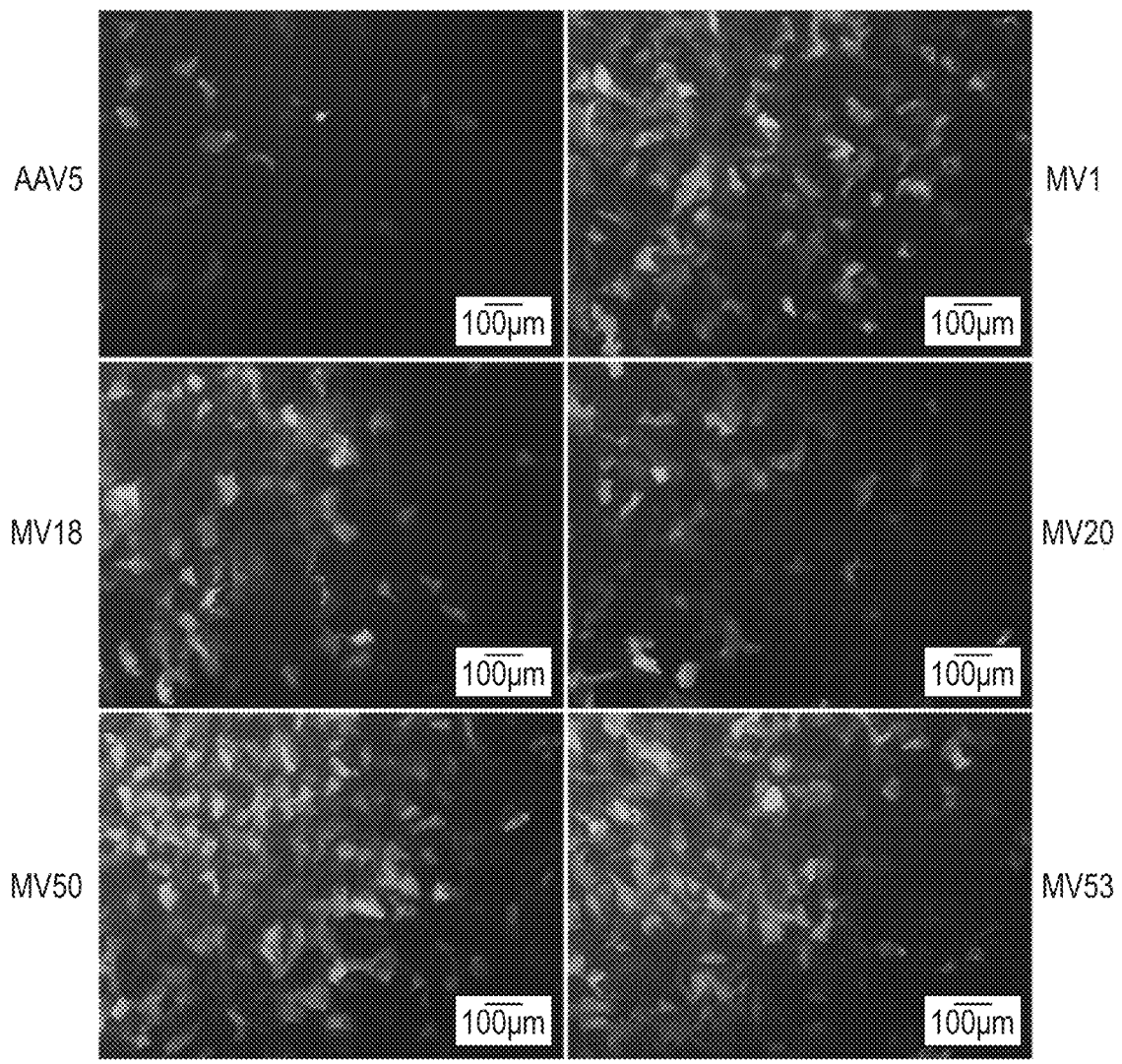
FIG. 18 depicts a comparison of green fluorescent protein (GFP) expression in primary human hepatocytes after infection by wild type AAV5 or AAV5 mutants packaged with GFP reporter gene. Primary human hepatocytes were infected with a MOI of $5 \times 10^5$ vector genomes per cell. Images were taken 72 hours post infection with a fluorescent microscope.
Figure 19:
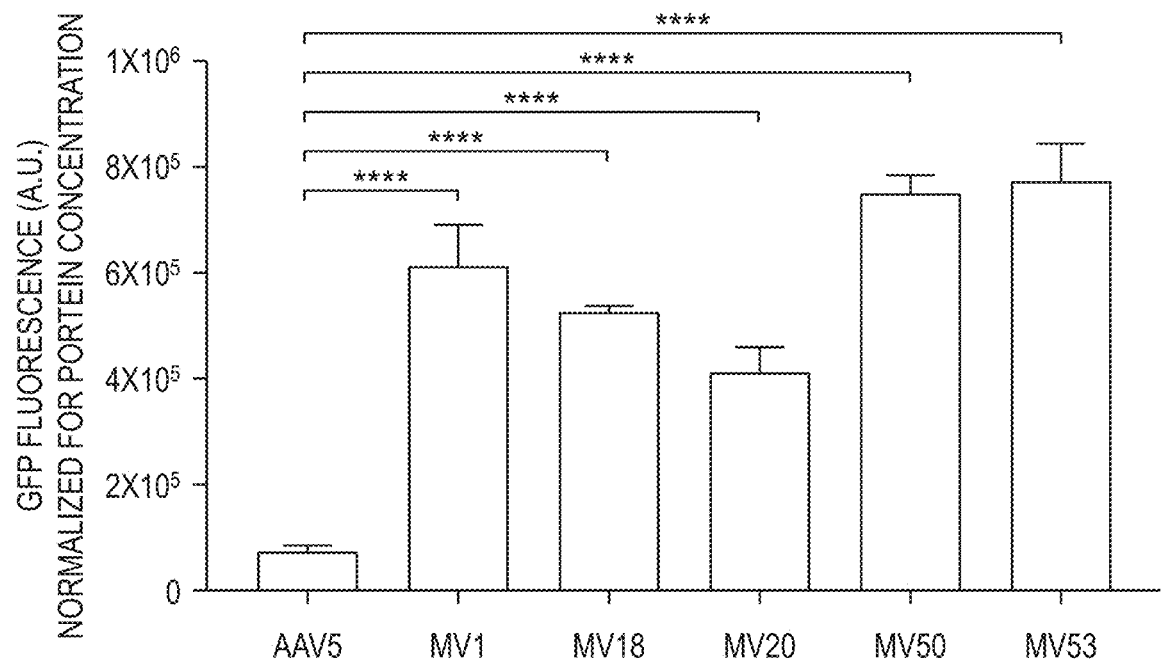
FIG. 19 depict a quantitative comparison of GFP expression in primary human hepatocytes cells after infection by wild type AAV5 or AAV5 mutants packaged with GFP reporter gene. Primary human hepatocytes were infected with a MOI of $5 \times 10^5$ vector genomes per cell. Cells were lysed 72 hours post infection and quantified with a fluorometric GFP quantification kit from Cell Bio Labs.
Figure 20:
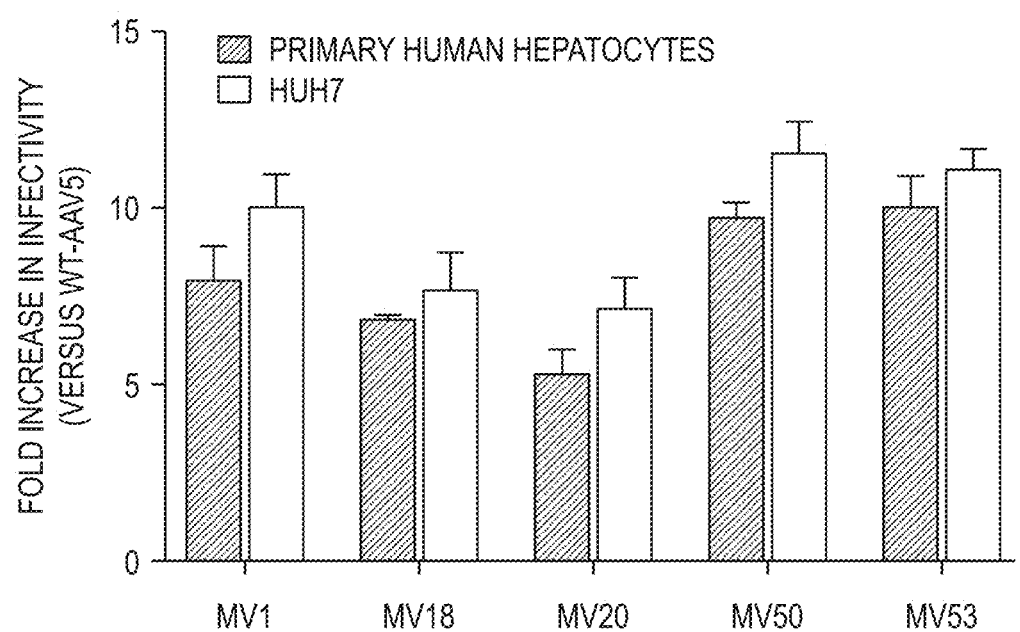
FIG. 20 depicts a comparison of the fold increases in infectivity of the AAV5 mutants over AAV5 in Huh7 cells and primary human hepatocytes.

The five AAV5 mutants were tested for their transduction capabilities in primary human hepatocytes in order to verify that their increased infectivity in Huh7 cells was translatable to human liver cells. Primary human hepatocytes were plated and infected with purified sc-GFP vectors at a MOI of 500,000 vg per cell. Seventy-two hours post-infection, the cells were taken for imaging of GFP expression and quantification of GFP activity. Similar to the results from Huh7 cells, the AAV5 mutants were all significantly better at infecting primary human hepatocytes when compared with wt-AAV5 (FIG. 18). In particular, MV50 and MV53 were the two variants with the best transduction capabilities and both infected primary human hepatocytes roughly 10-fold better compared to AAV5, which was very consistent with the fold increase in Huh7 cells (FIG. 19). The increase in infectivity of the other three mutants, MV1, MV18, and MV20 over AAV5 were also very consistent with the results from Huh7 cells, with the fold increase over AAV5 around 8-fold, 7-fold, and 5-fold, respectively (FIG. 20). The overall magnitude of the fold increases in infectivity in primary human hepatocytes were very consistent when compared to the results from Huh7 cells (FIG. 20), indicating that Huh7 cells and primary human hepatocytes are very similar in terms of characteristics influencing AAV infectivity, and also demonstrates the viability of using Huh7 cells to approximate infectivity in human liver cells. Overall, these results demonstrate that directed evolution of AAV5 yields mutants that have significantly increased infectivity in primary human hepatocytes while retaining the favorable seroreactivity of AAV5, and thus substantiates the possibility of translating these low seroreactive capsids for use in human liver diseases.

The foregoing is illustrative of the present invention, and is not to be construed as limiting thereof. The invention is defined by the following claims, with equivalents of the claims to be included therein.

```
Sequences
SEQ ID NO: 1-MV1
ATGTCTTTTGTTGATCACCCTCCAGATTGGTTGGAAGAAGTTGGTGAAGG

TCTTCGCGAGTTTTTGGGCCTTGAAGCGGGCCCACCGAAACCAAAACCCA

ATCAGCAGCATCAAGATCAAGCCCGTGGTCTTGTGCTGCCTGGTTATAAC

TATCTCGGACCCGGAAACGGTCTCGATCGAGGAGAGCCTGTCAACAGGGC

AGACGAGGTCGCGCGAGAGCACGACATCTCGTACAACGAGCAGCTTGAGG

CGGGAGACAACCCCTACCTCAAGTACAACCACGCGGACGCCGAGTTTCAG

GAGAAGCTCGCCGACGACACATCCTTCGGGGGAAACCTCGGAAAGGCAGT

CTTTCAGGCCAAGAAAAGGGTTCTCGAACCTTTTGGCCTGGTTGAAGAGG

GTGCTAAGACGGCCCCTACCGGAAAGCGGATAGACGACCACTTTCCAAAA

AGAAAGAAGGCTCGGACCGAAGAGGACTCCAAGCCTTCCACCTCGTCAGA

CGCCGAAGCTGGACCCAGCGGATCCCAGCAGCTGCAAATCCCAGCCCAAC

CAGCCTCAAGTTTGGGAGCTGATACAATGTCTGCGGGAGGTGGCGGCCCA

TTGGGCGACAATAACCAAGGTGCCGATGGAGTGGGCAATGCCTCGGGAGA

TTGGCATTGCGATTCCACGTGGATGGGGGACAGAGTCGTCACCAAGTCCA

CCCGAACCTGGGTGCTGCCCAGCTACAACAACCACCAGTACCGAGAGATC

AAAAGCGGCTCCGTCGACAGAAGCAACGCCAACGCCTACTTTGGATACAG

CACCCCCTGGGGGTACTTTGACTTTAACCGCTTCCACAGCCACTGGAGCC

CCCGAGACTGGCAAAGACTCATCAACAACTACTGGGGCTTCAGACCCCGG

TCCCTCAGAGTCAAAATCTTCAACATTCAAGTCAAAGAGGTCACGGTGCA

GGACTCCACCACCACCATCGCCAACAACCTCACCTCCACCGTCCAAGTGT

TTACGGACGACGACTACCAGCTGCCCTACGTCGTCGGCAACGGGACCGAG

GGATGCCTGCCGGCCTTCCCTCCGCAGGTCTTTACGCTGCCGCAGTACGG

TTACGCGACGCTGAACCGCGACAACACAGAAAATCCCACCGAGAGGAGCA

GCTTCTTCTGCCTAGAGTACTTTCCCAGCAAGATGCTGAGAACGGGCAAC

AACTTTGAGTTTACCTACAACTTTGAGGAGGTGCCCTTCCACTCCAGCCT

CGCTCCCAGTCAGAACCTCTTCAAGCTGGCCAACCCGCTGGTGGACCAGT

ACTTGTACCGCTTCGTGAGCACAAATAACACTGGCGGAGTCCAGTTCAAC

AAGAACCTGGCCGGGAGATACGCCAACACCTACAAAAACTGGTTCCCGGG

GCCCATGGGCCGAACCCAGGGCTGGAACCTGGGCTCCGGGGTCAACCGCG

CCAGTGTCAGCGCCTTCGCCACGACCAATAGGATGGAGCTCGAGGGCGCG
```

-continued

AGTTACCAGGTGCCCCCGCAGCCGAACGGCATGACCAACAACCTCCAGGG

CAGCAACACCTATGCCCTGGAGAACACTATGATCTTCAACAGCCAGCCGG

CGAACCCGGGCACCACCGCCACGTACCTCGAGGGCAACATGCTCATCACC

AGCGAGAGCGAGACGCAGCCGGTGAACCGCGTGGCTTACAACGTCGGCGG

GCAGATGGCCACCAACAACCAGAGCTCCACCACTGCCCCCGCGACCGGCA

CGTACAACCTCCAGGAAATCGTGCCCGGCAGCGTGTGGATGGAGAGGGAC

GTGTACCTCCAAGGACCCATCTGGGCCAAGATCCCAGAGACGGGGGCGCA

CTTTCACCCCTCTCCGGCCATGGGCGGATTCGGACTCAAACACCCACCGC

CCATGATGCTCATCAAGAACACGCCTGTGCCCGGAAATATCACCAGCTTC

TCGGACGTGCCCGTCAGCAGCTTCATCACCCAGTACAGCACCGGGCAGGT

CACCGTGGAGATGGAGTGGGAGCTCAAGAAGGAAAACTCCAAGAGGTGGA

ACCCCGAGATCCAGTACACAAACAACTACAACGACCCCCAGTTTGTGGAC

TTTGCCCCGGACAGCACCGGGGAATACAGAAGCACCAGACCTATCGGAAC

CCGATACCTTACCCGACCCCTTTAA

SEQ ID NO: 2-MV1
MSFVDHPPDWLEEVGEGLREFLGLEAGPPKPKPNQQHQDQARGLVLPGYN
YLGPGNGLDRGEPVNRADEVAREHDISYNEQLEAGDNPYLKYNHADAEFQ
EKLADDTSFGGNLGKAVFQAKKRVLEPFGLVEEGAKTAPTGKRIDDHFPK
RKKARTEEDSKPSTSSDAEAGPSGSQQLQIPAQPASSLGADTMSAGGGGP
LGDNNQGADGVGNASGDWHCDSTWMGDRVVTKSTRTWVLPSYNNHQYREI
KSGSVDRSNANAYFGYSTPWGYFDFNRFHSHWSPRDWQRLINNYWGFRPR
SLRVKIFNIQVKEVTVQDSTTTIANNLTSTVQVFTDDDYQLPYVVGNGTE
GCLPAFPPQVFTLPQYGYATLNRDNTENPTERSSFFCLEYFPSKMLRTGN
NFEFTYNFEEVPFHSSLAPSQNLFKLANPLVDQYLYRFVSTNNTGGVQFN
KNLAGRYANTYKNWFPGPMGRTQGWNLGSGVNRASVSAFATTNRMELEGA
SYQVPPQPNGMTNNLQGSNTYALENTMIFNSQPANPGTTATYLEGNMLIT
SESETQPVNRVAYNVGGQMATNNQSSTTAPATGTYNLQEIVPGSVWMERD
VYLQGPIWAKIPETGAHFHPSPAMGGFGLKHPPPMMLIKNTPVPGNITSF
SDVPVSSFITQYSTGQVTVEMEWELKKENSKRWNPEIQYTNNYNDPQFVD
FAPDSTGEYRSTRPIGTRYLTRPL

SEQ ID NO: 3-MV18
ATGTCTTTTGTTGATCACCCTCCAGATTGGTTGGAAGAAGTTGGTGAAGG
TCTTCGCGAGTTTTTGGGCCTTGAAGCGGGCCCACCGAAACCAAAACCCA
ATCAGCAGCATCAAGATCAAGCCCGTGGTCTTGTGCTGCCTGGTTATAAC
TATCTCGGACCCGGAAACGGTCTCGATCGAGGAGAGCCTGTCAACAGGGC
AGACGAGGTCGCGCGAGAGCACGACATCTCGTACAACGAGCAGCTTGAGG
CGGGAGACAACCCCTACCTCAAGTACAACCACGCGGACGCCGAGTTTCAG
GAGAAGCTCGCCGACGACACATCCTTCGGGGGAAACCTCGGAAAGGCAGT
CTTTCAGGCCAAGAAAAGGGTTCTCGAACCTTTTGGCCTGGTTGAAGAGG
GTGCTAAGACGGCCCCTACCGGAAAGCGGATAGACGACCACTTTCCAAAA
AGAAAGAAGGCTCGGACCGAAGAGGACTCCAAGCCTTCCACCTCGTCAGA

CGCCGAAGCTGGACCCAGCGGATCCCAGCAGCTGCAAATCCCAGCCCAAC

CAGCCTCAAGTTTGGGAGCTGATACAATGTCTGCGGGAGGTGGCGGCCCA

TTGGGCGACAATAACCAAGGTGCCGATGGAGTGGGCAATGCCTCGGGAGA

TTGGCATTGCGATTCCACGTGGATGGGGGACAGAGTCGTCACCAAGTCCA

CCCGAACCTGGGTGCTGCCCAGCTACAACAACCACCAGTACCGAGAGATC

AAAAGCGGCTCCGTCGACAGAAGCAACGCCAACGCCTACTTTGGATACAG

CACCCCCTGGGGGTACTTTGACTTTAACCGCTTCCACAGCCACTGGAGCC

CCCGAGACTGGCAAAGACTCATCAACAACTACTGGGGCTTCAGACCCCGG

TCCCTCAGAGTCAAAATCTTCAACATTCAAGTCAAAGAGGTCACGGTGCA

GGACTCCACCACCACCATCGCCAACAACCTCACCTCCACCGTCCAAGTGT

TTACGGACGACGACTACCAGCTGCCCTACGTCGTCGGCAACGGGACCGAG

GGATGCCTGCCGGCCTTCCCTCCGCAGGTCTTTACGCTGCCGCAGTACGG

TTACGCGACGCTGAACCGCGACAACACAGAAAATCCCACCGAGAGGAGCA

GCTTCTTCTGCCTAGAGTACTTTCCCAGCAAGATGCTGAGAACGGGCAAC

AACTTTGAGTTTACCTACAACTTTGAGGAGGTGCCCTTCCACTCCAGCTT

CGCTCCCAGTCAGAACCTGTTCAAGCTGGCCAACCCGCTGGTGGACCAGT

ACTTGTACCGCTTCGTGAGCACAAATAACACTGGCGGAGTCCAGTTCAAC

AAGAACCTGGCCGGGAGATACGCCAACACCTACAAAAACTGGTTCCCGGG

GCCCATGGGCCGAACCCAGGGCTGGAACCTGGGCTCCGGGGTCAACCGCG

CCAGTGTCAGCGCCTTCGCCACGACCAATAGGATGGAGCTCGAGGGCGCG

AGTTACCAGGTGCCCCCGCAGCCGAACGGCATGACCAACAACCTCCAGGG

CAGCAACACCTATGCCCTGGAGAACACTATGATCTTCAACAGCCAGCCGG

CGAACCCGGGCACCACCGCCACGTACCTCGAGGGCAACATGCTCATCACC

AGCGAGAGCGAGACGCAGCCGGTGAACCGCGTGGCTTACAACGTCGGCGG

GCAGATGGCCACCAACAACCAGAGCTCCACCACTGCCCCCGCGACCGGCA

CGTACAACCTCCAGGAAATCGTGCCCGGCAGCGTGTGGATGGAGAGGGAC

GTGTACCTCCAAGGACCCATCTGGGCCAAGATCCCAGAGACGGGGGCGCA

CTTTCACCCCTCTCCGGCCATGGGCGGATTCGGACTCAAACACCCACCGC

CCATGATGCTCATCAAGAACACGCCTGTGCCCGGAAATATCACCAGCTTC

TCGGACGTGCCCGTCAGCAGCTTCATCACCCAGTACAGCACCGGGCAGGT

CACCGTGGAGATGGAGTGGGAGCTCAAGAAGGAAAACTCCAAGAGGTGGA

ACCCAGAGATCCAGTACACAAACAACTACAACGACCCCCAGTTTGTGGAC

TTTGCCCCGGACAGCACCGGGGAATACAGAACCACCAGACCTATCGGAAC

CCGATACCTTACCCGACCCCTTTAA

SEQ ID NO: 4-MV18
MSFVDHPPDWLEEVGEGLREFLGLEAGPPKPKPNQQHQDQARGLVLPGYN
YLGPGNGLDRGEPVNRADEVAREHDISYNEQLEAGDNPYLKYNHADAEFQ
EKLADDTSFGGNLGKAVFQAKKRVLEPFGLVEEGAKTAPTGKRIDDHFPK
RKKARTEEDSKPSTSSDAEAGPSGSQQLQIPAQPASSLGADTMSAGGGGP
LGDNNQGADGVGNASGDWHCDSTWMGDRVVTKSTRTWVLPSYNNHQYREI
KSGSVDRSNANAYFGYSTPWGYFDFNRFHSHWSPRDWQRLINNYWGFRPR

```
SLRVKIFNIQVKEVTVQDSTTTIANNLTSTVQVFTDDDYQLPYVVGNGTE
GCLPAFPPQVFTLPQYGYATLNRDNTENPTERSSFFCLEYFPSKMLRTGN
NFEFTYNFEEVPFHSSFAPSQNLFKLANPLVDQYLRFVSTNNTGGVQFN
KNLAGRYANTYKNWFPGPMGRTQGWNLGSGVNRASVSAFATTNRMELEGA
SYQVPPQPNGMTNNLQGSNTYALENTMIFNSQPANPGTTATYLEGNMLIT
SESETQPVNRVAYNVGGQMATNNQSSTTAPATGTYNLQEIVPGSVWMERD
VYLQGPIWAKIPETGAHFHPSPAMGGFGLKHPPPMMLIKNTPVPGNITSF
SDVPVSSFITQYSTGQVTVEMEWELKKENSKRWNPEIQYTNNYNDPQFVD
FAPDSTGEYRTTRPIGTRYLTRPL
SEQ ID NO: 5-MV20
ATGTCTTTTGTTGATCACCCTCCAGATTGGTTGGAAGAAGTTGGTGAAGG
TCTTCGCGAGTTTTTGGGCCTTGAAGCGGGCCCACCGAAACCAAACCCA
ATCAGCAGCATCAAGATCAAGCCCGTGGTCTTGTGCTGCCTGGTTATAAC
TATCTCGGACCCGGAAACGGTCTCGATCGAGGAGAGCCTGTCAACAGGGC
AGACGAGGTCGCGCGAGAGCACGACATCTCGTACAACGAGCAGCTTGAGG
CGGGAGACAACCCCTACCTCAAGTACAACCACGCGGACGCCGAGTTTCAG
GAGAAGCTCGCCGACGACACATCCTTCGGGGGAAACCTCGGAAAGGCAGT
CTTTCAGGCCAAGAAAAGGGTTCTCGAACCTTTTGGCCTGGTTGAAGAGG
GTGCTAAGACGGCCCCTACCGGAAAGCGGATAGACGACCACTTTCCAAAA
AGAAAGAAGGCTCGGACCGAAGAGGACTCCAAGCCTTCCACCTCGTCAGA
CGCCGAAGCTGGACCCAGCGGATCCCAGCAGCTGCAAATCCCAGCCCAAC
CAGCCTCAAGTTTGGGAGCTGATACAATGTCTGCGGGAGGTGGCGGCTCA
TTGGGCGACAATAACCAAGGTGCCGATGGAGTGGGCAATGCCTCGGGAGA
TTGGCATTGCGATTCCACGTGGATGGGGGACAGAGTCGTCACCAAGTCCA
CCCGAACCTGGGTGCTGCCCAGCTACAACAACCACCAGTACCGAGAGATC
AAAAGCGGCTCCGTCGACGGAAGCAACGCCAACGCCTACTTTGGATACAG
CACCCCCTGGGGGTACTTTGACTTTAACCGCTTCCACAGCCACTGGAGCC
CCCGAGACTGGCAAAGACTCATCAACAACTACTGGGGCTTCAGACCCCGG
TCCCTCAGAGTCAAAATCTTCAACATTCAAGTCAAAGAGGTCACGGTGCA
GGACTCCACCACCACCATCGCCAACAACCTCACCTCCACCGTCCAAGTGT
TTACGGACGACGACTACCAGCTGCCCTACGTCGTCGGCAACGGGACCGAG
GGATGCCTGCCGGCCTTCCCTCCGCAGGTCTTTACGCTGCCGCAGTACGG
TTACGCGACGCTGAACCGCGACAACACAGAAAATCCCACCGAGAGGAGCA
GCTTCTTCTGCCTAGAGTACTTTCCCAGCAAGATGCTGAGAACGGGCAAC
AACTTTGAGTTTACCTACAACTTTGAGGAGGTGCCCTTCCACTCCAGCTT
CGCTCCCAGTCAGAACCTCTTCAAGCTGGCCAACCCGCTGGTGGACCAGT
ACTTGTACCGCTTCGTGAGCACAAATAACACTGGCGGAGTCCAGTTCAAC
AAGAACCTGGCCGGGAGATA*T*GCCAACACCTACAAAAACTGGTTCCCGGG
GCCCATA*G*GCCGAACCCAGGGCTGGAACCTGGGCTCCGGGGTCAACCGCG
CCAGTGTCAGCGCCTTCGCCACGACCAATAGGATGGAGCTCGAGGGCGCA
AGTTACCAGGTGCCCCCGCAGCCGAACGGCATGACCAACAACCTCCAGGG
```

```
CAGCAACACCTATGCCCTGGAGAACACTATGATCTTCAACAGCCAGCCGG
CGAACCCGGGCACCACCGCCACGTACCTCGAGGGCAACATGCTCATCACC
AGCGAGAGCGAGACGCAGCCGGTGAACCGCGTGGCGTACAACGTCGGCGG
GCAGATGGCCACCAACAACCAGAGCTCCACCACTACCCCCGCGACCGGCA
CGTACAACCTCCAGGAAATCGTGCCCGGCAGCGTGTGGATGGAGAGGGAC
GTGTACCTCCAAGGACCCATCTGGGCCAAGATCCCAGAGACGGGGGCGCA
CTTTCACCCCTCTCCGGCCATGGGCGGATTCGGACTCAAACACCCACCGC
CCATGATGCTCATCAAGAACACGCCTGTGCCCGGAAATATCACCAGCTTC
TCGGACGTGCCCGTCAGCAGCTTCATCACCCAGTACAGCACCGGGCAGGT
CACTGTGGAGATGGAGTGGGAGCTCAAGAAGGAAAACTCCAAGAGGTGGA
ACCCAGAGATCCAGTACACAAACAACTACAACGACCCCCAGTTTGTGGAC
TTTGCCCCGGACAGCACCGGGGAATACAGAAGCACCAGACCTATCGGAAC
CCGATACCTTACCCGACCCCTTTAA
SEQ ID NO: 6-MV20
MSFVDHPPDWLEEVGEGLREFLGLEAGPPKPKPNQQHQDQARGLVLPGYN
YLGPGNGLDRGEPVNRADEVAREHDISYNEQLEAGDNPYLKYNHADAEFQ
EKLADDTSEGGNLGKAVFQAKKRVLEPFGLVEEGAKTAPTGKRIDDHFPK
RKKARTEEDSKPSTSSDAEAGPSGSQQLQIPAQPASSLGADTMSAGGG*S*
LGDNNQGADGVGNASGDWHCDSTWMGDRVVTKSTRTWVLPSYNNHQYREI
KSGSVDGSNANAYFGYSTPWGYFDENREHSHWSPRDWQRLINNYWGFRPR
SLRVKIFNIQVKEVTVQDSTTTIANNLTSTVQVFTDDDYQLPYVVGNGTE
GCLPAFPPQVFTLPQYGYATLNRDNTENPTERSSFFCLEYFPSKMLRTGN
NFEFTYNFEEVPFHSSFAPSQNLFKLANPLVDQYLRFVSTNNTGGVQFN
KNLAGRYANTYKNWFPGP*I*GRTQGWNLGSGVNRASVSAFATTNRMELEGA
SYQVPPQPNGMTNNLQGSNTYALENTMIFNSQPANPGTTATYLEGNMLIT
SESETQPVNRVAYNVGGQMATNNQSSTT*TP*ATGTYNLQEIVPGSVWMERD
VYLQGPIWAKIPETGAHFHPSPAMGGFGLKHPPPMMLIKNTPVPGNITSF
SDVPVSSFITQYSTGQVTVEMEWELKKENSKRWNPEIQYTNNYNDPQFVD
FAPDSTGEYRSTRPIGTRYLTRPL
SEQ ID NO: 7-MV50
ATGTCTTTTGTTGATCACCCTCCAGATTGGTTGGAAGAAGTTGGTGAAGG
TCTTCGCGAGTTTTTGGGCCTTGAAGCGGGCCCACCGAAACCAAACCCA
ATCAGCAGCATCAAGATCAAGCCCGTGGTCTTGTGCTGCCTGGTTATAAC
TATCTCGGACCCGGAAACGGTCTCGATCGAGGAGAGCCTGTCAACAGGGC
AGACGAGGTCGCGCGAGAGCACGACATCTCGTACAACGAGCAGCTTGAGG
CGGGAGACAACCCCTACCTCAAGTACAACCACGCGGACGCCGAGTTTCAG
GAGAAGCTCGCCGACGACACATCCTTCGGGGGAAACCTCGGAAAGGCAGT
CTTTCAGGCCAAGAAAAGGGTTCTCGAACCTTTTGGCCTGGTTGAAGAGG
GTGCTAAGACGGCCCCTACCGGAAAGCGGATAGACGACCACTTTCCAAAA
AGAAAGAAGGCTCGGACCGAAGAGGACTCCAAGCCTTCCACCTCGTCAGA
CGCCGAAGCTGGACCCAGCGGATCCCAGCAGCTGCAAATCCCAGCCCAAC
CAGCCTCAAGTTTGGGAGCTGATACAATGTCTGCGGGAGGTGGCGGCCCA
```

-continued

TTGGGCGACAATAACCAAGGTGCCGATGGAGTGGGCAATGCCTCGGGAGA
TTGGCATTGCGATTCCACGTGGATGGGGGACAGAGTCGTCACCAAGTCCA
CCCGAACCTGGGTGCTGCCCAGCTACAACAACCACCAGTACCGAGAGATC
AAAAGCGGCTCCGTCGACAGAAGCAACGCCAACGCCTACTTTGGATACAG
CACCCCCTGGGGGTACTTTGACTTTAACCGCTTCCACAGCCACTGGAGCC
CCCGAGACTGGCAAAGACTCATCAACAACTACTGGGGCTTCAGACCCCGG
TCCCTCAGAGTCAAAATCTTCAACATTCAAGTCAAAGAGGTCACGGTGCA
GGACTCCACCACCACCATCGCCAACAACCTCACCTCCACCGTCCAAGTGT
TTACGGACGACGACTACCAGCTGCCCTACGTCGTCGGCAACGGGACCGAG
GGATGCCTGCCGGCCTTCCCTCCGCAGGTCTTTACGCTGCCGCAGTACGG
TTACGCGACGCTGAACCGCGACAACACAGAGAATCCCACCGAGAGGAGCA
GCTTCTTCTGCCTAGAGTACTTTCCCAGCAAGATGCTGAGAACGGGCAAC
AACTTTGAGTTTACCTACAACTTTGAGGAGGTGCCCTTCCACTCCAGCTT
CGCTCCCAGTCAGAACCTGTTCAAGCTGGCCAACCCGCTGGTGGACCAGT
ACTTGTACCGCTTCGTGAGCACAAATAACACTGGCGGAGTCCAGTTCAAC
AAGAACCTGGCCGGGAGATACGCCAACACCTACAAAAACTGGTTCCCGGG
GCCCATGGGCCGAACCCAGGGCTGGAACCTGGGCTCCGGGGTCAACCGCG
CCAGTGTCAGCGCCTTCGCCACGACCAATAGGATGGAGCTCGAGGGCGCG
AGTTACCAGGTGCCCCCGCAGCCGAACGGCATGACCAACAACCTCCAGGG
CAGCAACACCTATGCCCTGGAGAACACTATGATCTTCAACAGCCAGCCGG
CGAACCCGGGCACCACCGCCACGTACCTCGAGGGCAACATGCTCATCACC
AGCGAGAGCGAGACGCAGCCGGTGAACCGCGTGGCGTACAACGTCGGCGG
GCAGATGGCCACCAACAACCAGAGCTCCACCACTGCCCCCGCGACCGGCA
CGTACAACCTCCAGGAAATCGTGCCCGGCAGCGTGTGGATGGAGAGGGAC
GTGTACCTCCAAGGACCCATCTGGGCCAAGATCCCAGAGACGGGGGCGCA
CTTTCACCCCTCTCCGGCCATGGGCGGATTCGGACTCAAACACCCACCGC
CCATGATGCTCATCAAGAACACGCCTGTGCCCGGAAATATCACCAGCTTC
TCGGACGTGCCCGTCAGCAGCTTCATCACCCAGTACAGCACCGGGCAGGT
CACCGTGGAGATGGAGTGGGAGCTCAAGAAGGAAAACTCCAAGAGGTGGA
ACCCCGAGATCCAGTACACAAACAACTACAACGACCCCCAGTTTGTGGAC
TTTGCCCCGGACGGCACCGGGGAATACAGAAGCACCAGACCTATCGGAAC
CCGATACCTTACCCGACCTCTTTAA

SEQ ID NO: 8-MV50
MSFVDHPPDWLEEVGEGLREFLGLEAGPPKPKPNQQHDQARGLVLPGYN
YLGPGNGLDRGEPVNRADEVAREHDISYNEQLEAGDNPYLKYNHADAEFQ
EKLADDTSFGGNLGKAVFQAKKRVLEPFGLVEEGAKTAPTGKRIDDHFPK
RKKARTEEDSKPSTSSDAEAGPSGSQQLQIPAQPASSLGADTMSAGGGGP
LGDNNQGADGVGNASGDWHCDSTWMGDRVVTKSTRTWVLPSYNNHQYREI
KSGSVDRSNANAYFGYSTPWGYFDFNRFHSHWSPRDWQRLINNYWGFRPR
SLRVKIFNIQVKEVTVQDSTTTIANNLTSTVQVFTDDDYQLPYVVGNGTE
GCLPAFPPQVFTLPQYGYATLNRDNTENPTERSSFFCLEYFPPSKMLRTGN

NFEFTYNFEEVPFHSSFAPSQNLFKLANPLVDQYLRFVSTNNTGGVQFN
KNLAGRYANTYKNWFPGPMGRTQGWNLGSGVNRASVSAFATTNRMELEGA
SYQVPPQPNGMTNNLQGSNTYALENTMIFNSQPANPGTTATYLEGNMLIT
SESETQPVNRVAYNVGGQMATNNQSSTTAPATGTYNLQEIVPGSVWMERD
VYLQGPIWAKIPETGAHFHPSPAMGGFGLKHPPPMMLIKNTPVPGNITSF
SDVPVSSFITQYSTGQVTVEMEWELKKENSKRWNPEIQYTNNYNDPQFVD
FAPDGTGEYRSTRPIGTRYLTRPL

SEQ ID NO: 9-MV53
ATGTCTTTTGTTGATCACCCTCCAGATTGGTTGGAAGAAGTTGGTGAAGG
TCTTCGCGAGTTTTTGGGCCTTGAAGCGGGCCCACCGAAACCAAAACCCA
ATCAGCAGCATCAAGATCAAGCCCGTGGTCTTGTGCTGCCTGGTTATAAC
TATCTCGGACCCGGAAACGGTCTCGATCGAGGAGAGCCTGTCAACAGGGC
AGACGAGGTCGCGCGAGAGCACGACATCTCGTACAACGAGCAGCTTGAGG
CGGGAGACAACCCCTACCTCAAGTACAACCACGCGGACGCCGAGTTTCAG
GAGAAGCTCGCCGACGACACATCCTTCGGGGGAAACCTCGGAAAGGCAGT
CTTTCAGGCCAAGAAAAGGGTTCTCGAACCTTTTGGCCTGGTTGAAGAGG
GTGCTAAGACGGCCCCTACCGGAAAGCGGATAGACGACCACTTTCCAAAA
AGAAAGAAGGCTCGGACCGAAGAGGACTCCAAGCCTTCCACCTCGTCAGA
CGCCGAAGCTGGACCCAGCGGATCCCAGCAGCTGCAATCCCAGCCCAAC
CAGCCTCAAGTTTGGGAGCTGATACAATGTCTGCGGGAGGTGGCGGCCCA
TTGGGCGACAATAACCAAGGTGCCGATGGAGTGGGCAATGCCTCGGGAGA
TTGGCATTGCGATTCCACGTGGATGGGGGACAGAGTCGTCACCAAGTCCA
CCCGAACCTGGGTGCTGCCCAGCTACAACAACCACCAGTACCGAGAGATC
AAAAGCGGCTCCGTCGACAGAAGCAACGCCAACGCCTACTTTGGATACAG
CACCCCCTGGGGGTACTTTGACTTTAACCGCTTCCACAGCCACTGGAGCC
CCCGAGACTGGCAAAGACTCATCAACAACTACTGGGGCTTCAGACCCCGG
TCCCTCAGAGTCAAAATCTTCAACATTCAAGTCAAAGAGGTCACGGTGCA
GGACTCCACCACCACCATCGCCAACAACCTCACCTCCACCGTCCAAGTGT
TTACGGACGACGACTACCAGCTGCCCTACGTCGTCGGCAACGGGACCGAG
GGATGCCTGCCGGCCTTCCCTCCGCAGGTCTTTACGCTGCCGCAGTACGG
TTACGCGACGCTGAACCGCGACAACACAGAAAATCCCACCGAGAGGAGCA
GCTTCTTCTGCCTAGAGTACTTTCCCAGCAAGATGCTGAGAACGGGCAAC
AACTTTGAGTTTACCTACAACTTTGAGGAGGTGCCCTTCCACTCCAGCTT
CGCTCCCAGTCAGAACCTGTTCAAGCTGGCCAACCCGCTGGTGGACCAGT
ACTTGTACCGCTTCGTGAGCACAAATAACACTGGCGGAGTCCAGTTCAAC
AAGAACCTGGCCGGGAGATACGCCAACACCTACAAAAACTGGTTCCCGGG
GCCCATGGGCCGAACCCAGGGCTGGAACCTGGGCTCCGGGGTCAACCGCG
CCAGTGTCAGCGCCTTCGCCACGACCAATAGGATGGAGCTCGAGGGCGCG
AGTTACCAGGTGCCCCCGCAGCCGAACGGCATGACCAACAACCTCCAGGG
CAGCAACACCTATGCCCTGGAGAACACTATGATCTTCAACAGCCAGCCGG
CGAACCCGGGCACCACCGCCACGTACCTCGAGGGCAACATGCTCATCACC

-continued

AGCGAGAGCGAGACGCAGCCGGTGAACCGCGTGGCGTACAACGTCGGCGG
GCAGATGGCCACCAACAACCAGAGCTCCACCACTGCCCCCGCGACCGGCA
CGTACAACCTCCAGGAAATCGTGCCCGGCAGCGTGTGGATGGAGAGGGAC
GTGTACCTCCAAGGACCCATCTGGGCCAAGATCCCAGAGACGGGGGCGCA
CTTTCACCCCTCTCCGGCCATGGGCGGATTCGGACTCAAACACCCACCGC
CCATGATGCTCATCAAGAACACGCCTGTGCCCGGAAATATCACCAGCTTC
TCGGACGTGCCCGTCAGCAGCTTCATCACCCAGTACAGCACCGGGCAGGT
CACCGTGGAGATGGAGTGGGAGCTCAAGAAGGAAAACTCCAAGAGGTGGA
ACCCAGAGATCCAGTACACAAACAACTACAACGACCCCCAGTTTGTGGAC
TTTGCCCCGGACAGCACCGGGGAATACAGAACCACCAGACCTATCGGAAC
CCGATACCTTACCCGACCCCTTTAA

SEQ ID NO: 10-MV53
MSFVDHPPDWLEEVGEGLREFLGLEAGPPKPKPNQQHQDQARGLVLPGYN
YLGPGNGLDRGEPVNRADEVAREHDISYNEQLEAGDNPYLKYNHADAEFQ
EKLADDTSFGGNLGKAVFQAKKRVLEPFGLVEEGAKTAPTGKRIDDHFPK
RKKARTEEDSKPSTSSDAEAGPSGSQQL*R*IPAQPASSLGADTMSAGGGGP
LGDNNQGADGVGNASGDWHCDSTWMGDRVVTKSTRTWVLPSYNNHQYREI
KSGSVD*R*SNANAYFGYSTPWGYFDFNRFHSHWSPRDWQRLINNYWGFRPR
SLRVKIFNIQVKEVTVQDSTTTIANNLTSTVQVFTDDDYQLPYVVGNTE
GCLPAFPPQVFTLPQYGYATLNRDNTENPTERSSFFCLEYFPSKMLRTGN
NFEFTYNFEEVPFHSSFAPSQNLFKLANPLVDQYLYRFVSTNNTGGVQFN
KNLAGRYANTYKNWFPGPMGRTQGWNLGSGVNRASVSAFATTNRMELEGA
SYQVPPQPNGMTNNLQGSNTYALENTMIFNSQPANPGTTATYLEGNMLIT
SESETQPVNRVAYNVGGQMATNNQSSTTAPATGTYNLQEIVPGSVWMERD
VYLQGPIWAKIPETGAHFHPSPAMGGFGLKHPPPMMLIKNTPVPGNITSF
SDVPVSSFITQYSTGQVTVEMEWELKKENSKRWNPEIQYTNNYNDPQFVD
FAPDSTGEYRTTRPIGTRYLTRPL

SEQ ID NO: 11-Wild-type AAV5 capsid
ATGTCTTTTGTTGATCACCCTCCAGATTGGTTGGAAGAAGTTGGTGAAGG
TCTTCGCGAGTTTTTGGGCCTTGAAGCGGGCCCACCGAAACCAAAACCCA
ATCAGCAGCATCAAGATCAAGCCCGTGGTCTTGTGCTGCCTGGTTATAAC
TATCTCGGACCCGGAAACGGTCTCGATCGAGGAGAGCCTGTCAACAGGGC
AGACGAGGTCGCGCGAGAGCACGACATCTCGTACAACGAGCAGCTTGAGG
CGGGAGACAACCCCTACCTCAAGTACAACCACGCGGACGCCGAGTTTCAG
GAGAAGCTCGCCGACGACACATCCTTCGGGGGAAACCTCGGAAAGGCAGT
CTTTCAGGCCAAGAAAAGGGTTCTCGAACCTTTTGGCCTGGTTGAAGAGG
GTGCTAAGACGGCCCCTACCGGAAAGCGGATAGACGACCACTTTCCAAAA
AGAAAGAAGGCTCGGACCGAAGAGGACTCCAAGCCTTCCACCTCGTCAGA
CGCCGAAGCTGGACCCAGCGGATCCCAGCAGCTGCAAATCCCAGCCCAAC
CAGCCTCAAGTTTGGGAGCTGATCAATGTCTGCGGGAGGTGGCGGCCCA
TTGGGCGACAATAACCAAGGTGCCGATGGAGTGGGCAATGCCTCGGGAGA -continued TTGGCATTGCGATTCCACGTGGATGGGGACAGAGTCGTCACCAAGTCCA
CCCGAACCTGGGTGCTGCCCAGCTACAACAACCACCAGTACCGAGAGATC
AAAAGCGGCTCCGTCGACGGAAGCAACGCCAACGCCTACTTTGGATACAG
CACCCCCTGGGGGTACTTTGACTTTAACCGCTTCCACAGCCACTGGAGCC
CCCGAGACTGGCAAAGACTCATCAACAACTACTGGGGCTTCAGACCCCGG
TCCCTCAGAGTCAAAATCTTCAACATTCAAGTCAAAGAGGTCACGGTGCA
GGACTCCACCACCACCATCGCCAACAACCTCACCTCCACCGTCCAAGTGT
TTACGGACGACGACTACCAGCTGCCCTACGTCGTCGGCAACGGGACCGAG
GGATGCCTGCCGGCCTTCCCTCCGCAGGTCTTTACGCTGCCGCAGTACGG
TTACGCGACGCTGAACCGCGACAACACAGAAAATCCCACCGAGAGGAGCA
GCTTCTTCTGCCTAGAGTACTTTCCCAGCAAGATGCTGAGAACGGGCAAC
AACTTTGAGTTTACCTACAACTTTGAGGAGGTGCCCTTCCACTCCAGCTT
CGCTCCCAGTCAGAACCTGTTCAAGCTGGCCAACCCGCTGGTGGACCAGT
ACTTGTACCGCTTCGTGAGCACAAATAACACTGGCGGAGTCCAGTTCAAC
AAGAACCTGGCCGGGAGATACGCCAACACCTACAAAAACTGGTTCCCGGG
GCCCATGGGCCGAACCCAGGGCTGGAACCTGGGCTCCGGGGTCAACCGCG
CCAGTGTCAGCGCCTTCGCCACGACCAATAGGATGGAGCTCGAGGGCGCG
AGTTACCAGGTGCCCCCGCAGCCGAACGGCATGACCAACAACCTCCAGGG
CAGCAACACCTATGCCCTGGAGAACACTATGATCTTCAACAGCCAGCCGG
CGAACCCGGGCACCACCGCCACGTACCTCGAGGGCAACATGCTCATCACC
AGCGAGAGCGAGACGCAGCCGGTGAACCGCGTGGCGTACAACGTCGGCGG
GCAGATGGCCACCAACAACCAGAGCTCCACCACTGCCCCCGCGACCGGCA
CGTACAACCTCCAGGAAATCGTGCCCGGCAGCGTGTGGATGGAGAGGGAC
GTGTACCTCCAAGGACCCATCTGGGCCAAGATCCCAGAGACGGGGGCGCA
CTTTCACCCCTCTCCGGCCATGGGCGGATTCGGACTCAAACACCCACCGC
CCATGATGCTCATCAAGAACACGCCTGTGCCCGGAAATATCACCAGCTTC
TCGGACGTGCCCGTCAGCAGCTTCATCACCCAGTACAGCACCGGGCAGGT
CACCGTGGAGATGGAGTGGGAGCTCAAGAAGGAAAACTCCAAGAGGTGGA
ACCCAGAGATCCAGTACACAAACAACTACAACGACCCCCAGTTTGTGGAC
TTTGCCCCGGACAGCACCGGGGAATACAGAACCACCAGACCTATCGGAAC
CCGATACCTTACCCGACCCCTTTAA SEQ ID NO: 12-Wild-type AAV5 capsid
MSFVDHPPDWLEEVGEGLREFLGLEAGPPKPKPNQQHQDQARGLVLPGYN
YLGPGNGLDRGEPVNRADEVAREHDISYNEQLEAGDNPYLKYNHADAEFQ
EKLADDTSFGGNLGKAVFQAKKRVLEPFGLVEEGAKTAPTGKRIDDHFPK
RKKARTEEDSKPSTSSDAEAGPSGSQQLQIPAQPASSLGADTMSAGGGGP
LGDNNQGADGVGNASGDWHCDSTWMGDRVVTKSTRTWVLPSYNNHQYREI
KSGSVDGSNANAYFGYSTPWGYFDFNRFHSHWSPRDWQRLINNYWGFRPR
SLRVKIFNIQVKEVTVQDSTTTIANNLTSTVQVFTDDDYQLPYVVGNTE
GCLPAFPPQVFTLPQYGYATLNRDNTENPTERSSFFCLEYFPSKMLRTGN
NFEFTYNFEEVPFHSSFAPSQNLFKLANPLVDQYLYRFVSTNNTGGVQFN -continued

KNLAGRYANTYKNWFPGPMGRTQGWNLGSGVNRASVSAFATTNRMELEGA

SYQVPPQPNGMTNNLQGSNTYALENTMIFNSQPANPGTTATYLEGNMLIT

SESETQPVNRVAYNVGGQMATNNQSSTTAPATGTYNLQEIVPGSVWMERD

VYLQGPIWAKIPETGAHFHPSPAMGGFGLKHPPPMMLIKNTPVPGNITSF

SDVPVSSFITQYSTGQVTVEMEWELKKENSKRWNPEIQYTNNYNDPQFVD

FAPDSTGEYRTTRPIGTRYLTRPL

SEQ ID NO: 13-forward primer
AGGCTCGGACCGAAGAGGACT

SEQ ID NO: 14-reverse primer
ATCGAGCGGCCGCAAGAGGCAGTATTTTAC

We claim:

1. A modified adeno-associated virus 5 (AAV5) capsid protein comprising an amino acid sequence of SEQ ID NO:12 and one or more mutation, wherein the one or more mutation comprises a G257R mutation.

2. The modified AAV5 capsid protein of claim 1, wherein the one or more mutation further comprises a mutation selected from Q179R, F417L, S705G, or any combination thereof.

3. The modified AAV5 capsid protein of claim 1, wherein the modified capsid protein comprises an amino acid sequence at least 99% identical to any one of SEQ ID NOS: 2, 4, 6, 8, or 10.

4. A nucleic acid encoding the modified AAV5 capsid protein of claim 1.

5. The nucleic of claim 4, comprising a nucleotide sequence at least 90% identical to the nucleotide sequence of any one of SEQ ID NOS: 1, 3, 5, 7, or 9.

6. A vector comprising the nucleic acid of claim 4.

7. The vector of claim 6, which is a plasmid, phage, viral vector, bacterial artificial chromosome, or yeast artificial chromosome.

8. The vector of claim 7, wherein the viral vector is an AAV vector.

9. A cell in vitro comprising the nucleic acid of claim 4.

10. A virus particle comprising the nucleic acid of claim 4.

11. The virus particle of claim 10, wherein the virus particle is an AAV particle, an adenovirus particle, a herpesvirus particle, or a baculovirus particle.

12. A method of producing a recombinant AAV particle comprising an AAV capsid, the method comprising:
providing a cell in vitro with a nucleic acid according to claim 9, an AAV rep coding sequence, an AAV vector genome comprising a heterologous nucleic acid, and helper functions for generating a productive AAV infection; and
allowing assembly of the recombinant AAV particle comprising the AAV capsid and encapsidating the AAV vector genome.

13. An AAV particle comprising:
an AAV vector genome; and
the modified AAV5 capsid protein of claim 1, wherein the AAV capsid encapsidates the AAV vector genome.

14. The AAV particle of claim 13, wherein the AAV vector genome comprises a heterologous nucleic acid.

15. The AAV particle of claim 13, wherein the heterologous nucleic acid is operably linked to a liver-specific promoter.

16. A pharmaceutical formulation comprising the AAV particle of claim 13 in a pharmaceutically acceptable carrier.

17. A method of delivering a nucleic acid of interest to a hepatocyte, the method comprising contacting the hepatocyte with the AAV particle of claim 13.

18. A method of delivering a nucleic acid of interest to a hepatocyte in a mammalian subject, the method comprising:
administering an effective amount of the AAV particle of claim 13 to a mammalian subject, thereby delivering the nucleic acid of interest to a hepatocyte in the mammalian subject.

19. A method of treating a disorder in a mammalian subject in need thereof, wherein the disorder is treatable by expressing a therapeutic product in the liver of the subject, the method comprising administering a therapeutically effective amount of the AAV particle of claim 13 to a mammalian subject, wherein the therapeutic product is expressed, thereby treating the disorder.

* * * * *

UNITED STATES PATENT AND TRADEMARK OFFICE
CERTIFICATE OF CORRECTION

Page 1 of 1

PATENT NO. : 12,209,251 B2
APPLICATION NO. : 17/307117
DATED : January 28, 2025
INVENTOR(S) : Xiao et al.

It is certified that error appears in the above-identified patent and that said Letters Patent is hereby corrected as shown below:

In the Claims

Column 87, Line 34, Claim 12: Please correct "claim 9" to read --claim 4--

Signed and Sealed this
Fifteenth Day of July, 2025

Coke Morgan Stewart
*Acting Director of the United States Patent and Trademark Office*

SEQUENCE LISTING

<160> NUMBER OF SEQ ID NOS: 14

<210> SEQ ID NO 1
<211> LENGTH: 2175
<212> TYPE: DNA
<213> ORGANISM: Artificial
<220> FEATURE:
<223> OTHER INFORMATION: MV1

<400> SEQUENCE: 1

| | | | | |
|---|---|---|---|---|
| atgtcttttg | ttgatcaccc | tccagattgg | ttggaagaag | ttggtgaagg | tcttcgcgag | 60 |
| tttttgggcc | ttgaagcggg | cccaccgaaa | ccaaaaccca | atcagcagca | tcaagatcaa | 120 |
| gcccgtggtc | ttgtgctgcc | tggttataac | tatctcggac | ccggaaacgg | tctcgatcga | 180 |
| ggagagcctg | tcaacagggc | agacgaggtc | gcgcgagagc | acgacatctc | gtacaacgag | 240 |
| cagcttgagg | cgggagacaa | cccctacctc | aagtacaaca | acgcggacgc | cgagtttcag | 300 |
| gagaagctcg | ccgacgacac | atccttcggg | ggaaacctcg | gaaaggcagt | ctttcaggcc | 360 |
| aagaaaaggg | ttctcgaacc | ttttggcctg | gttgaagagg | gtgctaagac | ggcccctacc | 420 |
| ggaaagcgga | tagacgacca | cttttccaaaa | agaaagaagg | ctcggaccga | agaggactcc | 480 |
| aagccttcca | cctcgtcaga | cgccgaagct | ggacccagcg | gatcccagca | gctgcaaatc | 540 |
| ccagcccaac | cagcctcaag | tttgggagct | gatacaatgt | ctgcgggagg | tggcggccca | 600 |
| ttgggcgaca | ataaccaagg | tgccgatgga | gtgggcaatg | cctcgggaga | ttggcattgc | 660 |
| gattccacgt | ggatggggga | cagagtcgtc | accaagtcca | cccgaacctg | ggtgctgccc | 720 |
| agctacaaca | accaccagta | ccgagagatc | aaaagcggct | ccgtcgacag | aagcaacgcc | 780 |
| aacgcctact | ttggatacag | cacccctggg | gggtactttg | actttaaccg | cttccacagc | 840 |
| cactggagcc | cccgagactg | gcaaagactc | atcaacaact | actggggctt | cagacccgg | 900 |
| tccctcagag | tcaaaatctt | caacattcaa | gtcaaagagg | tcacggtgca | ggactccacc | 960 |
| accaccatcg | ccaacaacct | cacctccacc | gtccaagtgt | ttacggacga | cgactaccag | 1020 |
| ctgcccctacg | tcgtcggcaa | cgggaccgag | ggatgcctgc | cggccttccc | tccgcaggtc | 1080 |
| tttacgctgc | cgcagtacgg | ttacgcgacg | ctgaaccgcg | acaacacaga | aaatcccacc | 1140 |
| gagaggagca | gcttcttctg | cctagagtac | tttcccagca | agatgctgag | aacgggcaac | 1200 |
| aactttgagt | ttacctacaa | cttgaggag | gtgcccttcc | actccagcct | cgctcccagt | 1260 |
| cagaacctct | tcaagctggc | caacccgctg | gtggaccagt | acttgtaccg | cttcgtgagc | 1320 |
| acaaataaca | ctggcggagt | ccagttcaac | aagaacctgg | ccgggagata | cgccaacacc | 1380 |
| tacaaaaact | ggttcccggg | gcccatgggc | cgaacccagg | gctggaacct | gggctccggg | 1440 |
| gtcaaccgcg | ccagtgtcag | cgccttcgcc | acgaccaata | ggatggagct | cgagggcgcg | 1500 |
| agttaccagg | tgcccccgca | gccgaacggc | atgaccaaca | acctccaggg | cagcaacacc | 1560 |
| tatgccctgg | agaacactat | gatcttcaac | agccagccgg | cgaacccggg | caccaccgcc | 1620 |

```
acgtacctcg agggcaacat gctcatcacc agcgagagcg agacgcagcc ggtgaaccgc    1680
gtggcttaca acgtcggcgg gcagatggcc accaacaacc agagctccac cactgccccc    1740
gcgaccggca cgtacaacct ccaggaaatc gtgcccggca gcgtgtggat ggagagggac    1800
gtgtacctcc aaggacccat ctgggccaag atcccagaga cggggggcgca ctttcacccc    1860 tctccggcca tgggcggatt cggactcaaa cacccaccgc ccatgatgct catcaagaac    1920
acgcctgtgc ccgaaatat caccagcttc tcggacgtgc ccgtcagcag cttcatcacc    1980
cagtacagca ccgggcaggt caccgtggag atggagtggg agctcaagaa ggaaaactcc    2040
aagaggtgga accccgagat ccagtacaca aacaactaca acgaccccca gtttgtggac    2100
tttgccccgg acagcaccgg ggaatacaga agcaccagac ctatcggaac ccgatacctt    2160
acccgacccc tttaa                                                    2175

<210> SEQ ID NO 2
<211> LENGTH: 724
<212> TYPE: PRT
<213> ORGANISM: Artificial
<220> FEATURE:
<223> OTHER INFORMATION: MV1

<400> SEQUENCE: 2
```

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Arg Ser Asn Ala Asn Ala Tyr Phe Gly Tyr Ser Thr Pro Trp Gly Tyr

-continued

```
                260                 265                 270
Phe Asp Phe Asn Arg Phe His Ser His Trp Ser Pro Arg Asp Trp Gln
                275                 280                 285
Arg Leu Ile Asn Asn Tyr Trp Gly Phe Arg Pro Arg Ser Leu Arg Val
                290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
                340                 345                 350
Leu Pro Ala Phe Pro Pro Gln Val Phe Thr Leu Pro Gln Tyr Gly Tyr
                355                 360                 365
Ala Thr Leu Asn Arg Asp Asn Thr Glu Asn Pro Thr Glu Arg Ser Ser
                370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Leu Ala Pro Ser Gln Asn Leu Phe Lys Leu Ala Asn Pro Leu Val Asp
                420                 425                 430
Gln Tyr Leu Tyr Arg Phe Val Ser Thr Asn Asn Thr Gly Gly Val Gln
                435                 440                 445
Phe Asn Lys Asn Leu Ala Gly Arg Tyr Ala Asn Thr Tyr Lys Asn Trp
                450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
                500                 505                 510
Asn Asn Leu Gln Gly Ser Asn Thr Tyr Ala Leu Glu Asn Thr Met Ile
                515                 520                 525
Phe Asn Ser Gln Pro Ala Asn Pro Gly Thr Thr Ala Thr Tyr Leu Glu
                530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Ala Pro Ala Thr Gly Thr Tyr Asn Leu Gln Glu Ile Val Pro
                580                 585                 590
Gly Ser Val Trp Met Glu Arg Asp Val Tyr Leu Gln Gly Pro Ile Trp
                595                 600                 605
Ala Lys Ile Pro Glu Thr Gly Ala His Phe His Pro Ser Pro Ala Met
                610                 615                 620
Gly Gly Phe Gly Leu Lys His Pro Pro Met Met Leu Ile Lys Asn
625                 630                 635                 640
Thr Pro Val Pro Gly Asn Ile Thr Ser Phe Ser Asp Val Pro Val Ser
                645                 650                 655
Ser Phe Ile Thr Gln Tyr Ser Thr Gly Gln Val Thr Val Glu Met Glu
                660                 665                 670
Trp Glu Leu Lys Lys Glu Asn Ser Lys Arg Trp Asn Pro Glu Ile Gln
                675                 680                 685
```

Tyr Thr Asn Asn Tyr Asn Asp Pro Gln Phe Val Asp Phe Ala Pro Asp
          690                 695                 700

Ser Thr Gly Glu Tyr Arg Ser Thr Arg Pro Ile Gly Thr Arg Tyr Leu
705                 710                 715                 720

Thr Arg Pro Leu

<210> SEQ ID NO 3
<211> LENGTH: 2175
<212> TYPE: DNA
<213> ORGANISM: Artificial
<220> FEATURE:
<223> OTHER INFORMATION: MV18

<400> SEQUENCE: 3

| | | | | | |
|---|---|---|---|---|---|
| atgtcttttg | ttgatcaccc | tccagattgg | ttggaagaag | ttggtgaagg | tcttcgcgag | 60 |
| tttttgggcc | ttgaagcggg | cccaccgaaa | ccaaaaccca | atcagcagca | tcaagatcaa | 120 |
| gcccgtggtc | ttgtgctgcc | tggttataac | tatctcggac | ccggaaacgg | tctcgatcga | 180 |
| ggagagcctg | tcaacagggc | agacgaggtc | gcgcgagagc | acgacatctc | gtacaacgag | 240 |
| cagcttgagg | cgggagacaa | cccctacctc | aagtacaacc | acgcggacgc | cgagtttcag | 300 |
| gagaagctcg | ccgacgacac | atccttcggg | ggaaacctcg | gaaaggcagt | ctttcaggcc | 360 |
| aagaaaaggg | ttctcgaacc | ttttggcctg | gttgaagagg | gtgctaagac | ggcccctacc | 420 |
| ggaaagcgga | tagacgacca | cttttccaaaa | agaaagaagg | ctcggaccga | agaggactcc | 480 |
| aagccttcca | cctcgtcaga | cgccgaagct | ggacccagcg | atcccagca | gctgcaaatc | 540 |
| ccagcccaac | cagcctcaag | tttgggagct | gatacaatgt | ctgcgggagg | tggcggccca | 600 |
| ttgggcgaca | taaccaagg | tgccgatgga | gtgggcaatg | cctcgggaga | ttggcattgc | 660 |
| gattccacgt | ggatggggga | cagagtcgtc | accaagtcca | cccgaacctg | ggtgctgccc | 720 |
| agctacaaca | ccaccagta | ccgagagatc | aaaagcggct | ccgtcgacag | aagcaacgcc | 780 |
| aacgcctact | ttggatacag | caccccctgg | gggtactttg | actttaaccg | cttccacagc | 840 |
| cactggagcc | cccagactg | gcaaagactc | atcaacaact | actggggctt | cagaccccgg | 900 |
| tccctcagag | tcaaaatctt | caacattcaa | gtcaaagagg | tcacggtgca | ggactccacc | 960 |
| accaccatcg | ccaacaacct | cacctccacc | gtccaagtgt | ttacggacga | cgactaccag | 1020 |
| ctgcccacg | tcgtcggcaa | cgggaccgag | ggatgcctgc | cggccttccc | tccgcaggtc | 1080 |
| tttacgctgc | cgcagtacgg | ttacgcgacg | ctgaaccgcg | acaacacaga | aaatcccacc | 1140 |
| gagaggagca | gcttcttctg | cctagagtac | tttcccagca | agatgctgag | aacgggcaac | 1200 |
| aactttgagt | ttacctacaa | ctttgaggag | gtgcccttcc | actccagctt | cgctcccagt | 1260 |
| cagaacctgt | tcaagctggc | caacccgctg | gtggaccagt | acttgtaccg | cttcgtgagc | 1320 |
| acaaataaca | ctggcggagt | ccagttcaac | aagaacctgg | ccgggagata | cgccaacacc | 1380 |
| tacaaaaact | ggttcccggg | gcccatgggc | cgaacccagg | gctggaacct | gggctccggg | 1440 |
| gtcaaccgcg | ccagtgtcag | cgccttcgcc | acgaccaata | ggatggagct | cgagggcgcg | 1500 |
| agttaccagg | tgcccccgca | gccgaacggc | atgaccaaca | acctccaggg | cagcaacacc | 1560 |
| tatgccctgg | agaacactat | gatcttcaac | agccagccgg | cgaacccggg | caccaccgcc | 1620 |
| acgtacctcg | agggcaacat | gctcatcacc | agcgagagcg | agacgcagcc | ggtgaaccgc | 1680 |
| gtggcgtaca | acgtcggcgg | gcagatggcc | accaacaacc | agagctccac | cactgccccc | 1740 |
| gcgaccggca | cgtacaacct | ccaggaaatc | gtgcccggca | gcgtgtggat | ggagagggac | 1800 |

```
gtgtacctcc aaggacccat ctgggccaag atcccagaga cggggggcgca ctttcacccc    1860 tctccggcca tgggcggatt cggactcaaa cacccaccgc ccatgatgct catcaagaac    1920
acgcctgtgc ccgaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca cgaccccca gtttgtggac    2100 tttgccccgg acagcaccgg ggaatacaga accaccagac ctatcggaac ccgatacctt    2160
acccgacccc tttaa                                                    2175

<210> SEQ ID NO 4
<211> LENGTH: 724
<212> TYPE: PRT
<213> ORGANISM: Artificial
<220> FEATURE:
<223> OTHER INFORMATION: MV18

<400> SEQUENCE: 4

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Arg Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
```

```
                290             295             300
Lys Ile Phe Asn Ile Gln Val Lys Glu Val Thr Val Gln Asp Ser Thr
305                 310             315                 320

Thr Thr Ile Ala Asn Asn Leu Thr Ser Thr Val Gln Val Phe Thr Asp
                325             330             335

Asp Asp Tyr Gln Leu Pro Tyr Val Val Gly Asn Gly Thr Glu Gly Cys
            340             345             350

Leu Pro Ala Phe Pro Pro Gln Val Phe Thr Leu Pro Gln Tyr Gly Tyr
            355             360             365

Ala Thr Leu Asn Arg Asp Asn Thr Glu Asn Pro Thr Glu Arg Ser Ser
        370             375             380

Phe Phe Cys Leu Glu Tyr Phe Pro Ser Lys Met Leu Arg Thr Gly Asn
385             390             395             400

Asn Phe Glu Phe Thr Tyr Asn Phe Glu Glu Val Pro Phe His Ser Ser
                405             410             415

Phe Ala Pro Ser Gln Asn Leu Phe Lys Leu Ala Asn Pro Leu Val Asp
            420             425             430

Gln Tyr Leu Tyr Arg Phe Val Ser Thr Asn Asn Thr Gly Gly Val Gln
            435             440             445

Phe Asn Lys Asn Leu Ala Gly Arg Tyr Ala Asn Thr Tyr Lys Asn Trp
        450             455             460

Phe Pro Gly Pro Met Gly Arg Thr Gln Gly Trp Asn Leu Gly Ser Gly
465             470             475             480

Val Asn Arg Ala Ser Val Ser Ala Phe Ala Thr Thr Asn Arg Met Glu
                485             490             495

Leu Glu Gly Ala Ser Tyr Gln Val Pro Pro Gln Pro Asn Gly Met Thr
            500             505             510

Asn Asn Leu Gln Gly Ser Asn Thr Tyr Ala Leu Glu Asn Thr Met Ile
            515             520             525

Phe Asn Ser Gln Pro Ala Asn Pro Gly Thr Thr Ala Thr Tyr Leu Glu
            530             535             540

Gly Asn Met Leu Ile Thr Ser Glu Ser Glu Thr Gln Pro Val Asn Arg
545             550             555             560

Val Ala Tyr Asn Val Gly Gly Gln Met Ala Thr Asn Asn Gln Ser Ser
                565             570             575

Thr Thr Ala Pro Ala Thr Gly Thr Tyr Asn Leu Gln Glu Ile Val Pro
            580             585             590

Gly Ser Val Trp Met Glu Arg Asp Val Tyr Leu Gln Gly Pro Ile Trp
            595             600             605

Ala Lys Ile Pro Glu Thr Gly Ala His Phe His Pro Ser Pro Ala Met
        610             615             620

Gly Gly Phe Gly Leu Lys His Pro Pro Pro Met Met Leu Ile Lys Asn
625             630             635             640

Thr Pro Val Pro Gly Asn Ile Thr Ser Phe Ser Asp Val Pro Val Ser
                645             650             655

Ser Phe Ile Thr Gln Tyr Ser Thr Gly Gln Val Thr Val Glu Met Glu
            660             665             670

Trp Glu Leu Lys Lys Glu Asn Ser Lys Arg Trp Asn Pro Glu Ile Gln
            675             680             685

Tyr Thr Asn Asn Tyr Asn Asp Pro Gln Phe Val Asp Phe Ala Pro Asp
        690             695             700

Ser Thr Gly Glu Tyr Arg Thr Thr Arg Pro Ile Gly Thr Arg Tyr Leu
705             710             715             720
```

Thr Arg Pro Leu

<210> SEQ ID NO 5
<211> LENGTH: 2175
<212> TYPE: DNA
<213> ORGANISM: Artificial
<220> FEATURE:
<223> OTHER INFORMATION: MV20

<400> SEQUENCE: 5

| | | | | | |
|---|---|---|---|---|---|
| atgtcttttg | ttgatcaccc | tccagattgg | ttggaagaag | ttggtgaagg | tcttcgcgag | 60 |
| tttttgggcc | ttgaagcggg | cccaccgaaa | ccaaaaccca | atcagcagca | tcaagatcaa | 120 |
| gcccgtggtc | ttgtgctgcc | tggttataac | tatctcggac | ccggaaacgg | tctcgatcga | 180 |
| ggagagcctg | tcaacagggc | agacgaggtc | gcgcgagagc | acgacatctc | gtacaacgag | 240 |
| cagcttgagg | cgggagacaa | ccccctacctc | aagtacaacc | acgcggacgc | cgagtttcag | 300 |
| gagaagctcg | ccgacgacac | atccttcggg | ggaaacctcg | gaaaggcagt | ctttcaggcc | 360 |
| aagaaaaggg | ttctcgaacc | ttttggcctg | gttgaagagg | gtgctaagac | ggcccctacc | 420 |
| ggaaagcgga | tagacgacca | cttttccaaaa | agaaagaagg | ctcggaccga | agaggactcc | 480 |
| aagccttcca | cctcgtcaga | cgccgaagct | ggacccagcg | atcccagca | gctgcaaatc | 540 |
| ccagcccaac | cagcctcaag | tttgggagct | gatacaatgt | ctgcgggagg | tgcggctca | 600 |
| ttgggcgaca | ataaccaagg | tgccgatgga | gtgggcaatg | cctcgggaga | ttggcattgc | 660 |
| gattccacgt | ggatggggga | cagagtcgtc | accaagtcca | cccgaacctg | ggtgctgccc | 720 |
| agctacaaca | accaccagta | ccgagagatc | aaaagcggct | ccgtcgacgg | aagcaacgcc | 780 |
| aacgcctact | ttggatacag | cacccccctgg | gggtactttg | actttaaccg | cttccacagc | 840 |
| cactggagcc | cccgagactg | gcaaagactc | atcaacaact | actggggctt | cagacccgg | 900 |
| tccctcagag | tcaaaatctt | caacattcaa | gtcaaagagg | tcacggtgca | ggactccacc | 960 |
| accaccatcg | ccaacaacct | cacctccacc | gtccaagtgt | ttacgacga | cgactaccag | 1020 |
| ctgccctacg | tcgtcggcaa | cgggaccgag | ggatgcctgc | cggccttccc | tccgcaggtc | 1080 |
| tttacgctgc | cgcagtacgg | ttacgcgacg | ctgaaccgcg | acaacacaga | aaatcccacc | 1140 |
| gagaggagca | gcttcttctg | cctagagtac | tttcccagca | agatgctgag | aacgggcaac | 1200 |
| aactttgagt | ttacctacaa | cttttgaggag | gtgcccttcc | actccagctt | cgctcccagt | 1260 |
| cagaacctct | tcaagctggc | caacccgctg | gtggaccagt | acttgtaccg | cttcgtgagc | 1320 |
| acaaataaca | ctggcggagt | ccagttcaac | aagaacctgg | ccgggagata | tgccaacacc | 1380 |
| tacaaaaact | ggttcccggg | gcccataggc | cgaacccagg | gctggaacct | gggctccggg | 1440 |
| gtcaaccgcg | ccagtgtcag | cgccttcgcc | acgaccaata | ggatggagct | cgagggcgcg | 1500 |
| agttaccagg | tgcccccgca | gccgaacggc | atgaccaaca | acctccaggg | cagcaacacc | 1560 |
| tatgccctgg | agaacactat | gatcttcaac | agccagccgg | cgaacccggg | caccaccgcc | 1620 |
| acgtacctcg | agggcaacat | gctcatcacc | agcgagagcg | agacgcagcc | ggtgaaccgc | 1680 |
| gtggcgtaca | acgtcggcgg | gcagatggcc | accaacaacc | agagctccac | cactaccccc | 1740 |
| gcgaccggca | cgtacaacct | ccaggaaatc | gtgcccggca | gcgtgtggat | ggagagggac | 1800 |
| gtgtacctcc | aaggacccat | ctgggccaag | atcccagaga | cggggggcgca | cttcacccc | 1860 |
| tctccggcca | tggcggatt | cggactcaaa | cacccaccgc | ccatgatgct | catcaagaac | 1920 |
| acgcctgtgc | ccggaaatat | caccagcttc | tcggacgtgc | ccgtcagcag | cttcatcacc | 1980 |

-continued

```
cagtacagca ccgggcaggt cactgtggag atggagtggg agctcaagaa ggaaaactcc    2040
aagaggtgga acccagagat ccagtacaca aacaactaca acgacccca gtttgtggac     2100 tttgccccgg acagcaccgg ggaatacaga agcaccagac ctatcggaac ccgataccttt  2160 acccgaccc tttaa                                                      2175
```

```
<210> SEQ ID NO 6
<211> LENGTH: 724
<212> TYPE: PRT
<213> ORGANISM: Artificial
<220> FEATURE:
<223> OTHER INFORMATION: MV20

<400> SEQUENCE: 6
```

| Met | Ser | Phe | Val | Asp | His | Pro | Pro | Asp | Trp | Leu | Glu | Glu | Val | Gly | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Leu | Arg | Glu | Phe | Leu | Gly | Leu | Glu | Ala | Gly | Pro | Pro | Lys | Pro | Lys |
|     |     |     | 20  |     |     |     |     | 25  |     |     |     |     | 30  |     |     |

| Pro | Asn | Gln | Gln | His | Gln | Asp | Gln | Ala | Arg | Gly | Leu | Val | Leu | Pro | Gly |
|     |     |     | 35  |     |     |     |     | 40  |     |     |     |     | 45  |     |     |

| Tyr | Asn | Tyr | Leu | Gly | Pro | Gly | Asn | Gly | Leu | Asp | Arg | Gly | Glu | Pro | Val |
| 50  |     |     |     |     | 55  |     |     |     |     | 60  |     |     |     |     |     |

| Asn | Arg | Ala | Asp | Glu | Val | Ala | Arg | Glu | His | Asp | Ile | Ser | Tyr | Asn | Glu |
| 65  |     |     |     |     | 70  |     |     |     |     | 75  |     |     |     |     | 80  |

| Gln | Leu | Glu | Ala | Gly | Asp | Asn | Pro | Tyr | Leu | Lys | Tyr | Asn | His | Ala | Asp |
|     |     |     |     | 85  |     |     |     |     | 90  |     |     |     |     | 95  |     |

| Ala | Glu | Phe | Gln | Glu | Lys | Leu | Ala | Asp | Asp | Thr | Ser | Phe | Gly | Gly | Asn |
|     |     |     | 100 |     |     |     |     | 105 |     |     |     |     | 110 |     |     |

| Leu | Gly | Lys | Ala | Val | Phe | Gln | Ala | Lys | Lys | Arg | Val | Leu | Glu | Pro | Phe |
|     |     |     | 115 |     |     |     |     | 120 |     |     |     |     | 125 |     |     |

| Gly | Leu | Val | Glu | Glu | Gly | Ala | Lys | Thr | Ala | Pro | Thr | Gly | Lys | Arg | Ile |
| 130 |     |     |     |     | 135 |     |     |     |     | 140 |     |     |     |     |     |

| Asp | Asp | His | Phe | Pro | Lys | Arg | Lys | Lys | Ala | Arg | Thr | Glu | Glu | Asp | Ser |
| 145 |     |     |     |     | 150 |     |     |     |     | 155 |     |     |     |     | 160 |

| Lys | Pro | Ser | Thr | Ser | Ser | Asp | Ala | Glu | Ala | Gly | Pro | Ser | Gly | Ser | Gln |
|     |     |     |     | 165 |     |     |     |     | 170 |     |     |     |     | 175 |     |

| Gln | Leu | Gln | Ile | Pro | Ala | Gln | Pro | Ala | Ser | Ser | Leu | Gly | Ala | Asp | Thr |
|     |     |     |     | 180 |     |     |     |     | 185 |     |     |     |     | 190 |     |

| Met | Ser | Ala | Gly | Gly | Gly | Ser | Leu | Gly | Asp | Asn | Asn | Gln | Gly | Ala |
|     |     |     | 195 |     |     |     |     | 200 |     |     |     |     | 205 |     |

| Asp | Gly | Val | Gly | Asn | Ala | Ser | Gly | Asp | Trp | His | Cys | Asp | Ser | Thr | Trp |
| 210 |     |     |     |     | 215 |     |     |     |     | 220 |     |     |     |     |     |

| Met | Gly | Asp | Arg | Val | Val | Thr | Lys | Ser | Thr | Arg | Thr | Trp | Val | Leu | Pro |
| 225 |     |     |     |     | 230 |     |     |     |     | 235 |     |     |     |     | 240 |

| Ser | Tyr | Asn | Asn | His | Gln | Tyr | Arg | Glu | Ile | Lys | Ser | Gly | Ser | Val | Asp |
|     |     |     |     | 245 |     |     |     |     | 250 |     |     |     |     | 255 |     |

| Gly | Ser | Asn | Ala | Asn | Ala | Tyr | Phe | Gly | Tyr | Ser | Thr | Pro | Trp | Gly | Tyr |
|     |     |     | 260 |     |     |     |     | 265 |     |     |     |     | 270 |     |     |

| Phe | Asp | Phe | Asn | Arg | Phe | His | Ser | His | Trp | Ser | Pro | Arg | Asp | Trp | Gln |
|     |     |     | 275 |     |     |     |     | 280 |     |     |     |     | 285 |     |     |

| Arg | Leu | Ile | Asn | Asn | Tyr | Trp | Gly | Phe | Arg | Pro | Arg | Ser | Leu | Arg | Val |
|     |     |     | 290 |     |     |     |     | 295 |     |     |     |     | 300 |     |     |

| Lys | Ile | Phe | Asn | Ile | Gln | Val | Lys | Glu | Val | Thr | Val | Gln | Asp | Ser | Thr |
| 305 |     |     |     |     | 310 |     |     |     |     | 315 |     |     |     |     | 320 |

| Thr | Thr | Ile | Ala | Asn | Asn | Leu | Thr | Ser | Thr | Val | Gln | Val | Phe | Thr | Asp |

```
                    325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gln Tyr Gly Tyr
            355                 360                 365
Ala Thr Leu Asn Arg Asp Asn Thr Glu Asn Pro Thr Glu Arg Ser Ser
            370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
            435                 440                 445
Phe Asn Lys Asn Leu Ala Gly Arg Tyr Ala Asn Thr Tyr Lys Asn Trp
        450                 455                 460
Phe Pro Gly Pro Ile Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
            500                 505                 510
Asn Asn Leu Gln Gly Ser Asn Thr Tyr Ala Leu Glu Asn Thr Met Ile
            515                 520                 525
Phe Asn Ser Gln Pro Ala Asn Pro Gly Thr Thr Ala Thr Tyr Leu Glu
            530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Thr Pro Ala Thr Gly Thr Tyr Asn Leu Gln Glu Ile Val Pro
            580                 585                 590
Gly Ser Val Trp Met Glu Arg Asp Val Tyr Leu Gln Gly Pro Ile Trp
            595                 600                 605
Ala Lys Ile Pro Glu Thr Gly Ala His Phe His Pro Ser Pro Ala Met
        610                 615                 620
Gly Gly Phe Gly Leu Lys His Pro Pro Pro Met Met Leu Ile Lys Asn
625                 630                 635                 640
Thr Pro Val Pro Gly Asn Ile Thr Ser Phe Ser Asp Val Pro Val Ser
                645                 650                 655
Ser Phe Ile Thr Gln Tyr Ser Thr Gly Gln Val Thr Val Glu Met Glu
            660                 665                 670
Trp Glu Leu Lys Lys Glu Asn Ser Lys Arg Trp Asn Pro Glu Ile Gln
            675                 680                 685
Tyr Thr Asn Asn Tyr Asn Asp Pro Gln Phe Val Asp Phe Ala Pro Asp
        690                 695                 700
Ser Thr Gly Glu Tyr Arg Ser Thr Arg Pro Ile Gly Thr Arg Tyr Leu
705                 710                 715                 720
Thr Arg Pro Leu

<210> SEQ ID NO 7
<211> LENGTH: 2175
```

```
<212> TYPE: DNA
<213> ORGANISM: Artificial
<220> FEATURE:
<223> OTHER INFORMATION: MV50

<400> SEQUENCE: 7
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg gaaaggcagt cttcaggcc     360
aagaaaaggg ttctcgaacc ttttggcctg gttgaagagg gtgctaagac ggcccctacc     420
ggaaagcgga tagacgacca ctttccaaaa agaaagaagg ctcggaccga agaggactcc     480
aagccttcca cctcgtcaga cgccgaagct ggacccagcg gatcccagca gctgcaaatc     540
ccagcccaac cagcctcaag tttgggagct gatacaatgt ctgcgggagg tggcggccca     600
ttgggcgaca taaccaagg tgccgatgga gtgggcaatg cctcgggaga ttggcattgc     660
gattccacgt ggatggggga cagagtcgtc accaagtcca cccgaacctg ggtgctgccc     720
agctacaaca accaccagta ccgagagatc aaaagcggct ccgtcgacag aagcaacgcc     780
aacgcctact ttggatacag caccccctgg gggtactttg actttaaccg cttccacagc     840
cactggagcc cccgagactg gcaaagactc atcaacaact actggggctt cagaccccgg     900
tccctcagag tcaaaatctt caacattcaa gtcaagagg tcacggtgca ggactccacc     960
accaccatcg ccaacaacct cacctccacc gtccaagtgt ttacggacga cgactaccag    1020
ctgccctacg tcgtcggcaa cgggaccgag ggatgcctgc cggccttccc tccgcaggtc    1080
tttacgctgc cgcagtacgg ttacgcgacg ctgaaccgcg acaacacaga gaatcccacc    1140
gagaggagca gcttcttctg cctagagtac tttcccagca agatgctgag aacgggcaac    1200
aactttgagt ttacctacaa cttttgaggag gtgcccttcc actccagctt cgctcccagt    1260
cagaacctgt tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttccccgg gcccatgggc cgaacccagg gctggaacct gggctccggg    1440
gtcaaccgcg ccagtgtcag cgccttcgcc acgaccaata ggatggagct cgagggcgcg    1500
agttaccagg tgccccgca gccgaacggc atgaccaaca acctccaggg cagcaacacc    1560
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca gcgtgtggat ggagagggac    1800
gtgtacctcc aaggacccat ctgggccaag atcccagaga cggggcgca ctttcacccc    1860
tctccggcca tgggcggatt cggactcaaa caccccaccgc ccatgatgct catcaagaac    1920
acgcctgtgc ccggaaatat caccagcttc tcggacgtgc ccgtcagcag cttcatcacc    1980
cagtacagca ccgggcaggt caccgtggag atggagtggg agctcaagaa ggaaaactcc    2040
aagaggtgga accccgagat ccagtacaca aacaactaca acgacccca gtttgtggac    2100
tttgccccgg acggcaccgg ggaatacaga agcaccgac ctatcggaac ccgataccttt    2160
```
acccgacctc tttaa                                                                 2175

<210> SEQ ID NO 8
<211> LENGTH: 724
<212> TYPE: PRT
<213> ORGANISM: Artificial
<220> FEATURE:
<223> OTHER INFORMATION: MV50

<400> SEQUENCE: 8

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Arg Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr 355                 360                 365
Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
690                 695                 700

Gly Thr Gly Glu Tyr Arg Ser Thr Arg Pro Ile Gly Thr Arg Tyr Leu
705                 710                 715                 720

Thr Arg Pro Leu

<210> SEQ ID NO 9
<211> LENGTH: 2175
<212> TYPE: DNA
<213> ORGANISM: Artificial
<220> FEATURE:
<223> OTHER INFORMATION: MV53

<400> SEQUENCE: 9

```
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc ttttggcctg gttgaagagg gtgctaagac ggcccctacc     420
ggaaagcgga tagacgacca cttttccaaaa agaaagaagg ctcggaccga agaggactcc     480
aagccttcca cctcgtcaga cgccgaagct ggacccagcg atcccagca gctgcgaatc      540
ccagcccaac cagcctcaag tttgggagct gatacaatgt ctgcgggagg tggcggccca     600
tgggcgaca ataaccaagg tgccgatgga gtgggcaatg cctcgggaga ttggcattgc       660
gattccacgt ggatggggga cagagtcgtc accaagtcca cccgaacctg ggtgctgccc     720
agctacaaca accaccagta ccgagagatc aaaagcggct ccgtcgacag aagcaacgcc     780
aacgcctact ttggatacag cacccccctgg gggtactttg actttaaccg cttccacagc    840
cactggagcc cccgagactg gcaaagactc atcaacaact actggggctt cagaccccgg     900
tccctcagag tcaaaatctt caacattcaa gtcaaagagg tcacggtgca ggactccacc     960
accaccatcg ccaacaacct cacctccacc gtccaagtgt ttacggacga cgactaccag    1020
ctgccctacg tcgtcggcaa cgggaccgag ggatgcctgc cggccttccc tccgcaggtc    1080
tttacgctgc cgcagtacgg ttacgcgacg ctgaaccgcg acaacacaga aaatcccacc    1140
gagaggagca gcttcttctg cctagagtac tttcccagca agatgctgag aacgggcaac    1200
aactttgagt ttacctacaa cttgaggag gtgcccttcc actccagctt cgctcccagt     1260
cagaacctgt tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttcccggg gcccatgggc cgaacccagg gctggaacct gggctccggg    1440
gtcaaccgcg ccagtgtcag cgccttcgcc acgaccaata ggatggagct cgagggcgcg    1500
agttaccagg tgcccccgca gccgaacggc atgaccaaca acctccaggg cagcaacacc    1560
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca cgtgtggat ggagagggac     1800
gtgtacctcc aaggacccat ctgggccaag atcccagaga cggggcgca ctttcacccc    1860
tctccggcca tgggcggatt cggactcaaa cacccaccgc catgatgct catcaagaac      1920
acgcctgtgc ccggaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca acgacccca gtttgtggac     2100
tttgccccgg acagcaccgg ggaatacaga accaccagac ctatcggaac ccgataccttt   2160
acccgacccc tttaa                                                     2175
```

<210> SEQ ID NO 10
<211> LENGTH: 724
<212> TYPE: PRT

<213> ORGANISM: Artificial
<220> FEATURE:
<223> OTHER INFORMATION: MV53

<400> SEQUENCE: 10

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
            85                  90                  95

Ala Glu Phe Gln Glu Lys Leu Ala Asp Asp Thr Ser Phe Gly Gly Asn
        100                 105                 110

Leu Gly Lys Ala Val Phe Gln Ala Lys Lys Arg Val Leu Glu Pro Phe
    115                 120                 125

Gly Leu Val Glu Glu Gly Ala Lys Thr Ala Pro Thr Gly Lys Arg Ile
130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Arg Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Arg Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
```

```
                385                 390                 395                 400
Asn Phe Glu Phe Thr Tyr Asn Phe Glu Glu Val Pro Phe His Ser Ser
                    405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 11
<211> LENGTH: 2175
<212> TYPE: DNA
<213> ORGANISM: adeno-associated virus 5

<400> SEQUENCE: 11
atgtcttttg ttgatcaccc tccagattgg ttggaagaag ttggtgaagg tcttcgcgag    60
tttttgggcc ttgaagcggg cccaccgaaa ccaaaaccca atcagcagca tcaagatcaa   120
gcccgtggtc ttgtgctgcc tggttataac tatctcggac ccggaaacgg tctcgatcga   180
ggagagcctg tcaacagggc agacgaggtc gcgcgagagc acgacatctc gtacaacgag   240
```

```
cagcttgagg cgggagacaa ccctacctc aagtacaacc acgcggacgc cgagtttcag      300
gagaagctcg ccgacgacac atccttcggg ggaaaccctcg gaaaggcagt ctttcaggcc    360
aagaaaaggg ttctcgaacc ttttggcctg gttgaagagg gtgctaagac ggcccctacc    420
ggaaagcgga tagacgacca ctttccaaaa agaaagaagg ctcggaccga agaggactcc    480
aagccttcca cctcgtcaga cgccgaagct ggacccagcg atcccagca gctgcaaatc     540 ccagcccaac cagcctcaag tttgggagct gatacaatgt ctgcgggagg tggcggccca    600
ttgggcgaca ataaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag caccccctgg gggtactttg actttaaccg cttccacagc    840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa cttgaggag gtgcccttcc actccagctt cgctcccagt   1260
cagaacctgt tcaagctggc caaccccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgccccgca gccgaacggg atgaccaaca acctccaggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cggggggcgca cttcacccc   1860 tctccggcca tgggcggatt cggactcaaa cacccaccgc ccatgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca acgaccccca gtttgtggac   2100
tttgccccgg acagcaccgg ggaatacaga accaccagac ctatcggaac ccgatacctt   2160
acccgacccc tttaa                                                    2175
```

<210> SEQ ID NO 12
<211> LENGTH: 724
<212> TYPE: PRT
<213> ORGANISM: adeno-associated virus 5

<400> SEQUENCE: 12

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys

-continued

```
                20                  25                  30
Pro Asn Gln Gln His Gln Asp Gln Ala Arg Gly Leu Val Leu Pro Gly
            35                  40                  45
Tyr Asn Tyr Leu Gly Pro Gly Asn Gly Leu Asp Arg Gly Glu Pro Val
50                  55                  60
Asn Arg Ala Asp Glu Val Ala Arg Glu His Asp Ile Ser Tyr Asn Glu
65                  70                  75                  80
Gln Leu Glu Ala Gly Asp Asn Pro Tyr Leu Lys Tyr Asn His Ala Asp
                85                  90                  95
Ala Glu Phe Gln Glu Lys Leu Ala Asp Asp Thr Ser Phe Gly Gly Asn
            100                 105                 110
Leu Gly Lys Ala Val Phe Gln Ala Lys Lys Arg Val Leu Glu Pro Phe
            115                 120                 125
Gly Leu Val Glu Glu Gly Ala Lys Thr Ala Pro Thr Gly Lys Arg Ile
            130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Pro Leu Gly Asp Asn Asn Gln Gly Ala
            195                 200                 205
Asp Gly Val Gly Asn Ala Ser Gly Asp Trp His Cys Asp Ser Thr Trp
            210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
            275                 280                 285
Arg Leu Ile Asn Asn Tyr Trp Gly Phe Arg Pro Arg Ser Leu Arg Val
            290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gln Tyr Gly Tyr
            355                 360                 365
Ala Thr Leu Asn Arg Asp Asn Thr Glu Asn Pro Thr Glu Arg Ser Ser
            370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
            435                 440                 445
```

```
Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 13
<211> LENGTH: 21
<212> TYPE: DNA
<213> ORGANISM: Artificial
<220> FEATURE:
<223> OTHER INFORMATION: forward primer

<400> SEQUENCE: 13
aggctcggac cgaagaggac t                                         21

<210> SEQ ID NO 14
<211> LENGTH: 30
<212> TYPE: DNA
<213> ORGANISM: Artificial
<220> FEATURE:
<223> OTHER INFORMATION: reverse primer

<400> SEQUENCE: 14
atcgagcggc cgcaagaggc agtattttac                                30
```